US008252977B2

(12) United States Patent
Tanksley et al.

(10) Patent No.: US 8,252,977 B2
(45) Date of Patent: Aug. 28, 2012

(54) POLYNUCLEOTIDES ENCODING CAROTENOID AND APOCARTENOID BIOSYNTHETIC PATHWAY ENZYMES IN COFFEE

(75) Inventors: Steven D. Tanksley, Dryden, NY (US); Chenwei Lin, Auburndale, MA (US); Andrew Simkin, Tours (FR); James Gérard McCarthy, Noizay (FR); Vincent Petiard, Tours (FR)

(73) Assignees: Nestec S. A., Vevey (CH); Cornell University, Ithaca, NY (US)

( * ) Notice: Subject to any disclaimer, the term of this patent is extended or adjusted under 35 U.S.C. 154(b) by 854 days.

(21) Appl. No.: 11/990,835

(22) PCT Filed: Sep. 1, 2006

(86) PCT No.: PCT/US2006/034402
§ 371 (c)(1),
(2), (4) Date: Feb. 27, 2009

(87) PCT Pub. No.: WO2007/028115
PCT Pub. Date: Mar. 8, 2007

(65) Prior Publication Data
US 2009/0178156 A1     Jul. 9, 2009

Related U.S. Application Data

(60) Provisional application No. 60/714,106, filed on Sep. 2, 2005.

(51) Int. Cl.
*A01H 5/00* (2006.01)
*A01H 5/10* (2006.01)
*C12N 15/29* (2006.01)
*C12N 15/52* (2006.01)
*C12N 15/82* (2006.01)

(52) U.S. Cl. ....... 800/287; 800/285; 800/298; 536/23.2; 536/23.6; 435/320.1; 435/419

(58) Field of Classification Search .................. 800/285, 800/287, 298; 536/23.2, 23.6; 435/419, 435/320.1
See application file for complete search history.

(56) References Cited

U.S. PATENT DOCUMENTS

| 6,653,530 B1 * | 11/2003 | Shewmaker et al. ......... 800/282 |
| 2002/0128464 A1 * | 9/2002 | Busch et al. .................. 536/23.6 |

FOREIGN PATENT DOCUMENTS

| DE | 199 09 637 A1 | 3/1999 |
| EP | 1 156 117 A2 | 4/2001 |
| WO | WO 98/06862 | 2/1998 |
| WO | WO 00/11199 | 3/2000 |
| WO | WO 03/020015 A2 | 3/2003 |
| WO | WO 2004/003208 A2 | 1/2004 |

OTHER PUBLICATIONS

Akiyama, M. et al., "Analysis of Volatile Compounds Released During the Grinding of Roasted Coffee Beans Using Solid-Phase Microextraction," *J. Agric. Food Chem.*, vol. 51, pp. 1961-1969, 2003. XP-002431389.

Czerny, M. and Grosch, W., "Potent Odorants of Raw Arabica Coffee. Their Changes During Roasting," *J. Agric. Food Chem.*, vol. 48, pp. 868-872, 2000. XP-002431388.

Iuchi, S. et al., "Regulation of Drought Tolerance by Gene Manipulation of 9-*cis*-Epoxycarotenoid Biosynthesis in *Arabidopsis*," *The Plant Journal*, vol. 27(4), pp. 325-333, 2001. XP-002973637.

Ortiz, A. et al., "Volatile Composition of Coffee Berries at Different Stages of Ripeness and Their Possible Attraction to the Coffee Berry Borer Hypothenemus Hampei (Coleoptera: Curculionidae)," *J. Agric. Food Chem.*, vol. 52, pp. 5914-5918, 2004. XP-002431391.

Variyar, P.S. et al., "Flavoring Components of Raw Monsooned Arabica Coffee and Their Changes During Radiation Processing," *Agricultural and Food Chemistry*, vol. 31, pp. 7945-7950, 2003. XP-002431390.

Agrawal, G.K., et al., "Screening o The Rice Viviparous Mutants Generated by Endogenous Retrotransposon Tos17 Insertion. Tagging of a Zeaxanthin Epoxidase Gene and a Novel OsTATC Gene," *Plant Physiol.*, vol. 125, pp., Vol., pp. 1248-1257, 2001.

Akiyama, M. et al. "Analysis of Volatile Compounds Released During the Grinding of Roasted Coffee Beans Using Solid-Phase Microextraction," *J Agric Food Chem.*, vol. 51(7): pp. 1961-1969, 2003.

Albrecht, M. et al. "Molecular Cloning and Functional Expression in *E.Coli* of a Novel Plant Enzyme Mediating ζ-Carotene Desaturation," *FEBS Letters.*, vol. 372:, pp. 199-202, 1995.

Al-Babili, S. et al. "Identification of a Novel Gene Encoding for Neoxanthin Synthase From *Sola tuberosum*," *FEBS Letters*, vol. 485, pp. 168-172, 2000.

Al-Babili, S. et al. "Biosynthesis of Beta-Carotene (Provitamin A) in Rice Endosperm Achieved by Genetic Engineering," *Novartis Found Symp.*, vol. 236, pp. 219-232, 2001.

Arrach, N. et al., "A Single Gene for Lycopene Cyclase, Phytoene Synthase, and Regulation of Carotene Biosynthesis in *Phycomyces*,". *PNAS* 98(4):1687-1692, 2001.

Aust, O. et al., "Supplementation With Tomato-Based Products Increases Lycopene, Phytofluene, and Phytoene Levels in Human Serum and Protects Against UV-Light Induced Erythema," *Int. J. Vitam. Nutr. Res.* 75:54-60, 2005.

Baldwin, E.A. et al., "Quantitative Analysis of Flavor Parameters in Six Florida Tomato Cultivars (*Lycopersicon esculentum*)," *J. Agri, Food. Chem.* 39: 1135-1140, 1991.

Baldwin, E.A. et al., "Flavor Trivia and Tomato Aroma: Biochemistry and Possible Mechanisms for Control of Important Aroma Components," *Hort. Sci.* 35(6): 1013-1021, 2000.

Bartley, G.E. et al., "A Tomato Gene Expressed During Fruit Ripening Encodes an Enzyme of the Carotenoid Biosynthesis Pathway," *J. Biol. Chem.* 267: 5036-5039, 1992.

Bartley, G.E. and Ishida, B.K., "Zeta-Carotene Desaturase From Tomato," *Plant Physiol.* 121:1383, 1999.

(Continued)

Primary Examiner — Russell Kallis
(74) Attorney, Agent, or Firm — Potter Anderson & Corroon LLP

(57) ABSTRACT

Polynucleotides encoding polypeptides that comprise the biosynthetic pathway for carotenoids and apocarotenoids in the coffee plant are disclosed. Also disclosed are a promoter sequence from a coffee carotenoid gene, and methods for using these polynucleotides, polypeptides, and promoter sequences for gene regulation and the manipulation of flavor, aroma, and other features of coffee beans, as well as the manipulation of photosynthesis in the coffee plant.

20 Claims, 30 Drawing Sheets

OTHER PUBLICATIONS

Bäumlein, H. et al., "*Cis*-Analysis of a Seed Protein Gene Promoter: The Conservative RY Repeat CATGCATG Within the Legumin Box Is Essential for Tissue-Specific Expression of a Legumin Gene," *Plant J.* 2: 233-239, 1992.

Beyer, P. et al., "Golden Rice: Introducing the Beta-Carotene Biosynthesis Pathway Into Rice Endosperm by Genetic Engineering to Defeat Vitamin A Deficiency," *J Nutr.* 132(3):506S-510S, 2002.

Boelsma, E., et al. "Nutritional Skin Care: Health Effects of Micronutrients and Fatty Acids," *Am. J. Clin. Nutr.*, vol. 73:853-864, 2001.

Bouvier, F. et al., "Xanthophyll Biosynthesis. Cloning, Expression, Functional Reconstitution, and Regulation of Beta-Cyclohexenyl Carotenoid Epoxidase From Pepper (*Capsicum annuum*)," *J Biol Chem.* 271(46):28861-28867, 1996.

Bouvier, F. et al., "Biosynthesis of the Food and Cosmetic Plant Pigment Bixin (Annatto)," *Science* 300: 289-291, 2003.

Bouvier, F. et al., "Oxidative Remodelling of Chromoplast Carotenoids: Identification of a Carotenoid Cleavage Dioxygenase CsCCD and CsZCD Genes Involved in Crocus Secondary Metabolic Biogenesis," *Plant Cell* 15: 47-62, 2003.

Bouvier, F. et al., "Oxidative Tailoring of Carotenoids: A Prospect Towards Novel Functions in Plants," *Trends Plant Sci.* 10(4):187-194, 2005.

Bramley, P.M. "Is Lycopene Beneficial to Human Health?" *Phytochemistry.*, vol. 54(3), pp. 233-236, 2000.

Britton, G. "Biosynthesis of Carotenoids. In: Goodwin TW (Ed), Plant Pigments.," Academic Press, London, p. 133, 1988.

Britton, G., "Structure and Properties of Carotenoids in Relation to Function," *FASEB J.*, 9:1551, 1995.

Bugos, R.C., "Xanthophyll Cycle Enzymes Are Members of the Lipocalin Family, The First Identified From Plants," *Biol Chem.* 273(25):15321, 1998.

Burbidge, A. et al., "Structure and Expression of a cDNA Encoding Zeaxanthin Epoxidase, Isolated From a Wilt-Related Tomato (*Lycopersicon esculentum* Mill.)," *J. Exp. Bot.* 48, 1749-1750, 1997.

Burden, R.S. et al., "Synthesis and Plant Growth Inhibitory Properties of (±)-*O*-Methylxanthoxin," *Phytochemistry*,. 11: 2295-2299, 1972.

Buttery, R. and Ling, L. "Volatile Components of Tomato Fruit and Plant Parts: Relationship and Biogenesis. pp. 23-34. In: Teranishi R, Buttery R, Sugisawa H, (Eds) Bioactive Volatile Compounds From Plants," ACS Books. Washington, DC, 1993.

Buttery, R.G. et al.,"Characterisation of Additional Volatile Components of Tomato," *J. Agri, Food. Chem.* 19: 524-52, 1971.

Buttery, R.G. et al., "Quantitative Studies on Origins of Fresh Tomato Aroma Volatiles," *J. Agric. Food Chem.* 36: 1247-1250, 1988.

Buttery, R.G. et al., "Quantitative and Sensory Studies on Tomato Paste Volatiles," *J. Agric. Food Chem.* 38: 336-340, 1990.

Buttery, R.G. et al., "Fresh Tomato Aroma Volatiles: A Quantitative Study," *J. Agri, Food. Chem.* 35: 540-544, 1987.

Carol, P. et al. "Mutations in the *Arabidopsis* Gene IMMUTANS Cause a Variegated Phenotype by Inactivating a Chloroplast Terminal Oxidase Associated With Phytoene De-saturation," *Plant Cell*, 11: 57-68, 1999.

Comhaire, F.H. and Mahmoud, A. "The Role of Food Supplements in the Treatment of the Infertile Man," *Reprod Biomed Online.* 7(4):385-391, 2003.

Cunningham, F.X. and Gantt, E., "Genes and Enzymes of Carotenoid Biosynthesis in Plants," *Annu Rev Plant Physiol Plant Mol Biol* 49: 557-583, 1998.

Cunningham, F.X. and Gantt, E. "One Ring or Two? Determination of Ring Number in Carotenoids by Lycopene Epsilon-Cyclases.," *PNAS* 98(5):2905-2910, 2001.

Cunningham, F.X. Jr. and Gantt, E., "A Study in Scarlet: Enzymes of Ketocarotenoid Biosynthesis in the Flowers of *Adonis aestivalis*," *Plant J.* 41(3):478-492, 2005.

Cunningham, F.X. et al. "Functional Analysis of the Beta and Epsilon Lycopene Cyclase Enzymes of *Arabidopsis* Reveals a Mechanism for Control of Cyclic Carotenoid Formation," *Plant Cell* 8(9) : 1613-1626, 1996.

Cunningham, F.X. et al. "Molecular Structure and Enzymatic Function of Lycopene Cyclase From the *Cyanobacterium synechococcus* sp Strain PCC7942," *Plant Cell*, 6: 1107-1121, 1994.

Czerny, M. and Grosch, W, "Potent Odorants of Raw Arabica Coffee. Their Changes During Roasting," *J Agric Food Chem.* 48(3):868-872, 2000.

Czerny, M. et al., "Sensory Study on the Character Impact Odorants of Roasted Arabica Coffee," *J Agric Food Chem.* 47(2): 695-699, 1999.

Demmig-Adams, B. et al., "In Vivo Functions of Carotenoids in Higher Plants," *FASEB J.* 10:403-412, 1996.

Deruère, J. et al., "Structures and Expression of Two Plant Genes Encoding Chromoplast-Specific Proteins: Occurrence of Partially Spliced Transcripts," *Biochem. Biophys. Res. Com.* 199(3): 1144-1150, 1994.

Deruère, J. et al., "Fibril Assembly and Carotenoid Over-accumulation in Chromoplasts: A Model for Supramolecular Lipoprotein Structures," *Plant Cell* 6: 119-133, 1994.

Di Mascio, P et al., "Antioxidant Defense Systems: The Role of Carotenoids, Tocopherols, and Thiols$^{1-3}$," *Am. J. Clin. Nutr.*, 53:194S-200S, 1991.

Da Silva, E.A. et al., "Abscisic Acid Controls Embryo Growth Potential and Endosperm Cap Weakening During Coffee (*Coffea arabica* Cv. Rubi) Seed Germination," *Planta.* 220(2):251-261, 2004.

Eugster, C.H. et al., "Crocetindialdehyd Und Crocetinhalbaldehyd Als Blütenfarbstoffe Von *Jacquinia angustifolia*," *Helv. Chim. Acta*, vol. 52, pp. 806-807, 1969.

Fay, L.B. et al., "Potential of Gas Chromatography-Orthogonal Acceleration Time-of-Flight Mass Spectrometry (GC-oaTOFMS in Flavor Research," *J. Agric. Food Chem.* 51: 2708-2713, 2003.

Fraser, P.D. and Bramley, P.M. "The Biosynthesis and Nutritional Uses of Carotenoids," *Prog Lipid Res.* 43(3): 228-265, 2004.

Fraser, P.D. et al., "Application of High-Performance Liquid Chromatography With Photodiode Array Detection to the Metabolic Profiling of Plant Isoprenoids," *Plant J.* 24: 551-558, 2000.

Fray, R.G. et al., "Constitutive Expression of a Fruit Phytoene Synthase Gene in Transgenic Tomatoes Causes Dwarfism by Redirecting Metabolites From the Gibberellin Pathway," *Plant J.*, vol. 8: 693-701, 1995.

Gaziano, J.M. and Hennekens, C.H. "The Role of Beta-Carotene in the Prevention of Cardiovascular Disease," *Ann. NY Acad. Sci.* 691:148-155, 1993.

Hieber, A.D., et al., "Plant Lipocalins: Violaxanthin De-Epoxidase and Zeaxanthin Epoxidase," *Biochim Biophys Acta.* 1482(1-2): 84-91, 2000.

Hirschberg, J. Molecular Biology of Carotenoid Biosynthesis (in) Britton, G., Liaaen-Jensen, S. and Pfander, H. (Eds.); *Carotenoids vol. 3: Biosynthesis and Metabolism*: 149-194; Birkhaeuser Verlag, Basel, Boston, Berlin (1998).

Hsieh, K. and Huang, A.H.C. "Endoplasmic Reticulum, Oleosins, and Oils in Seeds and Tapetum Cells," *Plant Physiol* 136: 3427-3434, 2004.

Huang, A.H.C., "Oleosins and Oil Bodies in Seeds and Other Organs," *Plant Physiol* 110(4): 1055-1061, 1996.

Hugueney, P. et al., "Characterization and Molecular Cloning of a Flavoprotein Catalysing the Synthesis of Phytofluene and Zeta-Carotene in *Capsicum* Chromoplasts," *Eur. J Biochem.* 209: 399-407, 1992.

Inoue, K., et al., "Carotenoid Hydroxylation—P450 Finally!" *Trends Plant Sci.*, vol. 9(11), pp. 515-517, 2004.

Josse, E.M. et al., "A Plastid Terminal Oxidase Associated With Carotenoid Desaturation During Chromoplast Differentiation," *Plant Physiol.* 123: 1427-1436, 2000.

Josse, E.M. et al., "In Vitro Characterization of Plastid Terminal Oxidase (PTOX)," *Eur. J. Biochem.* 270: 3787-3794, 2003.

Jyonouchi, H. et al., "Studies of Immunomodulating Actions of Carotenoids. II. Astaxanthin Enhances In Vitro Antibody Production to T-Dependent Antigens Without Facilitating Polyclonal B-Cell Activation," *Nutr Cancer*.19(3): 269-280, 1993.

Kato-Noguchi, H. "An Endogenous Growth Inhibitor, 3-Hydroxy-β-Ionone. I. Its Role in Light-Induced Growth Inhibition of Hypocotyls of *Phaseolus vulgaris*," *Physiol. Plant.* 86: 583-586, 1992.

Kato-Noguchi, H. et al., "A Growth Inhibitor, R-(−)-3-Hydroxy-β-Ionone, From Light-Grown Shoots of a Dwarf Cultivar of *Phaseolus vulgaris*," *Phytochem.* 33: 553-555, 1993.

Kiefer, C. et al., "Identification and Characterization of a Mammalian Enzyme Catalyzing the Asymmetric Oxidative Cleavage of Provitamin A," *J Biol Chem.* 276(17): 14110-14116, 2001.

Kjeldsen, F. et al., "Changes in Volatile Compounds of Carrots (*Daucus carota* L.) During Refrigerated and Frozen Storage," *J. Agric. Food Chem.* 51: 5400-5407, 2003.

Kuntz, M. "Plastid Terminal Oxidase and Its Biological Significance," *Planta*, vol. 218: 896-899, 2004.

Laizet, Y. et al., "Subfamily Organization and Phylogenetic Origin of Genes Encoding Plastid Lipid-Associated Proteins of the Fibrillin Type," *J. Genome Sci. Tech.* 3(1): 19-28, 2004.

Li, L. et al., "A Novel Gene Mutation That Confers Abnormal Patterns of β-Carotene Accumulation in Cauliflower (*Brassica oleracea* Var. *botrytis*)," *Plant J.* 26(1): 59-67, 2001.

Lin C. et al., Coffee and Tomato Share Common Gene Repertoires as Revealed by Deep Sequencing of Seed and Cherry Transcripts, *Theor. Appl. Genet.*, vol. 112, pp. 114-130, 2005.

Lindgren, L.O. et al., "Seed-Specific Over-expression of an Endogenous *Arabidopsis* Phytoene Synthase Gene Results in Delayed Germination and Increased Levels of Carotenoids, Chlorophyll, and Abscisic Acid," *Plant Physiol.*, vol. 132(2): 779-785, 2003.

Lutz, A. and Winterhalter, P. "Bio-oxidative Cleavage of Carotenoids—Important Route to Physiological Active-Plant Constituents," *Tetrahedron Letters*, vol. 33: 5169-5172, 1992.

Marin, E. et al., "Molecular Identification of Zeaxanthin Epoxidase of *Nicotiana plumbaginifolia*, A Gene Involved in Abscisic Acid Biosynthesis and Corresponding to the ABA Locus of *Arabidopsis thaliana*," *EMBO J.* 15(10): 2331-2342, 1996.

Mahattanatawee, K. et al., "Identification and Aroma Impact of Norisoprenoids in Orange Juice," *J Agric Food Chem.* 53(2): 393-397, 2005.

Matthews-Roth, M.M. "Carotenoids in Erythropoietic Protoporphyria and Other Photosensitivity Diseases," *Ann. NY Acad. Sci.* 691: 127-138, 1993.

Mayne, S.T. "Beta-Carotene, Carotenoids, and Disease Prevention in Humans," *FASEB J.* 10: 690-701, 1996.

Mbeguie-A- et al., "Molecular Cloning and Nucleotide Sequences of PA-ZE (Accession No. AF071888) and PA-ZE2 (Accession No. AF159948), Two Cdnas From Apricot Fruit Coding for a Zeaxanthin Epoxidase. Gene Expression During Fruit Ripening," *Plant Physiol.* 122 (1): 291, 2000.

Moehs, C.P. et al., "Analysis of Carotenoid Biosynthetic Gene Expression During Marigold Petal Development," *Plant Mol. Biol.* 45: 281-293, 2001.

Nagao, A. "Oxidative Conversion of Carotenoids to Retinoids and Other Products," *J. Nutr.* 134(1): 237S-240S, 2004.

Neill, S,J, et al., "Cloning of a Wilt-Responsive cDNA From *Arabidopsis thaliana* Suspension Culture cDNA Library That Encodes a Putative 9-Cis-Epoxy-Carotenoid Dioxygenase.," *J. Exp. Bot.* 49: 1893-1894, 1998.

Ortiz, A. et al., "Volatile Composition of Coffee Berries At Different Stages of Ripeness and Their Possible Attraction to the Coffee Berry Borer *Hypothenemus hampei* (Coleoptera: Curculionidae)," *J Agric Food Chem.* 52(19): 5914-5918, 2004.

Paine J.A. et al., "Improving the Nutritional Value of Golden Rice Through Increased Pro-Vitamin A Content," *Nature Biotechnol.* 23(4): 482-487, 2005.

Parry, A.D. and Horgan, R. Carotenoids and Abscisic Acid (ABA) Biosynthesis in Higher Plants. *Physiol. Plant.* 82: 320-326, 1991.

Pecker, I. et al., (1992) "A Single Polypeptide Catalyzing the Conversion of Phytoene to Zeta-Carotene Is Transcriptionally Regulated During Tomato Fruit Ripening," *Proc. Natl. Acad. Sci. U.S.A.* 89: 4962-4966, 1992.

Pogson, B. et al., "*Arabidopsis* Carotenoid Mutants Demonstrate That Lutein Is Not Essential for Photosynthesis in Higher Plants," *Plant Cell* 8(9): 1627-1639, 1996.

Ravanello, M.P. et al., "Coordinate Expression of Multiple Bacterial Carotenoid Genes in Canola Leading to Altered Carotenoid Production," *Metab Eng.* 5(4): 255-263, 2003.

Ray, J. et al., "Cloning and Characterization of a Gene Involved in Phytoene Synthesis From Tomato," *Plant Mol. Biol.* 19: 401-404, 1992.

Rey P. et al., "Over-Expression of a Pepper Plastid Lipid-Associated Protein in Tobacco Leads to Changes in Plastid Ultrastructure and Plant Development Upon Stress," *Plant J.* 21(5): 483-494, 2000.

Richman, A.S. et al., "Diterpene Synthesis in *Stevia rebaudiana*: Recruitment and Up-Regulation of Key Enzymes From the Gibberellin Biosynthetic Pathway," *Plant J.* 19 (4): 411-421, 1998.

Römer S. et al., "Expression of the Genes Encoding the Early Carotenoid Biosynthetic Enzymes in *Capsicum Annuum*. *Biochem, Biophys. Research Commun.* 196: 1414-1421, 1993.

Ronen, G. et al., "Regulation of Carotenoid Biosynthesis During Tomato Fruit Development: Expression of the Gene for Lycopene Epsilon-Cyclase is Down-Regulated During Ripening and is Elevated in the Mutant Delta," *Plant J.* 17: 341-351, 1999.

Sandmann, G. "Carotenoid Biosynthesis in Micro-Organisms and Plants," *Eur. J. Biochem.* 223: 7-24, 1994.

Sato, S. et al., "Structural Analysis of *Arabidopsis thaliana* Chromosome 3. I. Sequence Features of the Regions of 4,504,864 by Covered by Sixty P1 and TAC Clones," *DNA Res.* 7 (2): 131-135, 2000.

Schwartz, S.H. et al., "Characterization of a Novel Carotenoid Cleavage Dioxygenase From Plants," *J. Biol. Chem.* 276: 25208-25211, 2001.

Scolnik, P.A. and Bartley, G. E. "Nucleotide Sequence of Zeta-Carotene Desaturase From *Arabidopsis*," *Plant Physiol.* 109: 1499, 1995.

Seddon J.M. et al., "Dietary Carotenoids, Vitamins A, C, and E, and Advanced Age-Related Macular Degeneration," *J. Am. Med. Assoc.* 272: 1413-1420, 1994.

Shewmaker, C.K. et al., "Seed-Specific Over-expression of Phytoene Synthase: Increase in Carotenoids and Other Metabolic Effects," *Plant J.* 20(4): 401-412, 1999.

Sies, H. and Stahl, W. "Carotenoids and UV Protection. *Photochem. Photobiol.*," *Sci.* vol. 3(8), pp. 749-752, 2004.

Simkin, A.J. et al.,, "Circadian Regulation of the PhCCD1 Carotenoid Cleavage Dioxygenase Controls Emission of β-Ionone, a Fragrance Volatile of Petunia Flowers," *Plant Physiol.* 136(3): 3504-3514, 2004.

Simkin, A.J. et al., "The Tomato Carotenoid *Cleavage Dioxygenase* 1 Genes Contribute to the Formation of the Flavor Volatiles β-Ionone, Pseudoionone and Geranylacetone," *Plant J.* 40(6): 882-894, 2004.

Simkin, A.J. et al., "Plastid Lipid Associated Proteins of the Fibrillin Family: Structure, Localisation, Function and Gene Expression," *Rec Res Dev Biochem* 5: 307-316, 2004.

Soar, C.J., et al., Gradients in Stomatal Conductance, Xylem Sap ABA and Bulk Leaf ABA Along Canes of *Vitis vinifera* Cv Shiraz: Molecular and Physiological Studies Investigating Their Source, *Functional Plant Biology*, vol. 31, pp. 659-669, 2004.

Spanier. A.M. et al., "Meat Flavor: Contribution of Proteins and Peptides to the Flavor of Beef," *Adv Exp Med Biol.* 542: 33-49, 2004.

Stalberg. K. et al., "Synthesis of Ketocarotenoids in the Seed of *Arabidopsis thaliana*," *Plant J.* 36: 771-779, 2003.

Stevens, A.A. "Relationship Between Polyene-Carotene Content and Volatile Compound Composition of Tomatoes," *J. Am. Soc. Hort. Sci.* 95: 461-464, 1970.

Suzuki, M. et al., "Identification of (3S, 9R)- and (3S, 9S)-Megastigma-6,7-Dien-3,5,9-Triol 9-O-β-D-Glucopyranosides as Damascenone Progenitors in the Flowers of *Rosa damascena* Mill." *Biosci Biotechnol Biochem.* 66(12): 2692-2697, 2002.

Tan, B.C. et al., "Genetic Control of Abscisic Acid Biosynthesis in Maize," *Proc. Natl. Acad. Sci.* USA, 94: 12235-12240, 1997.

Tan, B.C. et al., "Molecular Characterisation of the 9-Cis Epoxycarotenoid Dioxygenase Gene Family," *Plant J.* 35: 44-56, 2003.

Tanaka, T. et al., Chemoprevention of Mouse Urinary Bladder Carcinogenesis by the Naturally Occurring Carotenoid Astaxanthin Carcinogenesis, vol. 15, 15-19, Copyright © 1994 by Oxford University Press.

Tandon, J.S. et al., "274 Crocetin-dialdehyde from *Coleus forskolii* Brig$^{1)}$., Labiatae," *Helvetica Chim. Acta*, vol. 62, pp. 2706-2707, 1979.

Taylor, A. "Cataract: Relationship Between Nutrition and Oxidation," *J. Am. Coll. Nutr.*, vol. 12: 138-146, 1993.

Thompson, A.J. et al., "Complementation of *Notabilis*, an Abscisic Acid-Deficient Mutant of Tomato: Importance of Sequence Context and Utility of Partial Complementation," *Plant Cell Environ.* 27 (4): 459-471, 2004.

Tian, L. and Dellapenna, D. "Characterization of a Second Carotenoid B-Hydroxylase Gene From *Arabidopsis* and its Relationship to the *LUT1* Locus," *Plant Mol Biol.*, vol. 47(3): 379-388, 2001.

Tian, L. and Dellapenna, D. "Progress in Understanding the Origin and Functions of Carotenoid Hydroxylases in Plants," *Arch Biochem Biophys.* ;430(1):22-29, 2004.

Tian, L. et al., "The *Arabidopsis* LUT1 Locus Encodes a Member of the Cytochrome P450 Family That is Required for Carotenoid Epsilon-Ring Hydroxylation Activity," *PNAS* 6;101(1): 402-407, 2004.

Variyar P. et al. "Flavoring Components of Raw Monsooned Arabica Coffee and Their Changes During Radiation Processing," *J Agric Food Chem.* 51(27): 7945-7950, 2003.

Vishnevetsky M. et al., "Carotenoid Sequestration in Plants: The Role of Carotenoid-Associated Proteins," *Trends Plant Sci.*, vol. 4(6), pp. 232-235, 1999.

Von Lintig, J. and Vogt, K. "Filling the Gap in Vitamin A Research. Molecular Identification of an Enzyme Cleaving Beta-Carotene to Retinal," *J. Biol. Chem.* 275(16): 11915-11920, 2000.

Watzl, B. et al., "Modulation of Human T-Lymphocyte Functions by the Consumption of Carotenoid-Rich Vegetables," *Br. J. Nutr.* 82: 383-389, 1999.

Winterhalter, P. and Schreier, P. "The Generation of Norisoprenoid Volatiles in Starfruit (*Averrhoa carambola* L.): A Review," *Food Rev. International* 11: pp. 237-254, 1995.

\* cited by examiner

FIG. 4A

```
1   ------------------------------------------------------------ CcPDS
1   VVVEGNVSPANLPYQNG---FLEALSS----------GGSELMGHSFRVETSQALKTRTRPRRSTAGPLVVVC AtPDS TC261857
1   MPQIGLVSAVNLRVQGSSAYLNSSRSSSLGTESRDGCLQRNSLCFAGSESMGHKLKIRTPHATTRRLVK--TLGPLKVVC LePDS X59948
1   MPQIGLVSAVNLRVQGNSAYLWSSRSS-LGTDSCDGCSQRNSLCFGGSDSMSHRLKIRNPHSITRRLAK--TFRPLKVVC CaPDS X68058

1   IDYPRPELENAVNYLEAAYLSSIFRTSEHPNKPLEVVIAGAGLAGLSTAKYLADAGHKPIVLEARDVLGGKVAAWKDDDG CcPDS
60  VDIERPELDNTVNFLEAASLSASFRSAPREAKPLKVVIAGAGLAGLSTAKYLADAGHKPILLEARDVLGGKIAAWKDEDG AtPDS TC261857
79  IDYPRPELDNTVNYLEAAFLSSIFRASPRPTKPLEIVIAGAGLGGLSTAKYLADAGHKPILLEARDVLGGKVAAWKDDDG LePDS X59948
78  IDYPRPELDNTVNYLEAAFLSSSFRSSPRPTKPLEIVIAGAGLGGLSTAKYLADAGHKPILLEARDVLGGKVAAWKDDDG CaPDS X68058

81  DWYETGLHVFFGAYPNMQNLFGELGINDRLQWKEHSMIFAMPNKPGEFSRFDFPEVLPAPLNGIWAILKNNDMLTWPEKV CcPDS
140 DWYETGLHIFFGAYPNVQNLFGELGINDRLQWKEHSMIFAMPSKPGEFSRFDFPDVLPAPLNGIWAILRNNEMLTWPEKI AtPDS TC261857
159 DWYETGLHIFFGAYPNIQNLFGELGINDRLQWKEHSMIFAMPSKPGEFSRFDFSEALPAPLNGILAILKNNEMLTWPEKV LePDS X59948
158 DWYETGLHIFFGAYPNMQNLFGELGINDRLQWKEHSMIFAMPNKPGEFSRFDFPEALPAPLNGILAILKNNEMLTWPEKV CaPDS X68058

161 KFAIGLLPAILGGQSYVEAQDGITVKDWMRKQGIPDRVTDEVFIAMSKALNFINPDELSMQCILIALNRFLQEKHGSKMA CcPDS
220 KFAIGLLPAMVGGQAYVEAQDGISVKDMMKQGVPERVTDEVFTAMSKALNFINPDELSMQCILIALNRFLQEKHGSKMA AtPDS TC261857
239 KFAIGLLPAMLGGQSYVEAQDGISVKDMMRKQGVPDRVTDEVFIAMSKALNFINPDELSMQCILIALNRFLQEKHGSKMA LePDS X59948
238 KFAIGLLPAMLGGQSYVEAQDGISVKDMMRKQGVPDRVTDEVFIAMSKALNFINPDELSMQCILIALNRFLQEKHGSKMA CaPDS X68058

241 FLDGNPPERLCMPIVEHIESRGGRVHLNSRIKKIELNIAGSVENFLISNGTVIRGDAVVFATPVDILKLLLPEDWKEIPY CcPDS
300 FLDGNPPERLCMPVVEHIESIGGEVQLNSRIKKIELNDDGIVKSFLITNGSTVEGDAVVFAAPVDILKLLLPEDWKEIPY AtPDS TC261857
319 FLDGNPPERLCMPIVEHIESKGGQVRLNSRIKKIELNDDGSVKSFILSDGSAIEGDAFVFAAPVDIEKLLLPEDWKEIPY LePDS X59948
318 FLDGNPPERLCMPIVEHIESKGGQVRLNSRIKKIELNEDGSVKCFILNDGSTIEGDAFVFATPVDIEKLLLPEDWKEIPY CaPDS X68058
```

FIG. 4B
(Page 1 of 2)

```
321 FPKLEKLVGVPVINVHIWFDRKLRNTYDHLLFSRSPLLS                                              CcPDS
380 FKKIDKLVGVPVINVHIWFDRKLKNTYDHLLFSRSNLLSVYADMSITCKEYYDPNRSMLELVFAPAEEWISRTDSDIIDA     AtPDS TC261857
399 FQKLEKLVGVPVINVHIWDRKLKNTYDHLLFSRSSLLSVYADMSVTCKEYYPNCSMLELVFAPAEEWISRSDSEIIDA       LePDS X59948
398 FQKLEKLVGVPVINVHIWEDRKLKNTSDNLLFSRSPLLSVYADMSVTCKEYYDPNKSMLELVFAPAEEWVSRSDSEIIDA     CaPDS X68058

359                                                                                     CcPDS
460 TMKELEKLFPDEISADQSKAKILKYHVVKTPRSVYKTIPNCEPCRPLQRSPIEGFYLAGDYTKQKYLASMEGAVISGKFC    AtPDS TC261857
479 TMKELAKLFPDEISADQSKAKILKYHVVKTPRSVYKTVPCCEPCRPLQRSPIEGFYLAGDYTKQKYLASMEGAVISGKLC    LePDS X59948
478 TMKELAKLFPDEISADQSKAKILKYHVVKTPRSVYKTVPGCEPCRLLQRSPVEGFYLAGDYTKQKYLASMEGAVISGKLC    CaPDS X68058

359                                                                                     CcPDS
540 SQSIVQDYELIAASGFRKLSEAIVSSS.                                                         AtPDS TC261857
559 AQAIVQDYELLVGRSQKKLSEASVV                                                            LePDS X59948
558 AQAIVQDYELLVGRSQRKLAEISVV                                                            CaPDS X68058
```

FIG. 4B
(Page 2 of 2)

(Page 1 of 2)

```
171                                                                              CcZDS
378 VTELQDIELARQLKRAVGLDNLLYTPDADFSCFADLALASPADYYIEGQGTLLQCVLTPGDPYMRMPNIKIIEKVAMQVT AtZDS U38550
401 VTELQDLERSRQSKRATGLDNLLYTPDADFSCFADLALASPEDYYIEGQGSLLQCVLTPGDPYMPLPNDEIIRRVSKQVL CaZDS X89897
401 VTELQDLERSRQLKRAAGLDNLLYTPDADFSCFADLALASPDDYYIEGQGSLLQCVLTPGDPYMPISNDEIIKRVTKQVL LeZDS AF195507

171                                                                              CcZDS
458 ELFPSPRGLEVTCSSVVKIAQSLYREAPGKDPFRPDQKTPIKNFFLAGSYTKQDYIDSMEGATLSGRQASSYICDAGEEL AtZDS U38550
481 ALFPSSQGLEVTWSSVVKIGQSLYREGPGKDPFRPDQKTPVENFFLAGSYTKQDYIDSMEGATLSGRQASAYICDAGEQL CaZDS X89897
481 ALFPSSQGLEVTWSSVIKIGQSLYREGPGKDPFRPDQKTPVENFFLAGSYTKQDYIDSMEGATLSGRQASAYIQNVGEQL LeZDS AF195507

171                                                                              CcZDS
538 AEINKKLS-------SSATAVPDELSLV                                                    AtZDS U38550
561 LALRKKIAAAELNEISKGVSLSDELSLV                                                    CaZDS X89897
561 MALRKKITAAELNDISKGVSLSDELSLV                                                    LeZDS AF195507
```

FIG. 4C
(Page 2 of 2)

```
  1 MAISTSSVVEGISVSSSTSLKIRSFRNVPTVINSHTPSGIN-WVTSPHRHTATQEPLSRNSFRVQATVLQEDEQKVVVE  CcPTOX
  1 MA-AISGISSGTLTISR---------PLVTIRRSRAAVSYSSSHRILHHLPLSSRFLIRNNFRVQATILQDDEEKVVVE  AtPTOX AJ004881
  1 MAISISAMSERTSVSSS---------YSAHLCNSRNPFCIN-SLFSLRNSHRTFGESLSRKSSRVRATLLFENEEEVVE  CaPTOX AF177981
  1 MAISISAMSFGTSVSSYSCFRARSFEKSSVLCNSQNECRFN-SVEPIRKSDGASROSVSRKSCRVRATLLQENEEEVVE  LePTOX AF177980

80 ESFQSKSYPENGGG-NGEP-PDASSSSGLEKWVKIEQSINIFLTDSVIKILDTLYHDRHYARFFVLETIARVPYFAPM  CcPTOX
 71 ESFKAETSTGTEPLE---EDNMSSSTSAFEITAIIKLEQGVNMFLTDSVIKILDTLYRDRIYARFFVLETIARVPYFAPM  AtPTOX AJ004881
 71 KSFAPKSFPGNVGGGNNGEP-PINSSSNGLEKWVIKIEQSVNIFLTDSVIKILDTLYHDRHYARFFVLETIARVPYFAPI  CaPTOX AF177981
 80 KSFAPKSFPDVGGGSNGKP-PIDSSSNGLEKWVIKLEQSVNILTDSVIKILDTLYHRNYARFFVLETIARVPYFAPI   LePTOX AF177980

158 SVLHLYESFGWRRADLSEVHFAESWNEMHHLLIMEELGGNSWFDRFLAQHIAVFYYEMTVHMYLSPRMAYHFSECVE  CcPTOX
148 SVLHLYEIFGWRRADYLKVHFAESWNEMHHLLIMEELGGNSWFDRFLAQHIAFEYYMTVFLYILSPRMAYHFSECVE  AtPTOX AJ004881
150 SVLHLYESFGWRRADYLKVHFAESWNEMHHLLIMEELGGNAWFDRFLAQHIAVFYYEMTVSMYALSPRMAYHFSECVE  CaPTOX AF177981
159 SVLHLYESFGWRRADYMKVHFAESWNEMHHLLIMEELGGNAWFDRFLAQHIAIEYYYEMTVIMYALSPRMAYHFSECVE  LePTOX AF177980

238 SHAFETYDKFIKDQGEQLKRLPASNVAVKYYTEGNLYLFDEFQTARPETSRRPKIEMYDVELNIRDDEAEHCKTMKACQ  CcPTOX
228 SHAYETYDKFIKASGEELKNMPAFDIAVKYYTGGDLYLFDEFQTSRFPNTRREVIENLYDVEMNIRDDEAEHCKTMRACQ  AtPTOX AJ004881
230 HHAYETYDKFIKDQEAELKKLPAPKIAVSYYTGGDLYLFDEFQTSREPNTRRPKIDNLYDVEMNIRDDEAEHCKTMKACQ  CaPTOX AF177981
239 SHAYETYDKFIKDQGEELKNLPAPKIAVDYYTGGDLYLFDEFQTSREPNTRRPKIDNLYDVEMNIRDDEAEHCKTMKACQ  LePTOX AF177980

318 THGGLRSPHSYTDDA-CEEDAGYGIP-QADCFELTQ.                CcPTOX
309 TLGSLRSPHSILDDDTEEESGQVVPEEHCEGIVDCLKKSITS           AtPTOX AJ004881
310 THGSLRSPHTNFQDE-SEDIEGCSVP-QADCVGIVDCITKSVAEPNVGRR   CaPTOX AF177981
319 THGSLRSPHTLPQDI-SEDDIGCSVP-QADCIGIVDCIKKSVTITQVTKR   LePTOX AF177980
```

FIG. 4D

```
  1 MAA---GIAVAAGAQIVCFRVNSFITRKPTSLVADSLTISPLAQQESTTRHRRKPRLTVCFVLEDEELRAQLVTSEEEAR  CcBCH
  1 MAA---CISTIFVTLKPLNR-SSESANHPIST-----AVFPPSLREN---GFRRRKILTVCFVVEERKQSSPMD--DDNKP  AtBCHY NM_124636
  1 MAAAARISASSTSRIFYFRHSPFLGHKPTSITSHVSPISFTSLNLGPILESRRKPSFTVCFVLEDEKLKPQF---DDEAE  LeBCHY Y14809

79 EREKAMAKRISDARTAEKLARKRSERFTYLVAAVMSSFGITSMAVLAVYYREVWQMEGGEVPIYSEMFGTFALSVGAAVGM  CcBCH
 68 ESTTSSSEILMTSRILKKAEKKKSERFTYLIAAVMSSFGITSMPIMAVYYRFSWQMKGGEVGVLEMFGTFALSVGAAVGM  AtBCHY NM_124636
 78 DFEKKIEEQILATRLAEKLARKKSERFTYLVAPIMSSFGITSMAVMAVYYRFSWQMEGGEVPVTEMIGTFALSVGAAVGM  LeBCHY Y14809

159 EFWARWAHKALNHASLWHMHESHHRPREGPFELNDVFAIINAVPAIALLSYGFFHKGLIPGLCFGAGLGIIVFGMAYMFV  CcBCH
148 EFWARWAHRALNHDSLWMHESHHKPREGAFELNDVFAITNAVPAIGLIYYGFLNKGLVPGLCFGAGLGIIVFGMAYMFV  AtBCHY NM_124636
158 EFWARWAHKALNHASLWHMHESHHKPREGPFELNDVFAITNAVPAIALLNYGFFHKGLIAGLCFGAGLGITVFGMAYMFV  LeBCHY Y14809

239 HDGLVHKREPVGPIANVPYFRPVAAAHQLHHSDKFNGVPFGLFLGPKELEKVGGLEELEKEINRRIKIR-KGS          CcBCH
228 HDGLVHKREPVGPIANVPYLRKVAAAHQLHHTDKFKGVPYGLFLGPKEVBEVCGKEELEKEISRRIKLYNKGSSTS       AtBCHY NM_124636
236 HDGLVHKREPVGPMANVPYLRKVAAAHSLHHSEKFNGVPYGLFFGPKELEEVGGIEELEKEVIRRTRLS-KGS          LeBCHY Y14809
```

FIG. 4E

```
  1 ------------------------------------------------CVVDKEE-KIALKEDYIKAGGS CcLeCY
  1 MECFGERNVTATMAVFTCPRFTDCNIRHKFSLLKQFRFTNLSASSSLRQIKQSAHSLECVVDKEGISVADEEDYVKAGGS LsLeCY AF321538
  1 M-SHRGHVTATMAAFTCPRMFS-----------IFYT--------RQIKQNAAKGDLVVKQF---IEEEDYVKAGGS TeLeCY AF251016

22 ELLFVQMQQRKQMDQSKFSRKMPFISAG-----NSILDLVVIGCGPAGLALAAESAKLGLIVGLIGPDVPFTNNYGVWE CcLeCY
 81 ELFFVQMQRTKSMFSQSKLSEKLAQIPIG-----NCILDLVVIGCGPAGLALAAESAKLGLNVGLIGPDLPFTNNYGVWQ LsLeCY AF321538
 58 ELLFVQMQQNKSMDAQSSLSQKLPRVPIGGGGDSNCILDLVVIGCGPAGLALAESAKLGLNVELIGPDLPFTNNYGVWE TeLeCY AF251016

97 DEFKDLGLAGCIEHVWRDTVVYLDDNDPILIGRAYGRESRLLLHEELLRRCVESGVSYLSS.VERIVEAATGHSLIECEG CcLeCY
156 DEFIGLGLEGCIEHSWRDTLVYLDIADPIRIGRAYGRVHRDLLHEELLRRCVESGVSYLSSKVERITEAPNGYSLIECEG LsLeCY AF321538
138 DEFIGLGLEGCIEHVWRDTVVYLDDNDPILIGRAYGRVSRDLLHEELLRQVESGVSYLSSKVERITEAPNGLSLIECEG TeLeCY AF251016

177 SIVIPCRLATVASGAASGKLLQYELGGPRVSVQTAYGVEVEVENNPYDPNLMVFMDYRDYMRQKVESLEAEFPTFLYAMP CcLeCY
236 NITIPCRLATVASGAASGKLLEYELGGPRVCVQTAYGIEVEVENNPYDPDLMVFMDYRDFSKHKFESLEAKYPTFLYVMA LsLeCY AF321538
218 NITIPCRLATVASGAASGKLLQYELGGPRVCVQTAYGIEVEVESTPYDPSLMVFMDYRDYTKHKSQSLEACYPTFLYVMP TeLeCY AF251016

257 MSPTRVFFEETCLASKIAMPFELLKKKLMSRLDTLGVRIIKTYEEEWSYIPVGGSLPNTEQKNLAFGAAASMVHPATGYS CcLeCY
316 MSPTKIFFEETCLASKEAMPFNLLKGKLMSRLKAMGIRITRTYEEEWSYIPVGGSLPNTEQKNLAFGAAASMVHPATGYS LsLeCY AF321538
298 MSPTKVFFEETCLASKEAMPFELLKTKLMSRLKTMGIRITKTYEEEWSYIPVGGSLPNTEQKNLAFGAAASMVHPATGYS TeLeCY AF251016

337 VVRSLSEAPKYASAIANILKQGQRKLMTR-----NISHQARNTLWDQERKRQRAFFLEGLALILQLDIEGIRTFLQTFF CcLeCY
396 VVRSLSEAPNYAAVIAKTLROLQSKEMISLGRYT-NISKQAWETLWPLERKRQRAFFLFGLSIVIMDLEGTRTFFRTFF LsLeCY AF321538
378 VVRSLSEAPNYAAVIAKTLGKGNSKQMLDHGRYTTNISKQAWETLWPLERKRQRAFFLFGLALIVQMDIEGTRTFFRTFF TeLeCY AF251016

412 RLPNMWSQGFLGSSLSSTDLLLFAFYMFVIAPNDLRKCLIQHLLSDPTGATMVRIYLAI CcLeCY
475 RLPKMMWGFLGSSLSSTDLIIFALYMFVIAPHSLRMELVRHLLSDPTGATMVKAYLTI LsLeCY AF321538
458 RLPIMMWGFLGSSLSSTDLIIFAFYMFIIAPHSLRMGLVRHLLSDPTGGIMLKAYLTI TeLeCY AF251016
```

FIG. 4F

FIG. 4G
(Page 1 of 2)

FIG. 4G
(Page 2 of 2)

```
  1 MASFLSAEHSADEG------IREYIRSQHRIGRCSNGGARPQNAIFSVKMWSKRWGSRIIQLCRAPRISLSIGSKCT  CcVDE
  1 MAVPIHCFTSPCHDR------IRFFSSDD--CIGRLGITRKRINGTFLLKILPPICSADLRITGGRSSRPLSAFRSG--  AtVDE AY063067
  1 MEARHEWSALSPPAGGGAMGGVRYHRCCP----PRAYLARKGDHLPHHARLSARCSEIKAHIVLQGSDALSSIRKWSR  OsVDE AF411133
  1 MPLAPHSNELANHET------IKYNVGSKLPCHKRESAWEDYEGSIVVAKICSSRRIPRYFR--KSPRLCCGLDSRGL  NtVDE U34817

74 KLELNG--------------------------------------------------------ICRIE  CcVDE
 70 --FSKGIFDIVFLPSKNE---------LKELIAPLLLKLVG------VLACAILIVPSADAVDALKTCACLLKGCRIE  AtVDE AY063067
 77 SHLVTMTG---------------------------------------LVACAVLWPSADAVDALKTCTCLLKECRIE  OsVDE AF411133
 72 QLFSHGKHNLSPAHSINQNVPKGNSGCKFPKDWALMWEKWCQFAKTAINAIFILSVASKADAVDALKTCTCLLKECRLE  NtVDE U34817

85 LAKCIANPSCAANVACLQTCNNRPDETECQIKCGDLFQNSVVDEFNECAVSRKKCVPRKSDVGEFPAPDEAVLVKNFDIK  CcVDE
131 LAKCIANPACAANVACLQTCNNRPDETECQIKCGDLFENSVVDEFNECAVSRKKCVPRKSDLGEFPAPDPSVLVQNFNIS  AtVDE AY063067
116 LAKCIANPSCAANVACLNTCNNRPDETECQIKCGDLFENWVDEFNECAVSRKKCVPQKSDVGEFEVPDPSALVQNENMA  OsVDE AF411133
152 LAKCISNPACAANVACLQTCNNRPDETECQIKCGDLFENSVVDEFNECAVSRKKCVPRKSDVGEFPVPDPSVLVQKFDAK  NtVDE U34817

165 DFSGKWYISSGLNPTFDTFDCQLHEFHTE-SGKLVGNLIWRIRTPITGFFTRSALQREVQDPKYPGILYNHDNEYLHYQD  CcVDE
211 DENGKWYITSGLNPTFDAFDCQLHEFHTEGDNKLVGNISWRIKTLDSGFFTRSAVQKFVQDPKQPGVLYNHDNEYLHYQD  AtVDE AY063067
196 DENGKWYISSGLNPTFDTFDCQLHEFRVE-GDKLIANLIWRIRTPDSGFFTRIPICREVQDPAQPAILYNHDNEILHYQD  OsVDE AF411133
232 DFSGKWFITRGLNPTFDAFDCQLHEFHTE-ENKLVGNLSWRIRTPIGGFFTRSAVQKFVQDPKYPGILYNHDNEYLIYQD  NtVDE U34817

244 DWYILSSKIENKPDDYAFVYYRGRNDAWDGYGGAVVYTRSAVLPESIVPELQRAAKSIGRDFSKFIRTDNTCGPEPPLVE  CcVDE
291 DWYILSSKIENKPDDYIFVYYRGRNDAWDGYGGAVVYTRSSVLPNSTIPELEKAAKSIGRDFSTFIRTDNTCGPEPPALVE  AtVDE AY063067
275 DWYIISSKVENKPDDYIFVYYRGRNDAWDGYGGAVLYTRSKVPESIVPELERAAKSVGRDFSTFIRTDNTCGPEPPLVE  OsVDE AF411133
311 DWYILSSKVENSPDYIFVYYRGRNDAWDGYGGSVLYTRSAVLPESIIPELCTAAQKVGRDFNIFIKTDNTCGPEPPPLVE  NtVDE U34817
```

FIG. 4H
(Page 1 of 2)

```
324 RLEKTVEEGERTIVREVEEIEGEIEGEVEKVKDTEMTLFERLTEGFKELKKDEEFFLRELSKEEIDVLIALKMEASEVEK  CcVDE
371 RIEKTVEEGERIIVKEVEEIEEEVEKEVEKVGRTEMTLFQRIAEGFNELKQDEENFVRELSKEEMEFLDEIKMEASEVEK  AtVDE AY063067
355 RIEKTVEQGEKTIIREVQEIEGEIEGEVKELEEEEVTLFKRLTDGLMEVKQDLMNEFQGLSKEENELLIQMMEATEVEK  OsVDE AF411133
391 RLEKKVEEGERTIIKEVEEIE----EEVEKVRIKEVTLISKLFEGFKELQRDEENELRELSKEEMDVLIGLKMEATEVEK  NtVDE U34817

404 LFGRSLPIRKLR   CcVDE
451 LFGKALPIRAVR   AtVDE AY063067
435 VFSRALPIRKLR   OsVDE AF411133
467 LFGRALPIRKLR   NtVDE U34817
```

FIG. 4H
(Page 2 of 2)

FIG. 4I
(Page 1 of 3)

```
305 VRITPSGDLKTVERYSENGQIKSTMIAHPKLDPVIGELEALSYDVIQKPYLKYERFSPAGEKSKDIEIEVPEPTMAHDFA  CcNCED3
270 VQITPNGDLKTVGREDEDGQIESTMIAHPKVDEESGELEALSYDWSKPYLKYERFSPDCIKSPDVEIQLDQPTMMHDFA  AtNCED3  NM112304
260 VRVTDNGDLIITGREDEDGQISSAMIAHPKIDPVTKELEALSYDWKKPYLKYEKFSPEGEKSPDVEIPLASPTMMHDFA  AtNCED5  NM102749
275 VKVTPTGDLKIEGREDEDGQVSTMIAHPKLDPVSGELEALSYDVIQKPYLKYERFSKNGEKSNDVEIEVEDPTMMHDFA  LeNCED1  CAD30202
273 VKVTPTGDLKIEGREDEDGQIKSTMIAHPKLIPVSGELEALSYDVIQKPYLKYERFSKNGEKSNDVEIEVEDPTMMHDFA  StNCED1  AAT75151
281 IRVTPSGDLETVGRYDEDGQIRSTMIAHPKVDPVSGEMEALSYDWQKPYLKYERFSPKGIKSPDVEIPLAEPTMMHDFA  VvNCED1  AAR11193

365 ITENFWIPDQQWFKMSEMIRGGSPVVYDKEKVSRFGVLDKYADSSAIKWVEVPDCFCFHLMNAWEEPETIEIWIGS  CcNCED3
350 ITENFWVPDQQWFKLPEMIRGGSPVVYDKNKVARFGILDKYAEISSNIKNIDAPDCFCFHLMNAWEEPETDEVWIGS  AtNCED3  NM112304
340 ITENFWIPDQQWFKLSDMEICKSPVMYTLGERISRFGILPRNAKIASEMWVESFETFCFHLMNAWESPETDEVWIGS  AtNCED5  NM102749
355 ITENFWIPDQQWFKMSEMIRGGSPVVYDKNKVSRFGILDKYAKDGSDIKWVEVPDCFCFHLMNAWEEAETDEIWIGS  LeNCED1  CAD30202
353 ITEKFVIIPDQQWFKMSEMIRGGSPVVYDKNKVSRFGILDKYAKDGSDIKWVEVPDCFCFHLMNAWEEPETDEIWIGS  StNCED1  AAT75151
361 ITEREWVENQQWFKLQEMISGGSPVVYDKNKYSREGVLDKNATDASGMLAIEAPDCFCFHLMNAWEEPETDEVWIGS  VvNCED1  AAR11193

465 CMTPPISIFNECDEGLKSVLSEIRLNLKTGKSTRRAIISNPEIQVNLEAGMVNRNKLGRKTRYAYLAIAEPWEKVSGFAK  CcNCED3
430 CMTPPISIFNESDENLKSVLSEIRLNLKTGHSTRREIISNEDQVNLEAGMVNRNYLGRKTKFAYLAIAEPWEKVSGFAK  AtNCED3  NM112304
420 CMTPADSIFNECDEQINSVLSEIRLNLKTGKSTRRIILP-GSVQMNLEAGMVNRNILGRKTRYAYLAIAEPWEKVSGFAK  AtNCED5  NM102749
435 CMTPPISIFNECDEGLKSVLSEIRLNLKTGKSTRKSIIENPDEQVNLEAGMVNRNKLGRKTEYAYLAIAEPWEKVSGFAK  LeNCED1  CAD30202
433 CMTPPISIFNECDEGLKSVLSEIRLNLKTGKSTRKAIIENPDEQVNLEAGMVNRNKLGRKTQYAYLAIAEPWEKVSGFAK  StNCED1  AAT75151
441 CMTPPISIFNECDEGLKSVLSEIRLNLKTGKSTRRFILP-ESEQVNLEAGMVNRNLGRKTQFAYLAVPEPWEKVSGFAK  VvNCED1  AAR11193
```

FIG. 4I
(Page 2 of 3)

```
545 VDLFTGEVRKFTYGLEKYGGEPLFLPRDPNCFAEDIGYILAFVHDEKEWKSELFIVNAMTLELEASVQLPSRVPYGFHGT  CcNCED3
510 VDITTGEVRPHLYGDNYGGEPLFLPGE--GEEDIGYILCFVHDEKTWKSELQIVNAVSIEVEATVKLPSRVPYGFHGT  AtNCED3 NM112304
499 VDISTGEVKNHFYGGRKYGGEPIFFLPRGLESLGEDIGYIMSEVHDEESAESELHIVNAVTLELEATVKLPSRVPYGFHGT  AtNCED5 NM102749
515 VALFTGEVEKFTYGDNKYGGEPLFLPRDPNSKEEDIGYILAFVHDEKEWKSELQIVNAVSIKLEATVKLPSRVPYGFHGT  LeNCED1 CAD30202
513 VDLFTGEVEKFTYGDNKYGGEPLFLPRDPNSKEEDIGYILAFVHDEKEWNSELQIVNAMTIKLEATVKLPSRVPYGFHGT  StNCED1 AAT75151
520 VDISTGVVSAYTYGEQFYGGEPLFLPRDPNSGREDIGYILAFVHDEKTWKSELQIVNATNLQLEASVKLPSRVPYGFHGT  VvNCED1 AAR11193

625 FISAKDIASQA  CcNCED3
588 FIGADDLAKVV  AtNCED3 NM112304
579 FVNSAEMLNQA  AtNCED5 NM102749
595 FINANDLANQA  LeNCED1 CAD30202
593 FINANDLANQA  StNCED1 AAT75151
600 FISSKELEKQA  VvNCED1 AAR11193
```

FIG. 4I
(Page 3 of 3)

FIG. 4J
(Page 1 of 2)

```
320 VLPRYSKNDALIRWFELPNCFIFHNANAWEEGDEVILITCRLQNPDLDMVSGIVKKKLEN-ESNELYEMRFNLKTGLASQ  CcCCD1
318 VLPRYAKSEALIRWFELPNCFIFHNANAWEEGDEVVLITCRLPHPDLDMVNGEVKENLEN-ESNELYEMRFNMKSGAASQ  PhCCD1 AY576003
316 VLPRYAKNESLIKWFELPNCFIFHNANAWEEGDDVVLITSRLQNPDLDAIKGTEKEEQRDGEINELYEMRFNMKNGVASQ  LeCCD1B AY576002
317 VLPRYANNEALIRWFELPNCFIFHNANAWEEGDEVVLITCRLVNPDLDMVNGAVKEKLEN-EQNELYEMRFNMKSGAASQ  LeCCD1A AY576001
313 VLPRYAKDLMIRWFELPNCFIFHNANAWEEDDEVVLITCRLENPDLDMVSGKVKEKLEN-EGNELYEMRFNMKTGSASQ  AtCCD1 AJ005813

399 KKLSESAVDFPRVNESYTGRKQQYVYGTIIDSIAKVTGIAKFDLHAEPETGKTKIEVGGNVQCVFDLGPGREGSEAIFVP  CcCCD1
397 KKLSESGVDFPRINENYTGRKQRYVYGTILNSIAKVTGIIKFDLHAEPETGKKQLEVGGNVQGIFDLGPGRFGSEAVFVP  PhCCD1 AY576003
396 KKLSEAAVDFPRINENYTGGKQRYVYGTILNVAQITGVVKFDLHAEPETGKTKLEVGGNVPGIFDLGPGRFGSEAIFVP  LeCCD1B AY576002
396 KKLSESAVDFPRINENYTGRKQRYVYGTILNSIAKVTGVIKFDLHAEPETGKSQLEVGGNVQGIFDLGPGREGSEAVFVP  LeCCD1A AY576001
392 KKLSASAVDFPRINEGYTGRKQRYVYGTILDSIAKVTGIIKFDLHAEAETGKRMLEVGGNIKGIYDLGEGRYGSEAIYVP  AtCCD1 AJ005813

479 RQPGITSEEDDGYLIFFVHDESTGKSAVNVIDAKTMSADPVAVVELENRVPYGFHAFFVTEEQLEEQAKL  CcCCD1
477 SQPGTECEEDDGYLIFFVHDENTGKSAVNVIDAKTMSAEPVAVVELPKRVPYGFHAFFVTEEQIQEQAKL  PhCCD1 AY576003
476 RQPGTECEEDDGYLILFVHDENTGKSSVNVIDAKTMSAEPVAVVELPKRVPEGFHAFFVTEEQIQEQAKM  LeCCD1B AY576002
476 SRPGTEREEDDGYLIFFVHDENTGKSAVNVIDAKTMSAEPVAVVELPKRVPYGFHAFFVTEEQIQEQAKL  LeCCD1A AY576001
472 RET---AEEDDGYLIFFVHDENTGKSQVIVIDAKTMSAEPVAVVELHRVPYGFHAIFVTEEQLQEQTLI  AtCCD1 AJ005813
```

FIG. 4J
(Page 2 of 2)

```
  1 MASITSFNQFSYTVKSKTFCHPQFGTRVSNSAVNFTDEGLSKP-DSSSIKESSKFRPSEVVLVAAG---DDYGPE-EE CcFIB1
  1 MPTVQLSTQFSCQIRVSISPNSK---SISKFEFIVFVISIIHRPMISTGGIAVSP--RRVFKVRATDTG---EIS----- AtFIB1b NM-118350
  1 MPTVPLFTQFPCKTINPSSSNIK---HQSKSPIILPINSINRR---SPIGVSVH---RPDFKIFATEID--DEWGDGVE AtFIB1a NM-116640
  1 MASISSLNQIPCKTLQITSQYSK----ISSLHLTSPNEPSKTE-LHKSISIKEFINPKPKFTAQAINYDKEDEWGPE-LE CaFIB X77290
  1 MASISSLNQIPQRTLQITSQYSRPTSKISTLPISSTNEPSKTE-LHRAISVKEFTYEKPKFTAQAINYDKEDEWGPE-VE LeFIB SGN-U213598

76 ----AAGVAVAEEEPPKEPREIDILKRFLVDSFYGTDRGLNASSETRAEVVELITQLEAKNPTPAPTEALTLLNGKWILA CcFIB1
 68 ------SALIAEEEAIEDVEETERLKRSLVDSIYGTDRGLSASSETRAEICLITQLESKNPTPAPTEAILLLNGKWILA AtFIB1b NM-118350
 70 RVFASSSTVSVDLKAIESVEETERLKRSLADSIYGTDRGLSVSSETRAEISELITQLESKNPTPAPEATLLLNGKWILA AtFIB1a NM-116640
 75 QI-NPGGVAVVEEPPKEPSEVEKLKKQLIDSFYGTIRGLSASSETRAEIVELITQLESKNPTPAPTEAISLLNGKWILA CaFIB X77290
 79 KI-SPGGVAVVEEPPKEPSEIELLKKQLADSFYGTIRGLSASSETRAEIVELITQLESKNPPAPTEALTLLNGKWILA LeFIB SGN-U213598

152 YTSFIGLFPLLSRGILPLVKVEEISQTIDSEASVEAVWKEAGPLATTSIITNAKFEVRSPKRVQIKFEEGVIGTPQLTD CcFIB1
142 YTSFVNLFPLLSRGIVPLIKVEEISQTIDSDNFTVQNSVRFAGPLSTTSISTNAKFEIRSPKRVQIKFEQGVIGTPQLTD AtFIB1b NM-118350
150 YTSFVGLFPLLSRRIEPLVKVEEISQTIDSDSFTVQNSVEFAGPFSTTSISTNAKFEIRSPKRVQIKFEQGVIGTPQLTD AtFIB1a NM-116640
154 YTSFSGLFPLLARGNLLPRRVEEISQTIDAETITVQNSVVFAGPLSTTSISTNAKFEVRSPKRLQINEEGIIGTPQLTD CaFIB X77290
158 YTSFSGLFPLLSRGNLLMFVEEISQTIDSESEFTVQNSVVFAGPLATTSISTNAKFEVRSPKRVQIKFEEGIIGTPQLTD LeFIB SGN-U213598

232 SIELPESVELLGQKIDLNPVKGLLTSVQDTASSVAKSISSRPPLKFSLSNRNAESWLLTTYLDDELRISRGDGGSIFVLI CcFIB1
222 SIELPENVEVLGQKIDLNPIRGLLTSVQDTASSVARTISSQPPLKFSLPADNAQSWLLTTYLDKDIRISRGDGGSVFVLI AtFIB1b NM-118350
230 SIELPESVEVLGQKIDLNPIKGLLTSVQDTASSVARTISNQPPLKFSLPSDNIQSWLLTTYLIKELRISRGDGGSVVLI AtFIB1a NM-116640
234 SIELPENVEFLGQKIDISPFKGLITSVQDTAISVAKSISSQPPIKFPISNSYAQSWLLTTYLDAELRISRGDAGSIFVLI CaFIB X77290
238 SIVLPENVEELGQKIDISPEKGLITSVQDTASSVAKSISSQPPIKFPISNNNAQSWLLTTYLDDELRISRGDAGSVFVLI LeFIB SGN-U213598

312 KEGSPLLKP CcFIB1
302 KEGSPLLNP AtFIB1b NM-118350
310 KEGSSLINP AtFIB1a NM-116640
314 KEGSPLLKP CaFIB X77290
318 KEGSPLLKP LeFIB SGN-U213598
```

FIG. 4K

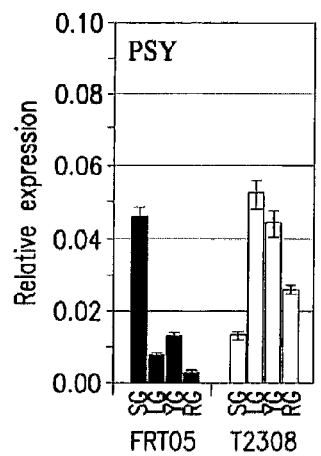
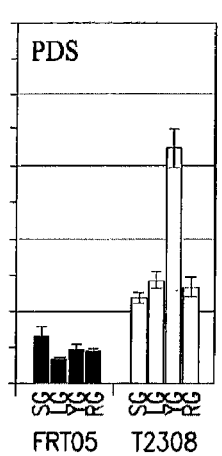
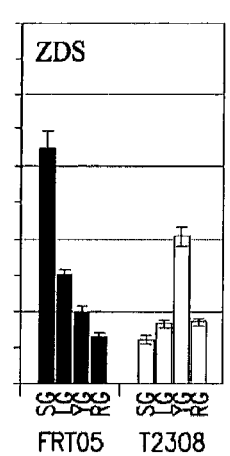
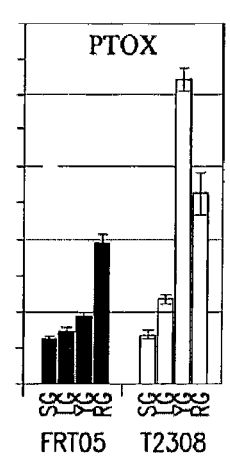
FIG. 5A  FIG. 5B  FIG. 5C  FIG. 5D
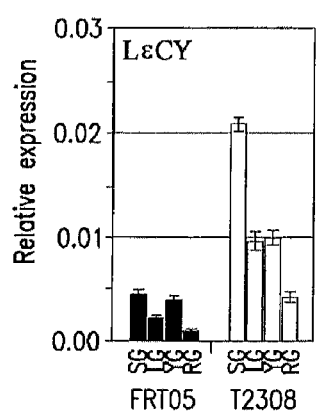
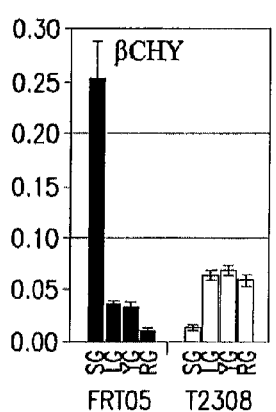
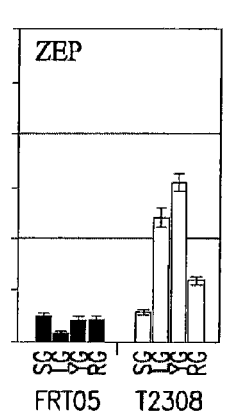
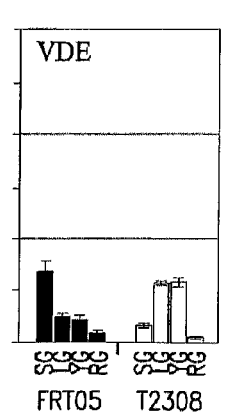
FIG. 5E  FIG. 5F  FIG. 5G  FIG. 5H

SEQUENCE LISTING

```
<160> NUMBER OF SEQ ID NOS: 93

<210> SEQ ID NO 1
<211> LENGTH: 1320
<212> TYPE: DNA
<213> ORGANISM: Coffea canephora

<400> SEQUENCE: 1
atgtctgttg ctttgctatg ggttgtttta cctatctcag aggtcacgaa cagcattgca      60
ttcctggaac cggtacggga aggaagccgg cttcttgatt cgtccaggtt cgtgggtcgg     120
ggtaaaaact gcttgtgcaa tggcagactt gagaaaggca agcaacaaag gtggaattct     180
ggttatctta atggagattc gagaaactgt tgcttgggag gctctaggtt gaagaaccga     240
ggcaaatttt ctgtgattcc caatgtagtg gttagcccag ctggagaaat tgccatgtct     300
tcagagcaaa aggtttatga tgtggttttg aagcaggcgg ccttggttaa tagacaattg     360
agatctcgag aagattggga cgtgaagccc gatattgttc tcccaggaaa tttaaacata     420
ttaagtgaag cttatgatcg ctgcggtgaa gtatgtgctg aatatgccca gactttttac     480
ttgggaacaa tgctaatgac acctgagaga agaagagcta tttgggcgat atatgtttgg     540
tgcaggagaa cagatgagct cgttgatggg cctaatgcat cacatataac tccaactgca     600
ttggataggt gggaagcgcg attggaagat gtctttagag gtcatccttt tgatatgctt     660
gatgctgctc tttcagatac tgtttccaag tttccagttg acatccagcc attcagagac     720
```

| | |
|---|---|
| atgattgaag gaatgagaat ggacctaaag aagtcaagat acaaaaactt tgatgagcta | 780 |
| tacctctact gttactatgt ggccggtacc gttggattga tgagtgtccc agttatgggc | 840 |
| attgcaccag aatcaaaagc aacagtagaa agtgtctata atgcagccct ggcattaggg | 900 |
| attgctaacc agctgactaa catactaagg gatgttggag aagatgctac aagaggaagg | 960 |
| atctacctac cccaagatga attagcacag gcagggcttt cagatgagga tatatttgct | 1020 |
| ggaaaggtca ctgaccaatg gaggaatttc atgaagcagc aaatgaaaag agcaaggaag | 1080 |
| ttctttgatg aggcagagaa aggagtgacc gagctcaact ctgctagcag atggcctgta | 1140 |
| tgggcatcgc tattgctgta tcgtcaaata ctcgacgaga ttgaagccaa tgactacaac | 1200 |
| aattttgaca ggagagctta tgttagcaaa ccgaagaagt tacttgctct gccaatggca | 1260 |
| tatgcaaagt ctcttgtacc tccaagaaca tcatctccgc tagcaaaagg catgagctga | 1320 |

<210> SEQ ID NO 2
<211> LENGTH: 1077
<212> TYPE: DNA
<213> ORGANISM: Coffea canephora
<220> FEATURE:
<221> NAME/KEY: misc_feature
<222> LOCATION: (42)..(43)
<223> OTHER INFORMATION: Unknown nucleotide (N)
<220> FEATURE:
<221> NAME/KEY: misc_feature
<222> LOCATION: (825)..(827)
<223> OTHER INFORMATION: Unknown nucleotide (N)

<400> SEQUENCE: 2

| | |
|---|---|
| attgactatc caaggccaga gcttgaaaat gccgtcaact atttggaagc tgcttatta | 60 |
| tcatcaacat tccgtacttc tcctcatcca aataaaccat tagaggtggt gatcgccggt | 120 |
| gcaggtttgg ctggtttgtc tactgcaaag tatttggccg atgcaggtca taaacctata | 180 |
| gtgttggaag ctagggatgt tctgggagga aaggttgctg catggaaaga tgatgatgga | 240 |
| gactggtatg agactggcct gcacgtattc tttggggctt acccaaatat gcagaacctg | 300 |
| tttggagaac taggaattaa tgatcggttg cagtggaagg agcattcaat gatatttgca | 360 |
| atgccaaata gcctggagag ttcagtcga tttgatttc ctgaggtgct accagcacca | 420 |
| ttaaatggaa tatgggccat cttgaagaat aatgacatgc ttacttggcc agagaaagtc | 480 |
| aaatttgcaa ttggactctt gccagcaatt ctgggtggac aatcttatgt tgaggcacaa | 540 |
| gatggtataa ctgtcaaaga ctggatgaga aagcaaggca taccagatcg ggtgactgat | 600 |
| gaagtattct ttgccatgtc aaaggcactg aacttcataa atccagatga actttcaatg | 660 |
| cagtgcattt taatagcttt gaaccgattt cttcaggaga agcatggatc caaaatggca | 720 |
| ttttagatg gtaaccctcc agagagactt tgcatgccga ttgttgagca cattgagtca | 780 |
| cgaggaggca gagtacacct taactcaaga attcagaaaa ttgagctcaa tgatgccgga | 840 |
| agtgttgaaa acttcttgct gagtaatgga actgtgatta gaggagatgc ttatgtattt | 900 |
| gccactccag ttgatatcct gaagcttctt ttgcctgagg attggaaaga gatgccatac | 960 |
| ttcagaaagt tggagaaatt agttggagtt cctgttataa atgtgcacat atggtttgac | 1020 |
| aggaagctca ggaacacata cgatcatctt cttttttagca gaagtccact tcttagt | 1077 |

<210> SEQ ID NO 3
<211> LENGTH: 1056
<212> TYPE: DNA
<213> ORGANISM: Coffea canephora

```
<400> SEQUENCE: 3
atggcgacat caacgtcttc tgtggtgttt ggaatctctg tatcatcttc tacttctttg      60
aaaataagga gttttagaaa tgtgcccact gtgttaaatt ctcatacccc ttctggttta     120
aatgttgtta cttcacctca tcataggcat actgctactc aacgtccact ctccaggaac     180
tcgtttagag tccaagcaac tgtgttgcaa gaggatgaac agaaagtggt ggtggaagaa     240
tcatttcaat cgaaaagtta ccctgaaaat ggaggaggag gaaacggaga gccacctgat     300
gcttcatcct ctagtggttt ggagaaatgg gttgtaaaga ttgagcaatc cataaatatc     360
tttctcacgg actctgtgat aaagatactt gacactttgt atcatgatcg acattacgcg     420
aggttttttg ttctggaaac tattgcaagg gttccctact ttgctttcat gtctgttctg     480
cacttgtatg agagttttgg ttggtggaga agggcagatt tatctgaagt tcattttgca     540
gagagctgga atgagatgca ccatctgctc ataatggaag aactgggtgg aaattcttgg     600
tggtttgacc ggtttctagc tcaacatatt gcagtctttt actactttat gacagtcttt     660
atgtatatgc tgagcccaag gatggcgtat catttttctg agtgtgtgga aagtcatgcg     720
tttgaaacct atgacaaatt tatcaaggat caaggagagc aattgaagaa actaccagca     780
tcaaatgttg ctgtgaagta ttacacagag gggaacttgt acttgtttga tgaatttcaa     840
accgcaagac cgcctacttc tcgaaggcca aagatagaga acatgtatga tgtgtttctg     900
aacatcagag acgatgaagc cgagcattgc aagactatga aggcctgcca aactcatggg     960
ggccttcgct ctcctcactc atatacagat gatgcgtgtg aagaagatgc aggttatggc    1020
ctaccccagg ctgattgtga agagctgacc cagtag                              1056

<210> SEQ ID NO 4
<211> LENGTH: 933
<212> TYPE: DNA
<213> ORGANISM: Coffea canephora

<400> SEQUENCE: 4
atggctgccg gaattgccgt cgcagccggc gcccagacag tctgtttccg ggtcaactca     60
tttctaaccc gaaaacccac ctccctagtc gcagatagcc tgactctttc ccctttagcc     120
cagcaattca gcacaactcg gaggcatcga aggaagccca ggttgacggt tgttttgtg      180 ctggaggatg aggaattgaa agcccagttg gtgacaagcg aggaggaagc gcgagagcgc     240
gagaaagcga tggcgaagcg gatctctgat gcaagaacgg cggagaaact agccaggaag     300
agatcggaga ggttcactta tctcgttgcg gccgtcatgt ctagcttcgg aattacttcc     360
atggcagttc tggctgtttta ctacagattt gtttggcaaa tggagggcgg agaggtgcct     420
tattcggaaa tgtttggcac atttgctctt tcagttggtg cagctgtggg aatggaattc     480
tgggcgagat gggctcacaa agcgctgtgg cacgcttcgt tatggcacat gcacgagtca     540
caccatagac caagagaagg gccctttcgag cttaacgacg ttttcgccat aatcaacgcc    600
gtccctgcca tagccctcct ttcttatggc ttcttccaca agggcctcat tcctggcctc     660
tgcttcggtg ccggccttgg gattatagtg tttggcatgg cgtacatgtt cgtccacgat     720
ggtctggtgc acaagagatt tccggttggt cccattgcaa atgttcctta cttcagaaga     780
gttgcagctg cacatcagct gcatcattcg gacaagttca acggcgtccc atttgggttg     840
ttcttagggc caaaggaact tgaaaaagta ggggggcttg aagagctgga aaggaaatc     900 aaccggagaa tcaagttgcg taagggttca taa                                 933
```

<210> SEQ ID NO 5
<211> LENGTH: 1413
<212> TYPE: DNA
<213> ORGANISM: Coffea canephora

<400> SEQUENCE: 5

| | | | | | |
|---|---|---|---|---|---|
| tgtgtggttg | ataaagaaga | aaagtttgct | gatcaagaag | attacatcaa | ggctggtggg | 60 |
| tctgagctcc | tctacgttca | aatgcaacag | agaaagcaaa | tggatcaaca | gtctaaattt | 120 |
| tcggataaga | tgccggaaat | atcagccggt | aatagcatac | tggacttggt | ggtgatcggc | 180 |
| tgtggtcctg | ctggacttgc | ccttgccgca | gagtcagcta | agctaggtct | gacggttggg | 240 |
| ctaattggcc | cagatgttcc | tttcacaaat | aattatggtg | tgtgggagga | tgaatttaaa | 300 |
| gatcttgggc | ttgctggatg | cattgagcat | gtttggaggg | acacagtcgt | atatcttgat | 360 |
| gataatgatc | ccatcctcat | cggtcgtgct | tatgacgat | ttagtcgcca | tttgctccat | 420 |
| gaggagctgc | taagaaggtg | tgtcgagtca | ggtgtgtcat | atcttagctc | ataggtggaa | 480 |
| aggattgtcg | aagctgctac | cggtcacagt | cttgtagagt | gtgaaggcag | cattgtgatt | 540 |
| ccctgcaggc | ttgctactgt | tgcatctgga | gcagcctctg | aaaactctt | gcagtatgaa | 600 |
| ctgggaggtc | ctagagtttc | tgttcaaaca | gcttatggtg | tggaggttga | ggtggaaaat | 660 |
| aatccatatg | accccaatct | gatggtcttc | atggattata | gagactacat | gaggggcaaa | 720 |
| gttgaatctc | tagaagcaga | atttcccaca | tttcttatg | ctatgcccat | gtctccaaca | 780 |
| agagttttct | tgaggaaac | ctgtttggct | tcaaagatg | ccatgccatt | tgaactatta | 840 |
| aagaaaaaac | tgatgtcaag | actggatact | ctaggagttc | gaattatcaa | aacttatgaa | 900 |
| gaggaatggt | cttatatacc | agtcggtgga | tctttgccaa | atacagagca | aaaaaatctt | 960 |
| gcatttggtg | ctgctgccag | catggtacat | cctgccacag | gctactcagt | tgttagatca | 1020 |
| ttgtcagagg | ccccaaaata | tgcttctgca | atagcaaata | tcttgaaaca | aggtcaagct | 1080 |
| aaggacatga | tgacccgaaa | catatccgct | caagcttgga | acactctttg | gccgcaagag | 1140 |
| aggaaacgac | agagagcatt | cttccttttt | ggattggcac | ttattttgca | gctggatatt | 1200 |
| gaggggataa | ggacgttttt | ccagactttc | ttccgtttgc | caaactggat | gtcacaggga | 1260 |
| tttcttggtt | ctagtctttc | ctcaacagac | ctcctgttat | ttgcctttta | tatgttcgta | 1320 |
| atagcaccaa | atgacttaag | aaagtgcctt | atccagcatc | ttttgtctga | tccaaccggt | 1380 |
| gcaaccatgg | taagaacata | tctcgctata | tag | | | 1413 |

<210> SEQ ID NO 6
<211> LENGTH: 1032
<212> TYPE: DNA
<213> ORGANISM: Coffea canephora

<400> SEQUENCE: 6

| | | | | | |
|---|---|---|---|---|---|
| ggtaagaagg | aaaggttgct | taaaatcttt | gatggttggt | gtgataaagt | gatggaacta | 60 |
| ttgctggcca | cagacgaaga | tgcaattctt | cgtcgtgata | tttatgacag | aacaccatca | 120 |
| tttagctggg | aaggggtcg | tgtgacttta | cttggggact | caattcatgc | aatgcaacct | 180 |
| aatttgggac | aaggagggtg | catggcaatt | gaggacagct | atcaattggc | tttggagctt | 240 |
| gataaagctt | gggaacaaag | cataaaatcg | gggagcccaa | tggatgttgt | ctctgcttta | 300 |
| aagagctatg | agagtgctag | aaaactacga | gttgctatca | ttcatggatt | ggcaagattg | 360 |
| gctgcaatca | tggcatcaac | ttataagcca | tatttgggtg | taggattagg | gccactatcg | 420 |
| ttcttaacaa | aatttaggat | accgcatcca | ggaagagttg | gtgggagaat | atttatcgac | 480 |

-continued

| | |
|---|---|
| attggaatgc cattaatgct aagttgggtc ctaggtggca atggctcaaa acttgaaggc | 540 |
| agaccattgc attgcagact tactgataaa gcaagtgatc agctacaaaa atggtttcaa | 600 |
| gatgatgatt cttttggagcg tgctctgaac ggagagtggt tcctgtttcc cattggacaa | 660 |
| gccaatcctg atccagtagc tattttctta ggcagagatg aagaatat ctgcacaata | 720 |
| gggagtgcat cacaccctga tattcttgga gcatccataa ttattaattc accccaggtc | 780 |
| tccaagctgc atgctcaaat aagctacaaa gatggattat ttttcttgac cgatttacaa | 840 |
| agtgaacatg gcacctggat tacagacaac gatggtaggc gctaccggct gcctcctaac | 900 |
| tcgccagctc gttttcatcc atatgacatc attgagtttg gttctgacaa ggctgcattc | 960 |
| cgggtaaagg tcacgaacca gccaccgttc tcgggaaaga agcgagagac taaagttctt | 1020 |
| tcagctgtat ga | 1032 |

<210> SEQ ID NO 7
<211> LENGTH: 1449
<212> TYPE: DNA
<213> ORGANISM: Coffea canephora

<400> SEQUENCE: 7

| | |
|---|---|
| atggcttctg ctttgcattc agcttttcac tcaaatgatg agggcattcg ttttttatat | 60 |
| agatcgcaac accgtattgg tggaagatgt agcaatggtg gtgctcgtcc tcaaaatgct | 120 |
| ttatttagcg tgaaaatgtg gtccaaaaga tgggatcac gatatattca attgcaaaga | 180 |
| gctcctagaa taagtttgag cttgggttca aaatgcacaa gactgttctt gaatggaatc | 240 |
| aaggtttcaa atcataacac ctgcagaaca atgcctgagg tgaaagaggg aattgggatt | 300 |
| ttgaaggaag cattgttgat tacttggaaa gaatggagtc agtccactaa agtggctgtc | 360 |
| ttgttgatat ttgccttgtt gattattccg aaggctgacg ccgtagatgc tctaaaaact | 420 |
| tgtacttgct tattgaagga atgtaggata gagcttgcaa agtgtattgc aaatccatca | 480 |
| tgtgcagcta atgttgcttg tcttcagacc tgtaacaata gacctgatga gactgaatgc | 540 |
| cagatcaaat gtggtgattt atttcagaac agtgtagttg acgaatttaa tgagtgtgca | 600 |
| gtctcacgaa agaaatgtgt accccgaaaa tcagatgtgg gtgaatttcc agctcctgat | 660 |
| cctgctgttc tagttaagaa cttttgacatt aaagatttta gtgggaagtg gtatataagt | 720 |
| agtggcttaa atcccacttt tgatacccttt gattgccaac tacatgagtt tcacacagaa | 780 |
| tctgggaagc ttgttggaaa tttgacatgg cgaatacgaa ctccagacac tggattcttc | 840 |
| actcgttctg ccctgcagag atttgtgcaa gatccaaaat atccaggaat actctacaat | 900 |
| catgataacg agtatcttca ctatcaagat gactggtaca ttttgtcctc taagattgaa | 960 |
| aacaaaccag atgactacgc atttgtgtac tacagaggca ggaatgatgc gtgggatggg | 1020 |
| tatggtggtg ctgtcgtcta cacaagaagt gcagtttttgc ctgaaagcat tgtacctgaa | 1080 |
| ctacaaagag cagcgaaaag catagggcgt gatttcagta agttcatcag acagacaac | 1140 |
| acttgcggac ctgaacctcc ccttgtcgag agattggaaa agacagtgga agaaggagaa | 1200 |
| aggacaatcg taagggaggt tgaagagata aaggggaga tagagggtga ggttgagaag | 1260 |
| gtgaaggaca ctgagatgac cttgtttgag aggctgactg aaggatttaa agagctcaaa | 1320 |
| aaagacgagg aattcttcct aagggagctt agcaaggaag agttggatgt tttggacgca | 1380 |
| cttaaaatgg aagcaagcga ggttgaaaaa ctgtttggac gatcactacc aattaggaag | 1440 |
| ctaaggtag | 1449 |

<210> SEQ ID NO 8
<211> LENGTH: 1908
<212> TYPE: DNA
<213> ORGANISM: Coffea canephora

<400> SEQUENCE: 8

| | | | | | |
|---|---|---|---|---|---|
| atgcccatga | ccatgatttt | gcctccttcg | tcaagagaga | tgatgggctt | gggtttgggt | 60 |
| tgctctccga | gctcaaaaac | gctagcattc | agacatccca | atacactgcc | taactacatt | 120 |
| aactgctcct | tgcagacacc | ctccatactc | catttcccaa | agcaatcatc | agcaactacc | 180 |
| tcttctcctc | cttcttcttc | ttctgccaaa | actgcatatc | cagctctttt | tcttcctggt | 240 |
| agcagtgctg | ctattgccac | cccatctaaa | actcccactg | gtactgctac | cgtgccaact | 300 |
| ccgtctccat | caatatcggc | gtcgccatca | ccatcgcggt | cgccatcaac | caccccacaa | 360 |
| tggaacgtac | tacaaagggc | agccgcaatg | gccttagatg | cggtggagac | tgccttgact | 420 |
| gcgcgggaat | tggagcagcc | cctgccaaaa | actgcagacc | ccagaatcca | aatttctgga | 480 |
| aactttgctc | cggtaccgga | acagcccgtc | cggcatgcac | ttccggtcac | tggaaaaatt | 540 |
| cccaattcca | ttcagggcgt | ctacgtccga | acggtgctga | tccactctt | tgaacctgcc | 600 |
| gccggccacc | acttcttcga | cggcgacggc | atgatccacg | ccctccaatt | ccagaacggc | 660 |
| tcagccagct | atgcctgcag | gtttacggag | actcagaggc | ttgcccagga | aaggtctta | 720 |
| ggccgtcctg | ttttccccaa | agccattggc | gagctccatg | ccactccgg | catagccagg | 780 |
| ctcatgcttt | tctatgctcg | tggagtgttt | gggcttcttg | atcatagcca | aggaacgggg | 840 |
| gtggccaacg | ccggcttggt | ttatttcaac | aaccgattgc | tcgccatgtc | tgaagatgac | 900 |
| ttgccgtatc | atgttcgaat | caccccttcg | ggggacttga | aaactgttga | gagatacagt | 960 |
| tcaatggac | agctcaagtc | caccatgata | gctcatccaa | agctggaccc | tgttactggg | 1020 |
| gagctctttg | ctctgagcta | cgatgtaatt | cagaagcctt | atctgaaata | cttcaggttt | 1080 |
| tcgaaagcag | gggagaagtc | gaaagacatt | gaaatcccag | ttcctgaacc | aaccatgatg | 1140 |
| cacgatttcg | ccatcactga | caactttgtg | gtgatccctg | atcaacaagt | cgtcttcaag | 1200 |
| atgtctgaaa | tgattcgtgg | gggctccccg | gtggtgtatg | acaaggagaa | ggtgtcaaga | 1260 |
| ttcggtgtac | tggataagta | tgctgaggat | agttcagcga | tcaagtgggt | agaagtccct | 1320 |
| gactgcttct | gctttcatct | gtggaatgcc | tgggaagagc | ctgaaactga | tgaaattgtg | 1380 |
| gtgattggat | catgtatgac | tcctcctgac | tcgattttca | atgaatgtga | cgaggggttg | 1440 |
| aagagtgttt | tatctgaaat | tcggctaaat | ttgaagacgg | gcaagtctac | caggagggca | 1500 |
| atcatatcca | atcctgagga | tcaagttaat | ctggaggcag | gaatggtgaa | cagaaacaag | 1560 |
| cttgggagga | agacaaggta | tgcatatctg | gctatagctg | agccatggcc | taaagtttct | 1620 |
| ggttttgcaa | aggtggacct | tttcaccggt | gaagtgagaa | agttcattta | cggagatgaa | 1680 |
| aaatatggtg | gtgagcctct | gttcctccca | agagatccca | attgtgaagc | tgaagatgat | 1740 |
| ggttacattc | tggcatttgt | tcatgacgag | aaggaatgga | aatcggagct | tagaattgtc | 1800 |
| aacgccatga | cattggaatt | agaggcatca | gtgcagctgc | catcaagagt | tccatatggt | 1860 |
| ttccatggca | cttttatcag | tgccaaggac | ttggcaagcc | aggcctag | | 1908 |

<210> SEQ ID NO 9
<211> LENGTH: 1647
<212> TYPE: DNA
<213> ORGANISM: Coffea canephora

<400> SEQUENCE: 9

```
atgggtaggc aagaaggaga agaagtggtg gagaaaattg agggaaaaca agaagttgtg      60
gttgtgaatc aaaacccaa taatggattc actgcaaagt tgatagattg ggtggaaaaa      120
gcggtggtga agttgatgta tgattcgaaa cagcctcttc attatctgag tgggaacttt      180
gctcccgttg atgaaactcc tccttgtaag gaccttcttg ttaagggtca tctaccggaa      240
tgcctcaatg gcgagtttgt aagggtcggt cccaatccca agttttctcc tgtggctgga      300
taccattggt ttgacggaga tgggatgatt catggtatac gcataaaaga tggaaaagca      360
acatatgtct cccggtacgt gaagacatca aggcttaaac aagaagaata ttttggggga      420
tctaagttca tgaaggttgg ggatctcaag gggctgttcg gattgttcat ggttaatatg      480
caaattctta gagcaaagct aaaagtttg gatatgactt atggaattgg aacagcaaat      540
acagctctaa tctatcacca tgggaagctc ctggcacttc aagaggctga taaaccatat      600
gtgcttaggg tcttagaaga tggagatcta caaactctag gcctgctgga ttacgacaaa      660
agactgacac attcctttac tgctcatcca aaggttgacc catttaccgg tgagatgttc      720
acatttgggt attcacacac accaccatat atcacataca gagtaatatc caaggaggga      780
gtaatggacg atcctgtgcc aattacaata tcagacccaa tcatgatgca cgattttgcc      840
atcaccgaaa actatgcaat tttcatggat ctcccattgt acttcagacc gaaggaaatg      900
gtgaaagata aaaagctaat attcacattt gatccaacta agaaggctcg ttttggtgtt      960
cttccacggt actcaaagaa tgatgccttg attaaatggt ttgagctgcc aaattgcttt      1020
atattccata atgccaatgc atgggaggaa ggggatgagg ttattcttat cacttgccgt      1080
ctgcagaacc cagacctgga catggttagc ggcattgtga aaagaagct tgaaaatttt      1140
tcaaatgaac tgtatgaaat gcgatttaac ctgaaaactg gtcttgcttc acagaagaaa      1200
ctatcagagt ctgcagtaga ttttccaagg gtgaatgaga gctacactgg aaggaaacaa      1260
caatatgtat atgggaccat attggacagc attgccaagg tcacagggat tgccaaattt      1320
gatttgcatg ctgaaccaga gactggtaaa acaaaaattg aagttggtgg taatgttcaa      1380
ggtgtctttg acctaggacc aggaaggttt ggttcggagg ctatctttgt tccacgccag      1440
cctggtatta catctgaaga ggatgatggc tacttgatat tcttcgtaca tgatgaatcg      1500
actggaaagt cagctgtaaa tgtgattgat gcaaaaacaa tgtcagctga tcctgttgcc      1560
gttgttgaat tacctaatag agttccatac gggttccatg ctttctttgt gacagaggaa      1620
caacttgaag aacaagcaaa actttga      1647
```

<210> SEQ ID NO 10
<211> LENGTH: 963
<212> TYPE: DNA
<213> ORGANISM: Coffea canephora

<400> SEQUENCE: 10

```
atggcttcca tcacttcttt caatcaattc tcatacacag taaagtctaa aacctttcaa      60
catcctcaat tcggcactaa agtttcaaat tctgccgtga atttcaccga tttcggactg      120
aaaaagccgc tccaaagctc tatttcaatc aaagaatcgt caaagaaaag gcctgggttt      180
gtagtactgg tggctgcagg cgatgattat ggcccagagg aggaagcagc cggggttgcg      240
gtggcggagg agccgccgcc aaaggagccg agggagattg atatcttgaa gaaacggttg      300
gtggactcgt tttatggaac cgatagagga ttgaatgcca gcagcgagac gagggcggag      360
gtggtggaac tgatcaccca gctggaggct aaaaacccaa ctccggctcc aactgaggcg      420
```

```
ttgactctgc tcaatggcaa atggattctt gcgtacacgt cttttattgg attgtttcct    480
ttgttgtcga gaggcacact gcccttggtg aaggtggagg agatatcaca gaccattgac    540
tcagaggcct tctctgttga aatgtcgtc cagtttgctg gccattggc tacgacgtcc      600
attactacaa atgccaaatt tgaagtccgc agtcccaagc gcgtgcagat aaagtttgaa    660
gaaggtgtca ttggaactcc ccagttgaca gactccattg agctgccaga agtgtggag    720
cttctgggac aaaagatcga tcttaacccc gttaagggct tgcttacttc tgtccaggac    780
acagcatcct cagtcgcaaa gtccatttct agccgaccac cactgaaatt ctctctttct    840
aataggaatg ccgagtcgtg gcttctcacc acatacctgg atgatgagct tcggatttca    900
aggggagatg gaggcagtat ttttgtgctt atcaaggaag gctgccctct tctgaaacct    960
tag                                                                 963
```

<210> SEQ ID NO 11
<211> LENGTH: 1149
<212> TYPE: DNA
<213> ORGANISM: Coffea canephora

<400> SEQUENCE: 11

```
aaatctgcgt tttgggctca ttgcatgcga agagctgttt ccatgggcca agagagatg     60
gtggatttta tggatctttt gctctctcca gcctcaaagg ttctaaataa ctggtttgag   120
actgaagtcc tgaaggcaac acttgcaaca gatgcagtaa taggaaccac ggcaagtgtc   180
catacaccag gaactggcta tgttttgctt catcacatca tggagaaaac tgatggtgat   240
cgtggaattt ggtcatatgt tgaaggtgga atgggttccg tgtctttggc tgttggtagt   300
gcagcacagg aggcgggtgc tacaatagtg actaaagctg aggtctcaaa attgctaatt   360
ggtgattcag gaagagtaga cggggtgttg cttcctgatg gaactgaagt gcagtcttct   420
gttgtttat caaatgctac tccatataaa acttttatgg aattagtgcc agaacatgtg    480
cttcctgatg actttcttca ggcaatcaag tgttctgatt acagctctgc aactacaaaa   540
attaacttgg ctgttgagcg agtgccacaa tttcagtgct gcaagattaa tcatcctaat   600
gctggtcctc agcatatggg taccatccat attggttcag agaggatgga agaggttgat   660
tcagcctgtc aagaagctgt aaatggtttt ccctctaaaa gacctatcat tgagatgaca   720
atcccttctg tcttggacaa gactatctct ccccatggta agcatatcat caacttattt   780
attcagtaca caccttataa acctttggat ggcagttggg aagaccctgc atataggaa    840
tcatttgcac aaagatgctt ctccttaatt gatgattatg ccctggctt tagctcgtca    900
attcttggat atgacatgtt gactccacca gatcttgaga gagaaattgg tttgacagga   960
ggaaatattt tcacggtgc catggggttg gattctttgt tccttatgcg acctgttaaa   1020
ggatggtcga attacaggac tccagtacaa ggtctatact tatgtggaag tggagctcat  1080
cctgggggag gcgtgatggg tgctgccggt cgtaatgctg caggcacagt cattcaagac  1140
tggaagtag                                                          1149
```

<210> SEQ ID NO 12
<211> LENGTH: 472
<212> TYPE: DNA
<213> ORGANISM: Coffea canephora

<400> SEQUENCE: 12

```
tggagctttt ggatcaaggc catgaggtgg atatttatga atcacattct tttattggtg     60
gtaaagtagg ttcttttgtt gataaacgag gaaatcacat tggaatggga ctgcatgtct   120
```

```
tctttggttg ctacaacaac cttttccgcc tgatgaaaaa ggtaggtgct gataaaaatt      180
tgctcgtgaa ggatcatact cacacatttg ttaacaaagg gggtgaaatt ggtgaacttg      240
atttccgctt ccagttgggg gcacctttac atggaattaa tgcattcttg tctaccaatc     300
agctaaagat ttatgataag caagaaatg ccgtggctct cgcgcttggt ccagttgtac      360
gggctctggt tgatcctgat ggagcgctga gggagatacg ggatttagac aggataagct      420
tctcagattg gttcttatcc aaaggaggga ctcgcgcaag tatacagagg at             472
```

<210> SEQ ID NO 13
<211> LENGTH: 439
<212> TYPE: PRT
<213> ORGANISM: Coffea canephora

<400> SEQUENCE: 13

```
Met Ser Val Ala Leu Leu Trp Val Val Leu Pro Ile Ser Glu Val Thr
1               5                   10                  15

Asn Ser Ile Ala Phe Leu Glu Pro Val Arg Glu Gly Ser Arg Leu Leu
            20                  25                  30

Asp Ser Ser Arg Phe Val Gly Arg Gly Lys Asn Cys Leu Cys Asn Gly
        35                  40                  45

Arg Leu Glu Lys Gly Lys Gln Gln Arg Trp Asn Ser Gly Tyr Leu Asn
    50                  55                  60

Gly Asp Ser Arg Asn Cys Cys Leu Gly Gly Ser Arg Leu Lys Asn Arg
65                  70                  75                  80

Gly Lys Phe Ser Val Ile Pro Asn Val Val Ser Pro Ala Gly Glu
                85                  90                  95

Ile Ala Met Ser Ser Glu Gln Lys Val Tyr Asp Val Val Leu Lys Gln
            100                 105                 110

Ala Ala Leu Val Asn Arg Gln Leu Arg Ser Arg Glu Asp Trp Asp Val
        115                 120                 125

Lys Pro Asp Ile Val Leu Pro Gly Asn Leu Asn Ile Leu Ser Glu Ala
    130                 135                 140

Tyr Asp Arg Cys Gly Glu Val Cys Ala Glu Tyr Ala Gln Thr Phe Tyr
145                 150                 155                 160

Leu Gly Thr Met Leu Met Thr Pro Glu Arg Arg Arg Ala Ile Trp Ala
                165                 170                 175

Ile Tyr Val Trp Cys Arg Arg Thr Asp Glu Leu Val Asp Gly Pro Asn
            180                 185                 190

Ala Ser His Ile Thr Pro Thr Ala Leu Asp Arg Trp Glu Ala Arg Leu
        195                 200                 205

Glu Asp Val Phe Arg Gly His Pro Phe Asp Met Leu Asp Ala Ala Leu
    210                 215                 220

Ser Asp Thr Val Ser Lys Phe Pro Val Asp Ile Gln Pro Phe Arg Asp
225                 230                 235                 240

Met Ile Glu Gly Met Arg Met Asp Leu Lys Lys Ser Arg Tyr Lys Asn
                245                 250                 255

Phe Asp Glu Leu Tyr Leu Tyr Cys Tyr Tyr Val Ala Gly Thr Val Gly
            260                 265                 270

Leu Met Ser Val Pro Val Met Gly Ile Ala Pro Glu Ser Lys Ala Thr
        275                 280                 285

Val Glu Ser Val Tyr Asn Ala Ala Leu Ala Leu Gly Ile Ala Asn Gln
    290                 295                 300

Leu Thr Asn Ile Leu Arg Asp Val Gly Glu Asp Ala Thr Arg Gly Arg
305                 310                 315                 320
```

```
Ile Tyr Leu Pro Gln Asp Glu Leu Ala Gln Ala Gly Leu Ser Asp Glu
            325                 330                 335

Asp Ile Phe Ala Gly Lys Val Thr Asp Gln Trp Arg Asn Phe Met Lys
        340                 345                 350

Gln Gln Met Lys Arg Ala Arg Lys Phe Phe Asp Glu Ala Glu Lys Gly
            355                 360                 365

Val Thr Glu Leu Asn Ser Ala Ser Arg Trp Pro Val Trp Ala Ser Leu
    370                 375                 380

Leu Leu Tyr Arg Gln Ile Leu Asp Glu Ile Glu Ala Asn Asp Tyr Asn
385                 390                 395                 400

Asn Phe Asp Arg Arg Ala Tyr Val Ser Lys Pro Lys Lys Leu Leu Ala
                405                 410                 415

Leu Pro Met Ala Tyr Ala Lys Ser Leu Val Pro Pro Arg Thr Ser Ser
            420                 425                 430

Pro Leu Ala Lys Gly Met Ser
            435

<210> SEQ ID NO 14
<211> LENGTH: 359
<212> TYPE: PRT
<213> ORGANISM: Coffea canephora

<400> SEQUENCE: 14

Ile Asp Tyr Pro Arg Pro Glu Leu Glu Asn Ala Val Asn Tyr Leu Glu
1               5                   10                  15

Ala Ala Tyr Leu Ser Ser Thr Phe Arg Thr Ser Pro His Pro Asn Lys
            20                  25                  30

Pro Leu Glu Val Val Ile Ala Gly Ala Gly Leu Ala Gly Leu Ser Thr
        35                  40                  45

Ala Lys Tyr Leu Ala Asp Ala Gly His Lys Pro Ile Val Leu Glu Ala
    50                  55                  60

Arg Asp Val Leu Gly Gly Lys Val Ala Ala Trp Lys Asp Asp Asp Gly
65                  70                  75                  80

Asp Trp Tyr Glu Thr Gly Leu His Val Phe Phe Gly Ala Tyr Pro Asn
                85                  90                  95

Met Gln Asn Leu Phe Gly Glu Leu Gly Ile Asn Asp Arg Leu Gln Trp
            100                 105                 110

Lys Glu His Ser Met Ile Phe Ala Met Pro Asn Lys Pro Gly Glu Phe
        115                 120                 125

Ser Arg Phe Asp Phe Pro Glu Val Leu Pro Ala Pro Leu Asn Gly Ile
    130                 135                 140

Trp Ala Ile Leu Lys Asn Asn Asp Met Leu Thr Trp Pro Glu Lys Val
145                 150                 155                 160

Lys Phe Ala Ile Gly Leu Leu Pro Ala Ile Leu Gly Gly Gln Ser Tyr
                165                 170                 175

Val Glu Ala Gln Asp Gly Ile Thr Val Lys Asp Trp Met Arg Lys Gln
            180                 185                 190

Gly Ile Pro Asp Arg Val Thr Asp Glu Val Phe Phe Ala Met Ser Lys
        195                 200                 205

Ala Leu Asn Phe Ile Asn Pro Asp Glu Leu Ser Met Gln Cys Ile Leu
    210                 215                 220

Ile Ala Leu Asn Arg Phe Leu Gln Glu Lys His Gly Ser Lys Met Ala
225                 230                 235                 240

Phe Leu Asp Gly Asn Pro Pro Glu Arg Leu Cys Met Pro Ile Val Glu
                245                 250                 255
```

```
His Ile Glu Ser Arg Gly Gly Arg Val His Leu Asn Ser Arg Ile Gln
            260                 265                 270

Lys Ile Glu Leu Asn Asp Ala Gly Ser Val Glu Asn Phe Leu Leu Ser
        275                 280                 285

Asn Gly Thr Val Ile Arg Gly Asp Ala Tyr Val Phe Ala Thr Pro Val
    290                 295                 300

Asp Ile Leu Lys Leu Leu Leu Pro Glu Asp Trp Lys Glu Met Pro Tyr
305                 310                 315                 320

Phe Arg Lys Leu Glu Lys Leu Val Gly Val Pro Val Ile Asn Val His
                325                 330                 335

Ile Trp Phe Asp Arg Lys Leu Arg Asn Thr Tyr Asp His Leu Leu Phe
            340                 345                 350

Ser Arg Ser Pro Leu Leu Ser
        355

<210> SEQ ID NO 15
<211> LENGTH: 351
<212> TYPE: PRT
<213> ORGANISM: Coffea canephora

<400> SEQUENCE: 15

Met Ala Thr Ser Thr Ser Ser Val Val Phe Gly Ile Ser Val Ser Ser
1               5                   10                  15

Ser Thr Ser Leu Lys Ile Arg Ser Phe Arg Asn Val Pro Thr Val Leu
            20                  25                  30

Asn Ser His Thr Pro Ser Gly Leu Asn Val Val Thr Ser Pro His His
        35                  40                  45

Arg His Thr Ala Thr Gln Arg Pro Leu Ser Arg Asn Ser Phe Arg Val
    50                  55                  60

Gln Ala Thr Val Leu Gln Glu Asp Glu Gln Lys Val Val Val Glu Glu
65                  70                  75                  80

Ser Phe Gln Ser Lys Ser Tyr Pro Glu Asn Gly Gly Gly Asn Gly
                85                  90                  95

Glu Pro Pro Asp Ala Ser Ser Ser Gly Leu Glu Lys Trp Val Val
        100                 105                 110

Lys Ile Glu Gln Ser Ile Asn Ile Phe Leu Thr Asp Ser Val Ile Lys
            115                 120                 125

Ile Leu Asp Thr Leu Tyr His Asp Arg His Tyr Ala Arg Phe Val
130                 135                 140

Leu Glu Thr Ile Ala Arg Val Pro Tyr Phe Ala Phe Met Ser Val Leu
145                 150                 155                 160

His Leu Tyr Glu Ser Phe Gly Trp Trp Arg Arg Ala Asp Leu Ser Glu
                165                 170                 175

Val His Phe Ala Glu Ser Trp Asn Glu Met His His Leu Leu Ile Met
        180                 185                 190

Glu Glu Leu Gly Gly Asn Ser Trp Trp Phe Asp Arg Phe Leu Ala Gln
            195                 200                 205

His Ile Ala Val Phe Tyr Tyr Phe Met Thr Val Phe Met Tyr Met Leu
    210                 215                 220

Ser Pro Arg Met Ala Tyr His Phe Ser Glu Cys Val Glu Ser His Ala
225                 230                 235                 240

Phe Glu Thr Tyr Asp Lys Phe Ile Lys Asp Gln Gly Glu Gln Leu Lys
                245                 250                 255

Lys Leu Pro Ala Ser Asn Val Ala Val Lys Tyr Tyr Thr Glu Gly Asn
        260                 265                 270
```

```
Leu Tyr Leu Phe Asp Glu Phe Gln Thr Ala Arg Pro Pro Thr Ser Arg
        275                 280                 285

Arg Pro Lys Ile Glu Asn Met Tyr Asp Val Phe Leu Asn Ile Arg Asp
        290                 295                 300

Asp Glu Ala Glu His Cys Lys Thr Met Lys Ala Cys Gln Thr His Gly
305                 310                 315                 320

Gly Leu Arg Ser Pro His Ser Tyr Thr Asp Asp Ala Cys Glu Glu Asp
                325                 330                 335

Ala Gly Tyr Gly Leu Pro Gln Ala Asp Cys Glu Glu Leu Thr Gln
        340                 345                 350

<210> SEQ ID NO 16
<211> LENGTH: 310
<212> TYPE: PRT
<213> ORGANISM: Coffea canephora

<400> SEQUENCE: 16

Met Ala Ala Gly Ile Ala Val Ala Ala Gly Ala Gln Thr Val Cys Phe
1               5                   10                  15

Arg Val Asn Ser Phe Leu Thr Arg Lys Pro Thr Ser Leu Val Ala Asp
            20                  25                  30

Ser Leu Thr Leu Ser Pro Leu Ala Gln Gln Phe Ser Thr Thr Arg Arg
        35                  40                  45

His Arg Arg Lys Pro Arg Leu Thr Val Cys Phe Val Leu Glu Asp Glu
    50                  55                  60

Glu Leu Lys Ala Gln Leu Val Thr Ser Glu Glu Ala Arg Glu Arg
65                  70                  75                  80

Glu Lys Ala Met Ala Lys Arg Ile Ser Asp Ala Arg Thr Ala Glu Lys
                85                  90                  95

Leu Ala Arg Lys Arg Ser Glu Arg Phe Thr Tyr Leu Val Ala Ala Val
            100                 105                 110

Met Ser Ser Phe Gly Ile Thr Ser Met Ala Val Leu Ala Val Tyr Tyr
        115                 120                 125

Arg Phe Val Trp Gln Met Glu Gly Gly Glu Val Pro Tyr Ser Glu Met
    130                 135                 140

Phe Gly Thr Phe Ala Leu Ser Val Gly Ala Ala Val Gly Met Glu Phe
145                 150                 155                 160

Trp Ala Arg Trp Ala His Lys Ala Leu Trp His Ala Ser Leu Trp His
                165                 170                 175

Met His Glu Ser His His Arg Pro Arg Glu Gly Pro Phe Glu Leu Asn
            180                 185                 190

Asp Val Phe Ala Ile Ile Asn Ala Val Pro Ala Ile Ala Leu Leu Ser
        195                 200                 205

Tyr Gly Phe Phe His Lys Gly Leu Ile Pro Gly Leu Cys Phe Gly Ala
    210                 215                 220

Gly Leu Gly Ile Ile Val Phe Gly Met Ala Tyr Met Phe Val His Asp
225                 230                 235                 240

Gly Leu Val His Lys Arg Phe Pro Val Gly Pro Ile Ala Asn Val Pro
                245                 250                 255

Tyr Phe Arg Arg Val Ala Ala Ala His Gln Leu His His Ser Asp Lys
            260                 265                 270

Phe Asn Gly Val Pro Phe Gly Leu Phe Leu Gly Pro Lys Glu Leu Glu
        275                 280                 285
```

```
Lys Val Gly Gly Leu Glu Glu Leu Glu Lys Glu Ile Asn Arg Arg Ile
290                 295                 300

Lys Leu Arg Lys Gly Ser
305                 310

<210> SEQ ID NO 17
<211> LENGTH: 469
<212> TYPE: PRT
<213> ORGANISM: Coffea canephora

<400> SEQUENCE: 17

Cys Val Val Asp Lys Glu Glu Lys Phe Ala Asp Gln Glu Asp Tyr Ile
1               5                   10                  15

Lys Ala Gly Gly Ser Glu Leu Leu Tyr Val Gln Met Gln Gln Arg Lys
            20                  25                  30

Gln Met Asp Gln Gln Ser Lys Phe Ser Asp Lys Met Pro Glu Ile Ser
        35                  40                  45

Ala Gly Asn Ser Ile Leu Asp Leu Val Val Ile Gly Cys Gly Pro Ala
    50                  55                  60

Gly Leu Ala Leu Ala Ala Glu Ser Ala Lys Leu Gly Leu Thr Val Gly
65                  70                  75                  80

Leu Ile Gly Pro Asp Val Pro Phe Thr Asn Asn Tyr Gly Val Trp Glu
                85                  90                  95

Asp Glu Phe Lys Asp Leu Gly Leu Ala Gly Cys Ile Glu His Val Trp
            100                 105                 110

Arg Asp Thr Val Val Tyr Leu Asp Asp Asn Asp Pro Ile Leu Ile Gly
        115                 120                 125

Arg Ala Tyr Gly Arg Phe Ser Arg His Leu Leu His Glu Glu Leu Leu
    130                 135                 140

Arg Arg Cys Val Glu Ser Gly Val Ser Tyr Leu Ser Ser Val Glu Arg
145                 150                 155                 160

Ile Val Glu Ala Ala Thr Gly His Ser Leu Val Glu Cys Glu Gly Ser
                165                 170                 175

Ile Val Ile Pro Cys Arg Leu Ala Thr Val Ala Ser Gly Ala Ala Ser
            180                 185                 190

Gly Lys Leu Leu Gln Tyr Glu Leu Gly Gly Pro Arg Val Ser Val Gln
        195                 200                 205

Thr Ala Tyr Gly Val Glu Val Glu Asn Asn Pro Tyr Asp Pro
    210                 215                 220

Asn Leu Met Val Phe Met Asp Tyr Arg Asp Tyr Met Arg Gly Lys Val
225                 230                 235                 240

Glu Ser Leu Glu Ala Glu Phe Pro Thr Phe Leu Tyr Ala Met Pro Met
                245                 250                 255

Ser Pro Thr Arg Val Phe Phe Glu Glu Thr Cys Leu Ala Ser Lys Asp
            260                 265                 270

Ala Met Pro Phe Glu Leu Leu Lys Lys Lys Leu Met Ser Arg Leu Asp
        275                 280                 285

Thr Leu Gly Val Arg Ile Ile Lys Thr Tyr Glu Glu Glu Trp Ser Tyr
    290                 295                 300

Ile Pro Val Gly Gly Ser Leu Pro Asn Thr Glu Gln Lys Asn Leu Ala
305                 310                 315                 320

Phe Gly Ala Ala Ala Ser Met Val His Pro Ala Thr Gly Tyr Ser Val
                325                 330                 335

Val Arg Ser Leu Ser Glu Ala Pro Lys Tyr Ala Ser Ala Ile Ala Asn
            340                 345                 350
```

```
Ile Leu Lys Gln Gly Gln Ala Lys Asp Met Met Thr Arg Asn Ile Ser
        355                 360                 365

Ala Gln Ala Trp Asn Thr Leu Trp Pro Gln Glu Arg Lys Arg Gln Arg
    370                 375                 380

Ala Phe Phe Leu Phe Gly Leu Ala Leu Ile Leu Gln Leu Asp Ile Glu
385                 390                 395                 400

Gly Ile Arg Thr Phe Phe Gln Thr Phe Phe Arg Leu Pro Asn Trp Met
                405                 410                 415

Ser Gln Gly Phe Leu Gly Ser Ser Leu Ser Ser Thr Asp Leu Leu Leu
                420                 425                 430

Phe Ala Phe Tyr Met Phe Val Ile Ala Pro Asn Asp Leu Arg Lys Cys
            435                 440                 445

Leu Ile Gln His Leu Leu Ser Asp Pro Thr Gly Ala Thr Met Val Arg
450                 455                 460

Thr Tyr Leu Ala Ile
465

<210> SEQ ID NO 18
<211> LENGTH: 343
<212> TYPE: PRT
<213> ORGANISM: Coffea canephora

<400> SEQUENCE: 18

Gly Lys Lys Glu Arg Leu Leu Lys Ile Phe Asp Gly Trp Cys Asp Lys
1               5                   10                  15

Val Met Glu Leu Leu Leu Ala Thr Asp Glu Asp Ala Ile Leu Arg Arg
            20                  25                  30

Asp Ile Tyr Asp Arg Thr Pro Ser Phe Ser Trp Gly Arg Gly Arg Val
        35                  40                  45

Thr Leu Leu Gly Asp Ser Ile His Ala Met Gln Pro Asn Leu Gly Gln
    50                  55                  60

Gly Gly Cys Met Ala Ile Glu Asp Ser Tyr Gln Leu Ala Leu Glu Leu
65                  70                  75                  80

Asp Lys Ala Trp Glu Gln Ser Ile Lys Ser Gly Ser Pro Met Asp Val
                85                  90                  95

Val Ser Ala Leu Lys Ser Tyr Glu Ser Ala Arg Lys Leu Arg Val Ala
            100                 105                 110

Ile Ile His Gly Leu Ala Arg Leu Ala Ala Ile Met Ala Ser Thr Tyr
        115                 120                 125

Lys Pro Tyr Leu Gly Val Gly Leu Gly Pro Leu Ser Phe Leu Thr Lys
    130                 135                 140

Phe Arg Ile Pro His Pro Gly Arg Val Gly Gly Arg Ile Phe Ile Asp
145                 150                 155                 160

Ile Gly Met Pro Leu Met Leu Ser Trp Val Leu Gly Gly Asn Gly Ser
                165                 170                 175

Lys Leu Glu Gly Arg Pro Leu His Cys Arg Leu Thr Asp Lys Ala Ser
            180                 185                 190

Asp Gln Leu Gln Lys Trp Phe Gln Asp Asp Ser Leu Glu Arg Ala
        195                 200                 205

Leu Asn Gly Glu Trp Phe Leu Phe Pro Ile Gly Gln Ala Asn Pro Asp
    210                 215                 220

Pro Val Ala Ile Phe Leu Gly Arg Asp Glu Lys Asn Ile Cys Thr Ile
225                 230                 235                 240

Gly Ser Ala Ser His Pro Asp Ile Leu Gly Ala Ser Ile Ile Ile Asn
                245                 250                 255
```

```
Ser Pro Gln Val Ser Lys Leu His Ala Gln Ile Ser Tyr Lys Asp Gly
            260                 265                 270

Leu Phe Phe Leu Thr Asp Leu Gln Ser Glu His Gly Thr Trp Ile Thr
        275                 280                 285

Asp Asn Asp Gly Arg Arg Tyr Arg Leu Pro Pro Asn Ser Pro Ala Arg
    290                 295                 300

Phe His Pro Tyr Asp Ile Ile Glu Phe Gly Ser Asp Lys Ala Ala Phe
305                 310                 315                 320

Arg Val Lys Val Thr Asn Gln Pro Pro Phe Ser Gly Lys Lys Arg Glu
                325                 330                 335

Thr Lys Val Leu Ser Ala Val
            340

<210> SEQ ID NO 19
<211> LENGTH: 415
<212> TYPE: PRT
<213> ORGANISM: Coffea canephora

<400> SEQUENCE: 19

Met Ala Ser Ala Leu His Ser Ala Phe His Ser Asn Asp Glu Gly Ile
1               5                   10                  15

Arg Phe Tyr Ile Arg Ser Gln His Arg Ile Gly Gly Arg Cys Ser Asn
            20                  25                  30

Gly Gly Ala Arg Pro Gln Asn Ala Leu Phe Ser Val Lys Met Trp Ser
        35                  40                  45

Lys Arg Trp Gly Ser Arg Tyr Ile Gln Leu Gln Arg Ala Pro Arg Ile
    50                  55                  60

Ser Leu Ser Leu Gly Ser Lys Cys Thr Arg Leu Phe Leu Asn Gly Ile
65                  70                  75                  80

Cys Arg Ile Glu Leu Ala Lys Cys Ile Ala Asn Pro Ser Cys Ala Ala
                85                  90                  95

Asn Val Ala Cys Leu Gln Thr Cys Asn Asn Arg Pro Asp Glu Thr Glu
            100                 105                 110

Cys Gln Ile Lys Cys Gly Asp Leu Phe Gln Asn Ser Val Val Asp Glu
        115                 120                 125

Phe Asn Glu Cys Ala Val Ser Arg Lys Lys Cys Val Pro Arg Lys Ser
    130                 135                 140

Asp Val Gly Glu Phe Pro Ala Pro Asp Pro Ala Val Leu Val Lys Asn
145                 150                 155                 160

Phe Asp Ile Lys Asp Phe Ser Gly Lys Trp Tyr Ile Ser Ser Gly Leu
                165                 170                 175

Asn Pro Thr Phe Asp Thr Phe Asp Cys Gln Leu His Glu Phe His Thr
            180                 185                 190

Glu Ser Gly Lys Leu Val Gly Asn Leu Thr Trp Arg Ile Arg Thr Pro
        195                 200                 205

Asp Thr Gly Phe Phe Thr Arg Ser Ala Leu Gln Arg Phe Val Gln Asp
    210                 215                 220

Pro Lys Tyr Pro Gly Ile Leu Tyr Asn His Asp Asn Glu Tyr Leu His
225                 230                 235                 240

Tyr Gln Asp Asp Trp Tyr Ile Leu Ser Ser Lys Ile Glu Asn Lys Pro
                245                 250                 255

Asp Asp Tyr Ala Phe Val Tyr Tyr Arg Gly Arg Asn Asp Ala Trp Asp
            260                 265                 270

Gly Tyr Gly Gly Ala Val Val Tyr Thr Arg Ser Ala Val Leu Pro Glu
        275                 280                 285
```

```
Ser Ile Val Pro Glu Leu Gln Arg Ala Ala Lys Ser Ile Gly Arg Asp
            290                 295                 300

Phe Ser Lys Phe Ile Arg Thr Asp Asn Thr Cys Gly Pro Glu Pro Pro
305                 310                 315                 320

Leu Val Glu Arg Leu Glu Lys Thr Val Glu Glu Gly Glu Arg Thr Ile
                325                 330                 335

Val Arg Glu Val Glu Glu Ile Glu Gly Glu Ile Glu Gly Glu Val Glu
                340                 345                 350

Lys Val Lys Asp Thr Glu Met Thr Leu Phe Glu Arg Leu Thr Glu Gly
                355                 360                 365

Phe Lys Glu Leu Lys Lys Asp Glu Glu Phe Phe Leu Arg Glu Leu Ser
370                 375                 380

Lys Glu Glu Leu Asp Val Leu Asp Ala Leu Lys Met Glu Ala Ser Glu
385                 390                 395                 400

Val Glu Lys Leu Phe Gly Arg Ser Leu Pro Ile Arg Lys Leu Arg
                405                 410                 415

<210> SEQ ID NO 20
<211> LENGTH: 635
<212> TYPE: PRT
<213> ORGANISM: Coffea canephora

<400> SEQUENCE: 20

Met Pro Met Thr Met Ile Leu Pro Pro Ser Arg Glu Met Met Gly
1               5                   10                  15

Leu Gly Leu Gly Cys Ser Pro Ser Ser Lys Thr Leu Ala Phe Arg His
                20                  25                  30

Pro Asn Thr Leu Pro Asn Tyr Ile Asn Cys Ser Leu Gln Thr Pro Ser
                35                  40                  45

Ile Leu His Phe Pro Lys Gln Ser Ser Ala Thr Thr Ser Ser Pro Pro
50                  55                  60

Ser Ser Ser Ser Ala Lys Thr Ala Tyr Pro Ala Leu Phe Leu Pro Gly
65                  70                  75                  80

Ser Ser Ala Ala Ile Ala Thr Pro Ser Lys Thr Pro Thr Gly Thr Ala
                85                  90                  95

Thr Val Pro Thr Pro Ser Pro Ser Ile Ser Ala Ser Pro Ser Pro Ser
                100                 105                 110

Arg Ser Pro Ser Thr Thr Pro Gln Trp Asn Val Leu Gln Arg Ala Ala
                115                 120                 125

Ala Met Ala Leu Asp Ala Val Glu Thr Ala Leu Thr Ala Arg Glu Leu
130                 135                 140

Glu Gln Pro Leu Pro Lys Thr Ala Asp Pro Arg Ile Gln Ile Ser Gly
145                 150                 155                 160

Asn Phe Ala Pro Val Pro Glu Gln Pro Val Arg His Ala Leu Pro Val
                165                 170                 175

Thr Gly Lys Ile Pro Asn Ser Ile Gln Gly Val Tyr Val Arg Asn Gly
                180                 185                 190

Ala Asn Pro Leu Phe Glu Pro Ala Ala Gly His His Phe Phe Asp Gly
                195                 200                 205

Asp Gly Met Ile His Ala Leu Gln Phe Gln Asn Gly Ser Ala Ser Tyr
                210                 215                 220

Ala Cys Arg Phe Thr Glu Thr Gln Arg Leu Ala Gln Glu Arg Ser Leu
225                 230                 235                 240

Gly Arg Pro Val Phe Pro Lys Ala Ile Gly Glu Leu His Gly His Ser
                245                 250                 255
```

```
Gly Ile Ala Arg Leu Met Leu Phe Tyr Ala Arg Gly Val Phe Gly Leu
            260                 265                 270

Leu Asp His Ser Gln Gly Thr Gly Val Ala Asn Ala Gly Leu Val Tyr
275                 280                 285

Phe Asn Asn Arg Leu Leu Ala Met Ser Glu Asp Leu Pro Tyr His
290                 295                 300

Val Arg Ile Thr Pro Ser Gly Asp Leu Lys Thr Val Glu Arg Tyr Ser
305                 310                 315                 320

Phe Asn Gly Gln Leu Lys Ser Thr Met Ile Ala His Pro Lys Leu Asp
                325                 330                 335

Pro Val Thr Gly Glu Leu Phe Ala Leu Ser Tyr Asp Val Ile Gln Lys
            340                 345                 350

Pro Tyr Leu Lys Tyr Phe Arg Phe Ser Lys Ala Gly Glu Lys Ser Lys
        355                 360                 365

Asp Ile Glu Ile Pro Val Pro Glu Pro Thr Met Met His Asp Phe Ala
370                 375                 380

Ile Thr Asp Asn Phe Val Val Ile Pro Asp Gln Gln Val Val Phe Lys
385                 390                 395                 400

Met Ser Glu Met Ile Arg Gly Gly Ser Pro Val Val Tyr Asp Lys Glu
                405                 410                 415

Lys Val Ser Arg Phe Gly Val Leu Asp Lys Tyr Ala Glu Asp Ser Ser
            420                 425                 430

Ala Ile Lys Trp Val Glu Val Pro Asp Cys Phe Cys Phe His Leu Trp
        435                 440                 445

Asn Ala Trp Glu Glu Pro Glu Thr Asp Glu Ile Val Val Ile Gly Ser
450                 455                 460

Cys Met Thr Pro Pro Asp Ser Ile Phe Asn Glu Cys Asp Glu Gly Leu
465                 470                 475                 480

Lys Ser Val Leu Ser Glu Ile Arg Leu Asn Leu Lys Thr Gly Lys Ser
                485                 490                 495

Thr Arg Arg Ala Ile Ile Ser Asn Pro Glu Asp Gln Val Asn Leu Glu
            500                 505                 510

Ala Gly Met Val Asn Arg Asn Lys Leu Gly Arg Lys Thr Arg Tyr Ala
        515                 520                 525

Tyr Leu Ala Ile Ala Glu Pro Trp Pro Lys Val Ser Gly Phe Ala Lys
530                 535                 540

Val Asp Leu Phe Thr Gly Glu Val Arg Lys Phe Ile Tyr Gly Asp Glu
545                 550                 555                 560

Lys Tyr Gly Gly Glu Pro Leu Phe Leu Pro Arg Asp Pro Asn Cys Glu
                565                 570                 575

Ala Glu Asp Asp Gly Tyr Ile Leu Ala Phe Val His Asp Glu Lys Glu
            580                 585                 590

Trp Lys Ser Glu Leu Arg Ile Val Asn Ala Met Thr Leu Glu Leu Glu
        595                 600                 605

Ala Ser Val Gln Leu Pro Ser Arg Val Pro Tyr Gly Phe His Gly Thr
610                 615                 620

Phe Ile Ser Ala Lys Asp Leu Ala Ser Gln Ala
625                 630                 635

<210> SEQ ID NO 21
<211> LENGTH: 548
<212> TYPE: PRT
<213> ORGANISM: Coffea canephora
```

<400> SEQUENCE: 21

```
Met Gly Arg Gln Glu Gly Glu Val Val Glu Lys Ile Glu Gly Lys
1               5                   10                  15

Gln Glu Val Val Val Asn Pro Lys Pro Asn Asn Gly Phe Thr Ala
            20                  25                  30

Lys Leu Ile Asp Trp Val Glu Lys Ala Val Val Lys Leu Met Tyr Asp
            35                  40                  45

Ser Lys Gln Pro Leu His Tyr Leu Ser Gly Asn Phe Ala Pro Val Asp
    50                  55                  60

Glu Thr Pro Pro Cys Lys Asp Leu Leu Val Lys Gly His Leu Pro Glu
65                  70                  75                  80

Cys Leu Asn Gly Glu Phe Val Arg Val Gly Pro Asn Pro Lys Phe Ser
                85                  90                  95

Pro Val Ala Gly Tyr His Trp Phe Asp Gly Asp Gly Met Ile His Gly
                100                 105                 110

Ile Arg Ile Lys Asp Gly Lys Ala Thr Tyr Val Ser Arg Tyr Val Lys
                115                 120                 125

Thr Ser Arg Leu Lys Gln Glu Glu Tyr Phe Gly Gly Ser Lys Phe Met
130                 135                 140

Lys Val Gly Asp Leu Lys Gly Leu Phe Gly Leu Phe Met Val Asn Met
145                 150                 155                 160

Gln Ile Leu Arg Ala Lys Leu Lys Val Leu Asp Met Thr Tyr Gly Ile
                165                 170                 175

Gly Thr Ala Asn Thr Ala Leu Ile Tyr His His Gly Lys Leu Leu Ala
                180                 185                 190

Leu Gln Glu Ala Asp Lys Pro Tyr Val Leu Arg Val Leu Glu Asp Gly
        195                 200                 205

Asp Leu Gln Thr Leu Gly Leu Leu Asp Tyr Asp Lys Arg Leu Thr His
        210                 215                 220

Ser Phe Thr Ala His Pro Lys Val Asp Pro Phe Thr Gly Glu Met Phe
225                 230                 235                 240

Thr Phe Gly Tyr Ser His Thr Pro Pro Tyr Ile Thr Tyr Arg Val Ile
                245                 250                 255

Ser Lys Glu Gly Val Met Asp Asp Pro Val Pro Ile Thr Ile Ser Asp
                260                 265                 270

Pro Ile Met Met His Asp Phe Ala Ile Thr Glu Asn Tyr Ala Ile Phe
                275                 280                 285

Met Asp Leu Pro Leu Tyr Phe Arg Pro Lys Glu Met Val Lys Asp Lys
        290                 295                 300

Lys Leu Ile Phe Thr Phe Asp Pro Thr Lys Lys Ala Arg Phe Gly Val
305                 310                 315                 320

Leu Pro Arg Tyr Ser Lys Asn Asp Ala Leu Ile Lys Trp Phe Glu Leu
                325                 330                 335

Pro Asn Cys Phe Ile Phe His Asn Ala Asn Ala Trp Glu Glu Gly Asp
                340                 345                 350

Glu Val Ile Leu Ile Thr Cys Arg Leu Gln Asn Pro Asp Leu Asp Met
            355                 360                 365

Val Ser Gly Ile Val Lys Lys Leu Glu Asn Phe Ser Asn Glu Leu
        370                 375                 380

Tyr Glu Met Arg Phe Asn Leu Lys Thr Gly Leu Ala Ser Gln Lys Lys
385                 390                 395                 400

Leu Ser Glu Ser Ala Val Asp Phe Pro Arg Val Asn Glu Ser Tyr Thr
                405                 410                 415
```

-continued

Gly Arg Lys Gln Gln Tyr Val Tyr Gly Thr Ile Leu Asp Ser Ile Ala
                420                 425                 430

Lys Val Thr Gly Ile Ala Lys Phe Asp Leu His Ala Glu Pro Glu Thr
            435                 440                 445

Gly Lys Thr Lys Ile Glu Val Gly Gly Asn Val Gln Gly Val Phe Asp
        450                 455                 460

Leu Gly Pro Gly Arg Phe Gly Ser Glu Ala Ile Phe Val Pro Arg Gln
465                 470                 475                 480

Pro Gly Ile Thr Ser Glu Glu Asp Gly Tyr Leu Ile Phe Phe Val
                485                 490                 495

His Asp Glu Ser Thr Gly Lys Ser Ala Val Asn Val Ile Asp Ala Lys
                500                 505                 510

Thr Met Ser Ala Asp Pro Val Ala Val Val Glu Leu Pro Asn Arg Val
            515                 520                 525

Pro Tyr Gly Phe His Ala Phe Phe Val Thr Glu Glu Leu Glu Glu
        530                 535                 540

Gln Ala Lys Leu
545

<210> SEQ ID NO 22
<211> LENGTH: 320
<212> TYPE: PRT
<213> ORGANISM: Coffea canephora

<400> SEQUENCE: 22

Met Ala Ser Ile Thr Ser Phe Asn Gln Phe Ser Tyr Thr Val Lys Ser
1               5                   10                  15

Lys Thr Phe Gln His Pro Gln Phe Gly Thr Lys Val Ser Asn Ser Ala
                20                  25                  30

Val Asn Phe Thr Asp Phe Gly Leu Lys Lys Pro Leu Gln Ser Ser Ile
            35                  40                  45

Ser Ile Lys Glu Ser Ser Lys Lys Arg Pro Gly Phe Val Val Leu Val
        50                  55                  60

Ala Ala Gly Asp Asp Tyr Gly Pro Glu Glu Ala Ala Gly Val Ala
65                  70                  75                  80

Val Ala Glu Glu Pro Pro Lys Glu Pro Arg Glu Ile Asp Ile Leu
                85                  90                  95

Lys Lys Arg Leu Val Asp Ser Phe Tyr Gly Thr Asp Arg Gly Leu Asn
                100                 105                 110

Ala Ser Ser Glu Thr Arg Ala Glu Val Val Glu Leu Ile Thr Gln Leu
            115                 120                 125

Glu Ala Lys Asn Pro Thr Pro Ala Pro Thr Glu Ala Leu Thr Leu Leu
        130                 135                 140

Asn Gly Lys Trp Ile Leu Ala Tyr Thr Ser Phe Ile Gly Leu Phe Pro
145                 150                 155                 160

Leu Leu Ser Arg Gly Thr Leu Pro Leu Val Lys Val Glu Glu Ile Ser
                165                 170                 175

Gln Thr Ile Asp Ser Glu Ala Phe Ser Val Glu Asn Val Val Gln Phe
                180                 185                 190

Ala Gly Pro Leu Ala Thr Thr Ser Ile Thr Thr Asn Ala Lys Phe Glu
            195                 200                 205

Val Arg Ser Pro Lys Arg Val Gln Ile Lys Phe Glu Glu Gly Val Ile
        210                 215                 220

Gly Thr Pro Gln Leu Thr Asp Ser Ile Glu Leu Pro Glu Ser Val Glu
225                 230                 235                 240

```
Leu Leu Gly Gln Lys Ile Asp Leu Asn Pro Val Lys Gly Leu Leu Thr
            245                 250                 255

Ser Val Gln Asp Thr Ala Ser Ser Val Ala Lys Ser Ile Ser Ser Arg
        260                 265                 270

Pro Pro Leu Lys Phe Ser Leu Ser Asn Arg Asn Ala Glu Ser Trp Leu
            275                 280                 285

Leu Thr Thr Tyr Leu Asp Asp Glu Leu Arg Ile Ser Arg Gly Asp Gly
        290                 295                 300

Gly Ser Ile Phe Val Leu Ile Lys Glu Gly Cys Pro Leu Leu Lys Pro
305                 310                 315                 320

<210> SEQ ID NO 23
<211> LENGTH: 382
<212> TYPE: PRT
<213> ORGANISM: Coffea canephora

<400> SEQUENCE: 23

Lys Ser Ala Phe Trp Ala His Cys Met Arg Arg Ala Val Ser Met Gly
1               5                   10                  15

Gln Arg Glu Met Val Asp Phe Met Asp Leu Leu Leu Ser Pro Ala Ser
            20                  25                  30

Lys Val Leu Asn Asn Trp Phe Glu Thr Glu Val Leu Lys Ala Thr Leu
        35                  40                  45

Ala Thr Asp Ala Val Ile Gly Thr Thr Ala Ser Val His Thr Pro Gly
    50                  55                  60

Thr Gly Tyr Val Leu Leu His His Ile Met Gly Glu Thr Asp Gly Asp
65                  70                  75                  80

Arg Gly Ile Trp Ser Tyr Val Glu Gly Gly Met Gly Ser Val Ser Leu
                85                  90                  95

Ala Val Gly Ser Ala Ala Gln Glu Ala Gly Ala Thr Ile Val Thr Lys
            100                 105                 110

Ala Glu Val Ser Lys Leu Leu Ile Gly Asp Ser Gly Arg Val Asp Gly
        115                 120                 125

Val Leu Leu Pro Asp Gly Thr Glu Val Gln Ser Val Val Leu Ser
    130                 135                 140

Asn Ala Thr Pro Tyr Lys Thr Phe Met Glu Leu Val Pro Glu His Val
145                 150                 155                 160

Leu Pro Asp Asp Phe Leu Gln Ala Ile Lys Cys Ser Asp Tyr Ser Ser
                165                 170                 175

Ala Thr Thr Lys Ile Asn Leu Ala Val Glu Arg Val Pro Gln Phe Gln
            180                 185                 190

Cys Cys Lys Ile Asn His Pro Asn Ala Gly Pro Gln His Met Gly Thr
        195                 200                 205

Ile His Ile Gly Ser Glu Arg Met Glu Glu Val Asp Ser Ala Cys Gln
    210                 215                 220

Glu Ala Val Asn Gly Phe Pro Ser Lys Arg Pro Ile Ile Glu Met Thr
225                 230                 235                 240

Ile Pro Ser Val Leu Asp Lys Thr Ile Ser Pro His Gly Lys His Ile
                245                 250                 255

Ile Asn Leu Phe Ile Gln Tyr Thr Pro Tyr Lys Pro Leu Asp Gly Ser
            260                 265                 270

Trp Glu Asp Pro Ala Tyr Arg Glu Ser Phe Ala Gln Arg Cys Phe Ser
        275                 280                 285

Leu Ile Asp Asp Tyr Ala Pro Gly Phe Ser Ser Ser Ile Leu Gly Tyr
    290                 295                 300
```

```
Asp Met Leu Thr Pro Pro Asp Leu Glu Arg Glu Ile Gly Leu Thr Gly
305                 310                 315                 320

Gly Asn Ile Phe His Gly Ala Met Gly Leu Asp Ser Leu Phe Leu Met
                325                 330                 335

Arg Pro Val Lys Gly Trp Ser Asn Tyr Arg Thr Pro Val Gln Gly Leu
            340                 345                 350

Tyr Leu Cys Gly Ser Gly Ala His Pro Gly Gly Val Met Gly Ala
        355                 360                 365

Ala Gly Arg Asn Ala Ala Gly Thr Val Ile Gln Asp Trp Lys
    370                 375                 380
```

<210> SEQ ID NO 24
<211> LENGTH: 156
<212> TYPE: PRT
<213> ORGANISM: Coffea canephora

<400> SEQUENCE: 24

```
Glu Leu Leu Asp Gln Gly His Glu Val Asp Ile Tyr Glu Ser His Ser
1               5                   10                  15

Phe Ile Gly Gly Lys Val Gly Ser Phe Val Asp Lys Arg Gly Asn His
            20                  25                  30

Ile Gly Met Gly Leu His Val Phe Phe Gly Cys Tyr Asn Asn Leu Phe
        35                  40                  45

Arg Leu Met Lys Lys Val Gly Ala Asp Lys Asn Leu Val Lys Asp
    50                  55                  60

His Thr His Thr Phe Val Asn Lys Gly Gly Glu Ile Gly Glu Leu Asp
65                  70                  75                  80

Phe Arg Phe Pro Val Gly Ala Pro Leu His Gly Ile Asn Ala Phe Leu
                85                  90                  95

Ser Thr Asn Gln Leu Lys Ile Tyr Asp Lys Ala Arg Asn Ala Val Ala
            100                 105                 110

Leu Ala Leu Gly Pro Val Val Arg Ala Leu Val Asp Pro Asp Gly Ala
        115                 120                 125

Leu Arg Glu Ile Arg Asp Leu Asp Arg Ile Ser Phe Ser Asp Trp Phe
    130                 135                 140

Leu Ser Lys Gly Gly Thr Arg Ala Ser Ile Gln Arg
145                 150                 155
```

<210> SEQ ID NO 25
<211> LENGTH: 1143
<212> TYPE: DNA
<213> ORGANISM: Coffea canephora

<400> SEQUENCE: 25

```
cccgggctgg taaagtaata gatgagataa ttagaaagta cagaggaata actcttcatc     60
tggtctacaa gtacaagttt ttggataact gtcttatcta ttatatcttg gcatgtatgc    120
ctatgctcgt ccctaatact ttgtggtatt agtattagtt aggggggggg ggttcgaata    180
ttaaatacac atcataatgt ggaccattga caaaaggctc acttgcgtgc ctaaagtaaa    240
attaagaaaa ttaagccaaa gggcgatcct agttaactta actaccttag tagcctcact    300
ttttcatcca taacattttt ttttttttt ttataattcc tcccttgcac gatactcaac    360
tcaacccaac ccaactcaac attttgctga gttttaatta agtatttgaa agaacaaagg    420
caaaaaattc atcggaaata attttggtca ggtgtgtgtg tgattgttga gtagaatgaa    480
tcccgcgtcc aattggctga tggggtttgg gcattatatt attattatta ttattatcta    540
aagcgcgcta tattataggc tggggaaaga gagagaggtc gttggaggat gattcgtgtc    600
```

```
aaaggttgaa gaaaccatgt cccccgcccc tacccccac aaggtcaatg ctaattggca    660
aatcctccct tcgagcttct ctcttcctct tcccccaaat tttccattta tcaaacacgt    720
gggcttcacc tacacgttag aggtggcctc catccccaca cttccctcta tatatactct    780
ctctctcact cccttctttc ccccctcaa ggcacacaca cactcaaatc ctctactact    840
cctctataac cctctctctc tcaaatctct ctctctctca aaaactaaaa catttcaaaa    900
aaaaaaaaaa aaaaaaaac tccctactac tgccactgga cgacgacgac ttctactaca    960
ctagtagtcc atattggaaa atcaatcaat cgcaccaacg cgataaagat agcgaaaaac   1020 tcccccccc aaaaaaaaaa agccagtatg atccctgctt ccactcctac aaattcatat   1080
tcatgggtta atccaaaatc ccccatgccc atgaccatga ttttgcctcc ttcgtcaaga   1140
gag                                                                1143

<210> SEQ ID NO 26
<211> LENGTH: 28
<212> TYPE: DNA
<213> ORGANISM: Artificial Sequence
<220> FEATURE:
<223> OTHER INFORMATION: GWPSY1 primer

<400> SEQUENCE: 26
acttcaccgc agcgatcata agcttcac                                        28

<210> SEQ ID NO 27
<211> LENGTH: 27
<212> TYPE: DNA
<213> ORGANISM: Artificial Sequence
<220> FEATURE:
<223> OTHER INFORMATION: GWPSY2 primer

<400> SEQUENCE: 27
ttcacgtccc aatcttctcg agatctc                                         27

<210> SEQ ID NO 28
<211> LENGTH: 22
<212> TYPE: DNA
<213> ORGANISM: Artificial Sequence
<220> FEATURE:
<223> OTHER INFORMATION: AP1 primer

<400> SEQUENCE: 28
gtaatacgac tcactatagg gc                                              22

<210> SEQ ID NO 29
<211> LENGTH: 19
<212> TYPE: DNA
<213> ORGANISM: Artificial Sequence
<220> FEATURE:
<223> OTHER INFORMATION: AP2 primer

<400> SEQUENCE: 29
actatagggc acgcgtggt                                                  19

<210> SEQ ID NO 30
<211> LENGTH: 27
<212> TYPE: DNA
<213> ORGANISM: Artificial Sequence
<220> FEATURE:
<223> OTHER INFORMATION: GWVDE1 primer

<400> SEQUENCE: 30
acatttcttt cgtgagactg cacactc                                         27
```

```
<210> SEQ ID NO 31
<211> LENGTH: 28
<212> TYPE: DNA
<213> ORGANISM: Artificial Sequence
<220> FEATURE:
<223> OTHER INFORMATION: GWVDE2 primer

<400> SEQUENCE: 31
atcaccacat tgatctggc attcagtc                                          28

<210> SEQ ID NO 32
<211> LENGTH: 27
<212> TYPE: DNA
<213> ORGANISM: Artificial Sequence
<220> FEATURE:
<223> OTHER INFORMATION: VDEFWR primer

<400> SEQUENCE: 32
caccatggct tctgctttgc attcagc                                           27

<210> SEQ ID NO 33
<211> LENGTH: 22
<212> TYPE: DNA
<213> ORGANISM: Artificial Sequence
<220> FEATURE:
<223> OTHER INFORMATION: VDEREV primer

<400> SEQUENCE: 33
actaccttag cttcctaatt gg                                                22

<210> SEQ ID NO 34
<211> LENGTH: 28
<212> TYPE: DNA
<213> ORGANISM: Artificial Sequence
<220> FEATURE:
<223> OTHER INFORMATION: GWCCD11 primer

<400> SEQUENCE: 34
aacaatccga acagcccctt gagatccc                                          28

<210> SEQ ID NO 35
<211> LENGTH: 28
<212> TYPE: DNA
<213> ORGANISM: Artificial Sequence
<220> FEATURE:
<223> OTHER INFORMATION: GWCCD12 primer

<400> SEQUENCE: 35
gtttaagcct tgatgtcttc acgtaccg                                          28

<210> SEQ ID NO 36
<211> LENGTH: 27
<212> TYPE: DNA
<213> ORGANISM: Artificial Sequence
<220> FEATURE:
<223> OTHER INFORMATION: GWCCD13 primer

<400> SEQUENCE: 36
tgccaagtta ctgttcaatg actaggc                                           27

<210> SEQ ID NO 37
<211> LENGTH: 28
<212> TYPE: DNA
<213> ORGANISM: Artificial Sequence
<220> FEATURE:
<223> OTHER INFORMATION: GWCCD14 primer
```

-continued

```
<400> SEQUENCE: 37
aagcaattta atcccgtcct taatctgg                                      28

<210> SEQ ID NO 38
<211> LENGTH: 26
<212> TYPE: DNA
<213> ORGANISM: Artificial Sequence
<220> FEATURE:
<223> OTHER INFORMATION: CCD1FWR primer

<400> SEQUENCE: 38
caccatgggt aggcaagaag gagaag                                        26

<210> SEQ ID NO 39
<211> LENGTH: 22
<212> TYPE: DNA
<213> ORGANISM: Artificial Sequence
<220> FEATURE:
<223> OTHER INFORMATION: CCD1REV primer

<400> SEQUENCE: 39
actctccagg acatggtcca gc                                            22

<210> SEQ ID NO 40
<211> LENGTH: 27
<212> TYPE: DNA
<213> ORGANISM: Artificial Sequence
<220> FEATURE:
<223> OTHER INFORMATION: GWNCED3F primer

<400> SEQUENCE: 40
aagcagaagc agtcagggac ttctacc                                       27

<210> SEQ ID NO 41
<211> LENGTH: 26
<212> TYPE: DNA
<213> ORGANISM: Artificial Sequence
<220> FEATURE:
<223> OTHER INFORMATION: GWNCED3R primer

<400> SEQUENCE: 41
tatccagtac accgaatctt gacacc                                        26

<210> SEQ ID NO 42
<211> LENGTH: 28
<212> TYPE: DNA
<213> ORGANISM: Artificial Sequence
<220> FEATURE:
<223> OTHER INFORMATION: NCED3FWR primer

<400> SEQUENCE: 42
caccatgatg ggcttgggtt tgggttgc                                      28

<210> SEQ ID NO 43
<211> LENGTH: 25
<212> TYPE: DNA
<213> ORGANISM: Artificial Sequence
<220> FEATURE:
<223> OTHER INFORMATION: NCED3REV primer

<400> SEQUENCE: 43
tcacaagttt ctttcagttc caggc                                         25
```

```
<210> SEQ ID NO 44
<211> LENGTH: 25
<212> TYPE: DNA
<213> ORGANISM: Artificial Sequence
<220> FEATURE:
<223> OTHER INFORMATION: BCHYFWR primer

<400> SEQUENCE: 44
caccatggct gccggaattg ccgtc                                       25

<210> SEQ ID NO 45
<211> LENGTH: 22
<212> TYPE: DNA
<213> ORGANISM: Artificial Sequence
<220> FEATURE:
<223> OTHER INFORMATION: BCHYREV primer

<400> SEQUENCE: 45
caagttgcgt aagggttcat aa                                          22

<210> SEQ ID NO 46
<211> LENGTH: 22
<212> TYPE: DNA
<213> ORGANISM: Artificial Sequence
<220> FEATURE:
<223> OTHER INFORMATION: DegPDS2 FWR primer

<400> SEQUENCE: 46
ggtggaaagr tagctgcatg ga                                          22

<210> SEQ ID NO 47
<211> LENGTH: 24
<212> TYPE: DNA
<213> ORGANISM: Artificial Sequence
<220> FEATURE:
<223> OTHER INFORMATION: DegPDS2 REV primer

<400> SEQUENCE: 47
tgttacrgac atgtcagcat acac                                        24

<210> SEQ ID NO 48
<211> LENGTH: 7
<212> TYPE: PRT
<213> ORGANISM: Lycopersicon esculentum

<400> SEQUENCE: 48

Gly Gly Lys Val Ala Ala Trp
1               5

<210> SEQ ID NO 49
<211> LENGTH: 8
<212> TYPE: PRT
<213> ORGANISM: Lycopersicon esculentum

<400> SEQUENCE: 49

Val Tyr Ala Asp Met Ser Val Thr
1               5

<210> SEQ ID NO 50
<211> LENGTH: 27
<212> TYPE: DNA
<213> ORGANISM: Artificial Sequence
<220> FEATURE:
<223> OTHER INFORMATION: GWPDS1 primer

<400> SEQUENCE: 50
atcattgaat gctccttcca ctgcaac                                     27
```

```
<210> SEQ ID NO 51
<211> LENGTH: 27
<212> TYPE: DNA
<213> ORGANISM: Artificial Sequence
<220> FEATURE:
<223> OTHER INFORMATION: GWPDS2 primer

<400> SEQUENCE: 51
tcattaattc ctagttctcc aaacagg                                    27

<210> SEQ ID NO 52
<211> LENGTH: 21
<212> TYPE: DNA
<213> ORGANISM: Artificial Sequence
<220> FEATURE:
<223> OTHER INFORMATION: DegZDS1 FWR primer

<400> SEQUENCE: 52
ttgcaggcat gtcgactgct g                                          21

<210> SEQ ID NO 53
<211> LENGTH: 24
<212> TYPE: DNA
<213> ORGANISM: Artificial Sequence
<220> FEATURE:
<223> OTHER INFORMATION: DegZDS3 REV primer

<400> SEQUENCE: 53
gtgggatcct gttgcatatg ctct                                       24

<210> SEQ ID NO 54
<211> LENGTH: 8
<212> TYPE: PRT
<213> ORGANISM: Lycopersicon esculentum

<400> SEQUENCE: 54

Leu Ala Gly Met Ser Thr Ala Val
1               5

<210> SEQ ID NO 55
<211> LENGTH: 9
<212> TYPE: PRT
<213> ORGANISM: Lycopersicon esculentum

<400> SEQUENCE: 55

Met Trp Asp Pro Val Ala Tyr Ala Leu
1               5

<210> SEQ ID NO 56
<211> LENGTH: 24
<212> TYPE: DNA
<213> ORGANISM: Artificial Sequence
<220> FEATURE:
<223> OTHER INFORMATION: primer

<400> SEQUENCE: 56
cccacctgga gcctctattc tgtt                                       24

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
ccccgtcggc ctcaagtttc                                            20
```

```
<210> SEQ ID NO 58
<211> LENGTH: 23
<212> TYPE: DNA
<213> ORGANISM: Artificial Sequence
<220> FEATURE:
<223> OTHER INFORMATION: primer

<400> SEQUENCE: 58
tgatgaggca gagaaaggag tga                                          23

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
gatgcccata caggccatct                                              20

<210> SEQ ID NO 60
<211> LENGTH: 14
<212> TYPE: DNA
<213> ORGANISM: Artificial Sequence
<220> FEATURE:
<223> OTHER INFORMATION: PSY probe

<400> SEQUENCE: 60
cgagctcaac tctg                                                    14

<210> SEQ ID NO 61
<211> LENGTH: 24
<212> TYPE: DNA
<213> ORGANISM: Artificial Sequence
<220> FEATURE:
<223> OTHER INFORMATION: primer

<400> SEQUENCE: 61
tggtaaccct ccagagagac tttg                                         24

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
tctgcctcct cgtgactcaa                                              20

<210> SEQ ID NO 63
<211> LENGTH: 17
<212> TYPE: DNA
<213> ORGANISM: Artificial Sequence
<220> FEATURE:
<223> OTHER INFORMATION: PDS probe

<400> SEQUENCE: 63
atgccgattg ttgagca                                                 17

<210> SEQ ID NO 64
<211> LENGTH: 24
<212> TYPE: DNA
<213> ORGANISM: Artificial Sequence
<220> FEATURE:
<223> OTHER INFORMATION: primer
```

```
<400> SEQUENCE: 64
gctgataaaa atttgctcgt gaag                                              24

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
caccaatttc acccccttg                                                    20

<210> SEQ ID NO 66
<211> LENGTH: 20
<212> TYPE: DNA
<213> ORGANISM: Artificial Sequence
<220> FEATURE:
<223> OTHER INFORMATION: ZDS probe

<400> SEQUENCE: 66
atcatactca cacatttgtt                                                   20

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
aaacggagag ccacctgatg                                                   20

<210> SEQ ID NO 68
<211> LENGTH: 24
<212> TYPE: DNA
<213> ORGANISM: Artificial Sequence
<220> FEATURE:
<223> OTHER INFORMATION: primer

<400> SEQUENCE: 68
tgctcaatct ttacaaccca tttc                                              24

<210> SEQ ID NO 69
<211> LENGTH: 19
<212> TYPE: DNA
<213> ORGANISM: Artificial Sequence
<220> FEATURE:
<223> OTHER INFORMATION: PTOX probe

<400> SEQUENCE: 69
tcatcctcta gtggtttgg                                                    19

<210> SEQ ID NO 70
<211> LENGTH: 18
<212> TYPE: DNA
<213> ORGANISM: Artificial Sequence
<220> FEATURE:
<223> OTHER INFORMATION: primer

<400> SEQUENCE: 70
gccgcaagag aggaaacg                                                     18
```

```
<210> SEQ ID NO 71
<211> LENGTH: 23
<212> TYPE: DNA
<213> ORGANISM: Artificial Sequence
<220> FEATURE:
<223> OTHER INFORMATION: primer

<400> SEQUENCE: 71
gcaaaataag tgccaatcca aaa                                              23

<210> SEQ ID NO 72
<211> LENGTH: 15
<212> TYPE: DNA
<213> ORGANISM: Artificial Sequence
<220> FEATURE:
<223> OTHER INFORMATION: LeCY probe

<400> SEQUENCE: 72
cagagagcat tcttc                                                       15

<210> SEQ ID NO 73
<211> LENGTH: 16
<212> TYPE: DNA
<213> ORGANISM: Artificial Sequence
<220> FEATURE:
<223> OTHER INFORMATION: primer

<400> SEQUENCE: 73
cgccgtccct gccata                                                      16

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
aatgaggccc ttgtggaaga                                                  20

<210> SEQ ID NO 75
<211> LENGTH: 17
<212> TYPE: DNA
<213> ORGANISM: Artificial Sequence
<220> FEATURE:
<223> OTHER INFORMATION: BCHY probe

<400> SEQUENCE: 75
ccctcctttc ttatggc                                                     17

<210> SEQ ID NO 76
<211> LENGTH: 21
<212> TYPE: DNA
<213> ORGANISM: Artificial Sequence
<220> FEATURE:
<223> OTHER INFORMATION: primer

<400> SEQUENCE: 76
ttggttctga caaggctgca t                                                21

<210> SEQ ID NO 77
<211> LENGTH: 18
<212> TYPE: DNA
<213> ORGANISM: Artificial Sequence
<220> FEATURE:
<223> OTHER INFORMATION: primer
```

-continued

```
<400> SEQUENCE: 77
cgagaacggt ggctggtt                                              18

<210> SEQ ID NO 78
<211> LENGTH: 14
<212> TYPE: DNA
<213> ORGANISM: Artificial Sequence
<220> FEATURE:
<223> OTHER INFORMATION: ZEP probe

<400> SEQUENCE: 78
ccgggtaaag gtca                                                  14

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
ccccttgtcg agagattgga                                            20

<210> SEQ ID NO 80
<211> LENGTH: 23
<212> TYPE: DNA
<213> ORGANISM: Artificial Sequence
<220> FEATURE:
<223> OTHER INFORMATION: primer

<400> SEQUENCE: 80
acctccctta cgattgtcct ttc                                        23

<210> SEQ ID NO 81
<211> LENGTH: 17
<212> TYPE: DNA
<213> ORGANISM: Artificial Sequence
<220> FEATURE:
<223> OTHER INFORMATION: VDE probe

<400> SEQUENCE: 81
aagacagtgg aagaagg                                               17

<210> SEQ ID NO 82
<211> LENGTH: 21
<212> TYPE: DNA
<213> ORGANISM: Artificial Sequence
<220> FEATURE:
<223> OTHER INFORMATION: primer

<400> SEQUENCE: 82
cctaggacca ggaaggtttg g                                          21

<210> SEQ ID NO 83
<211> LENGTH: 16
<212> TYPE: DNA
<213> ORGANISM: Artificial Sequence
<220> FEATURE:
<223> OTHER INFORMATION: primer

<400> SEQUENCE: 83
ccaggctggc gtggaa                                                16
```

```
<210> SEQ ID NO 84
<211> LENGTH: 14
<212> TYPE: DNA
<213> ORGANISM: Artificial Sequence
<220> FEATURE:
<223> OTHER INFORMATION: CCD1 probe

<400> SEQUENCE: 84
cggaggctat cttt                                                      14

<210> SEQ ID NO 85
<211> LENGTH: 24
<212> TYPE: DNA
<213> ORGANISM: Artificial Sequence
<220> FEATURE:
<223> OTHER INFORMATION: primer

<400> SEQUENCE: 85
ggaaatcgga gcttagaatt gtca                                           24

<210> SEQ ID NO 86
<211> LENGTH: 22
<212> TYPE: DNA
<213> ORGANISM: Artificial Sequence
<220> FEATURE:
<223> OTHER INFORMATION: primer

<400> SEQUENCE: 86
cagctgcact gatgcctcta at                                             22

<210> SEQ ID NO 87
<211> LENGTH: 14
<212> TYPE: DNA
<213> ORGANISM: Artificial Sequence
<220> FEATURE:
<223> OTHER INFORMATION: NCED3 probe

<400> SEQUENCE: 87
cgccatgaca ttgg                                                      14

<210> SEQ ID NO 88
<211> LENGTH: 21
<212> TYPE: DNA
<213> ORGANISM: Artificial Sequence
<220> FEATURE:
<223> OTHER INFORMATION: primer

<400> SEQUENCE: 88
ctgtccagga cacagcatcc t                                              21

<210> SEQ ID NO 89
<211> LENGTH: 21
<212> TYPE: DNA
<213> ORGANISM: Artificial Sequence
<220> FEATURE:
<223> OTHER INFORMATION: primer

<400> SEQUENCE: 89
tcagtggtgg tcggctagaa a                                              21

<210> SEQ ID NO 90
<211> LENGTH: 13
<212> TYPE: DNA
<213> ORGANISM: Artificial Sequence
<220> FEATURE:
<223> OTHER INFORMATION: FIB1 probe
```

```
<400> SEQUENCE: 90
agtcgcaaag tcc                                                      13

<210> SEQ ID NO 91
<211> LENGTH: 21
<212> TYPE: DNA
<213> ORGANISM: Artificial Sequence
<220> FEATURE:
<223> OTHER INFORMATION: primer

<400> SEQUENCE: 91
gaacaggccc atcccttatt g                                             21

<210> SEQ ID NO 92
<211> LENGTH: 18
<212> TYPE: DNA
<213> ORGANISM: Artificial Sequence
<220> FEATURE:
<223> OTHER INFORMATION: primer

<400> SEQUENCE: 92
cggcgcttgg caattgta                                                 18

<210> SEQ ID NO 93
<211> LENGTH: 16
<212> TYPE: DNA
<213> ORGANISM: Artificial Sequence
<220> FEATURE:
<223> OTHER INFORMATION: RPL39 probe

<400> SEQUENCE: 93
atgcgcactg acaaca                                                   16
```

POLYNUCLEOTIDES ENCODING CAROTENOID AND APOCARTENOID BIOSYNTHETIC PATHWAY ENZYMES IN COFFEE

This is a U.S. National Phase of International Application No. PCT/US2006/034402, filed Sep. 1, 2006, which claims benefit of U.S. Provisional Application No. 60/714,106, filed Sep. 2, 2005, the entire contents of each of which are incorporated by reference herein.

FIELD OF THE INVENTION

The present invention relates to the field of agricultural biotechnology. In particular, the invention features polynucleotides from coffee plants that encode enzymes responsible for carotenoid and apocarotenoid synthesis, promoter sequences from coffee carotenoid genes, as well as methods for using these polynucleotides, polypeptides, and promoters for gene regulation and manipulation of flavor, aroma and other features of coffee beans.

BACKGROUND OF THE INVENTION

Various publications, including patents, published applications and scholarly articles, are cited throughout the specification. Each of these publications is incorporated by reference herein, in its entirety. Citations not fully set forth within the specification may be found at the end of the specification.

Coffee aroma and flavor are key components in consumer preference for coffee varieties and brands. The characteristic aroma and flavor of coffee stems from a complex series of chemical reactions involving flavor precursors (Maillard reactions) that occur during the roasting of the bean. Flavor precursors include chemical compounds and biomolecules present in the green coffee bean. To date, over 800 chemicals and biomolecules have been identified as contributing to coffee flavor and aroma. (Flament, I., 2002 "Coffee Flavor Chemistry" J. Wiley et al. U.K.) Because coffee consumers are becoming increasingly sophisticated, it is desirable to produce coffee with improved aroma and flavor in order to meet consumer preferences. Both aroma and flavor may be artificially imparted into coffee products through chemical means. See, for example, U.S. Pat. No. 4,072,761 (aroma) and U.S. Pat. No. 3,962,321 (flavor). However, to date, there is little information concerning the influence of natural coffee grain components such as polysaccharides, proteins, pigments, and lipids, on coffee aroma and flavor. One approach is to select varieties from the existing germplasm that have superior flavor characteristics. A disadvantage to this approach is that, frequently, the highest quality varieties also possess significant negative agronomics traits, such as poor yield and low resistance to diseases and environmental stresses. It is also possible to select new varieties from breeding trials in which varieties with different industrial and agronomic traits are crossed and their progeny are screened for both high quality and good agronomic performance. However, this latter approach is very time consuming, with one crossing experiment and selection over three growing seasons taking a minimum of 7-8 years. Thus, an alternative approach to enhancing coffee quality would be to use techniques of molecular biology to enhance those elements responsible for the flavor and aroma that are naturally found in the coffee bean, or to add aroma and flavor-enhancing elements that do not naturally occur in coffee beans. Genetic engineering is particularly suited to achieve these ends. For example, coffee proteins from different coffee species may be swapped. In the alternative, the expression of genes encoding naturally occurring coffee proteins that positively contribute to coffee flavor may be enhanced. Conversely, the expression of genes encoding naturally occurring coffee proteins that negatively contribute to coffee flavor may be suppressed.

Coffees from different varieties and origins exhibit significant flavor and aroma quality variations when the green grain samples are roasted and processed in the same manner. The quality differences are a manifestation of chemical and physical variations within the grain samples that result mainly from differences in growing and processing conditions, and also from differences in the genetic background of both the maternal plant and the grain. At the level of chemical composition, at least part of the flavor quality can be associated with variations in the levels of small metabolites, such as sugars, acids, phenolics, and caffeine found associated with grain from different varieties. It is accepted that there are other less well characterized flavor and flavor-precursor molecules. In addition, it is likely that structural variations within the grain also contribute to differences in coffee quality. One approach to finding new components in the coffee grain linked to coffee quality is to study the genes and proteins differentially expressed during the maturation of grain samples in different varieties that possess different quality characteristics. Similarly, genes and proteins that participate in the biosynthesis of flavor and flavor-precursor molecules may be studied.

Carotenoids are one candidate class of flavor and flavor precursor molecules. Carotenoids have been identified in all plants, as well as in a wide range of algae, certain fungi and bacteria (Fraser et al., 1999). Their 40-carbon structure confers particular properties, allowing them to absorb light between about 400 and 500 nm. Carotenoids are liphophilic, a characteristic that, along with their coloration, makes them sensitive to oxidative degradation (Britton, 1988). Carotenoids represent the largest group of pigments in nature, with some 600 different carotenoids identified to date (Cunningham and Grant, 1998). In fact, carotenoid-derived apocarotenoids conceivably constitute one of the largest classes of molecules in nature. Some of the apocarotenoids are essential and valuable constituents of color, flavor, and aroma in edible plants. (Winterhalter and Rouseff, 2002).

In plants, the carotenoid pigments are synthesized in the plastids. The biosynthetic pathway takes place on membranes in the plastid compartment of the cell, and the corresponding genes are located in the nucleus. In chloroplasts, carotenoids accumulate primarily in the photosynthetic membranes in association with the light-harvesting complexes. In the chromoplasts of ripening fruits and flower petals and in the chloroplasts of senescing leaves, the carotenoids may be found in membranes or in oil bodies such as plastoglobules, or in other structures within the stroma.

The first true carotenoid is formed by the condensation of two molecules of geranylgeranyl diphosphate into phytoene (FIG. 1A). This reaction is catalyzed by the enzyme phytoene synthase (geranylgeranyl-diphosphate geranylgeranyl transferase PSY; EC 2.5.1.32). Phytoene, which is not a true pigment since it is unable to absorb light at visible wavelengths, undergoes four consecutive desaturation steps. The first two steps are carried out by the enzyme phytoene desaturase (PDS; EC 1.3.99), resulting in the formation of ζ-carotene (FIG. 1B) via the intermediate phytofluene (Bartley et al., 1992; Hugueney et al., 1992). The second two steps are catalyzed by the enzyme ζ-carotene desaturase (ZDS; EC 1.14.99.30) to form lycopene (FIG. 1C) via the intermediate neurosporene (Albrecht et al., 1995). These desaturation steps require the presence of a plastid terminal oxidase (PTOX) as a co-factor (Carol et al., 1999; Josse et al, 2000; Josse et al., 2003; for review see Kuntz, 2004).

PDS and ZDS yield lycopene (FIG. 1C), the main pigment found in red tomatos. Lycopene serves as the substrate for the formation of both α- and β-carotene via two cyclization reactions. β-carotene (β,β-carotene) (FIG. 1D) is formed by the enzyme lycopene β-cyclase (LβCY; Cunningham et al., 1996), which introduces two β-ring structures at the ends of the carbon chain. This reaction also results in the formation of the intermediate γ-carotene (β,ψ-carotene) containing one β-ring and one uncyclized end, referred to as psi (ψ). Alpha-carotene (β,ε-carotene) (FIG. 1E) is formed by the enzymes lycopene ε-cyclase (LεCY; Ronen et al., 1999) and LβCY, which introduce one ε-ring and one β-ring respectively. The activity of LεCY also results in the formation of the intermediate δ-carotene (ε,ψ-carotene) having one ε-ring and one uncyclized psi end. In plants such as *Lactuca sativa* (lettuce), LεCY introduces two ε-ring structures at the ends of the carbon chain, resulting in the formation of ε-carotene (ε,ε-carotene; Cunningham and Gantt 2001) (FIG. 1F).

Oxygenated carotenoids are formed by two successive hydroxylation steps. β-carotene (β,β-carotene) is first converted to cryptoxanthine and then zeaxanthine (3,3'-dihydroxy-β,β-carotene) (FIG. 1G) by the action of the enzyme β-carotene hydroxylase (βCHY; EC 1.14.13-; Sandmann., 1994). Alpha-carotene (β,ε-carotene) is also twice hydroxylated; first the β-ring is hydroxylated by βCHY to form the intermediate zienoxanthine (FIG. 1M), and then the ε-ring is hydroxylated by ε-carotene hydroxylase (εCHY) to form lutein (dihydroxy-β,ε-carotene) (FIG. 1H). εCHY has only recently been cloned (Tian at al., 2004; Tian and DellaPenna, 2004; for review see Inoue, 2004), and a lutein deficient mutant (lut1) has been characterized (Pogson et al., 1996; Tian and DellaPenna, 2001).

The hydroxylated β-rings of zeaxanthine are epoxylated in two steps to give antheraxanthine (FIG. 1J) and violaxanthine (FIG. 1K). This reaction is catalyzed by the enzyme zeaxanthine epoxidase (ZEP; Marin et al., 1996; Bouvier et al., 1996). During light stress, violaxanthine can be converted back into antheraxanthine and zeaxanthine due to the activity of violaxanthine de-epoxidase (VDE). ZEP and VDE participate in the xanthophyll cycle, which is implicated in the adaptation of plastids to changing environmental light conditions (for review see Hieber et al., 2000).

Another carotenoid in higher plants is neoxanthine (FIG. 1L). Neoxanthine is synthesized from violaxanthine by a reaction catalyzed by neoxanthine synthase (NYS). NYS was originally cloned from tomato and potato (Bouvier et al., 2000; Al-Babili et al., 2000).

All of the carotenoid substrates described above are available for both oxidative and enxymatic cleavage resulting in the formation of diverse volatile and non-volatile apocarotenoids. Terpenoid flavor volatile compounds are generally present in plants at relatively low levels, but possess strong effects on the overall human appreciation of the flavor, for example, in tomatoes (Buttery et al., 1971 and 1987; Baldwin et al., 1991 and 2000), carrots (Kjeldsen et al., 2003), quince (Lutz and Winterhalter, 1992), and *Averrhoa carambola* (Winterhalter and Schreier, 1995). Among the more important carotenoid derived volatile compounds are β-ionone, α-ionone, geranylacetone (6,10-dimethyl-5,9-undecadien-2-one), pseudoionone (6,10-dimethyl-3,5,9-undecatrien-2-one) and β-damascenone. Alpha-ionone, β-ionone, β-cyclocitral, and β-damascenone have been shown to contribute approximately 8% of the total aroma intensity and 78% of the total floral aroma category of Valencia orange juice (Mahattanatawee et al., 2005). β-damascenone also contributes to the aroma of grapefruit juice (Lin et al., 2002).

Peak levels of β-ionone and geranylacetone emissions from ripe tomato fruit were calculated to be 1.25 pg/g fw$^{-1}$ hr$^{-1}$ and 40 pg/g fw$^{-1}$ hr$^{-1}$, respectively. Although β-ionone and geranylacetone are found in low concentrations when compared to other more abundant volatiles such as cis-3-hexenal and hexenal, which have been detected at levels 10,000-fold higher, β-ionone and geranylacetone have odor thresholds of 0.007 mL/L$^{-1}$ and 60 mL/L$^{-1}$ respectively (Baldwin et al., 2000). These odor thresholds are significantly lower than that observed for many of the other more abundant volatiles. Thus, carotenoid-derived volatiles have the potential to greatly impact aroma and flavor at low concentrations. β-ionone is considered to be the second most important volatile contributor to tomato fruit flavor (Baldwin et al., 2000).

The biosynthetic routes leading to the formation of apocarotenoid have remained obscure. Based on their chemical structures and studies of volatile production in tomato varieties with unusual carotenoid accumulation, Buttery et al. (1988) predicted that these compounds are likely derived from oxidative carotenoid cleavage. In recent years, a family of carotenoid cleavage dioxygenases (CCDs) that cleave carotenoid substrates at a variety of double bonds have been identified (for review see Bouvier et al., 2005). The first member of the family to be identified was VP14 from *Arabidopsis thaliana*, a 9-cis-epoxycarotenoid dioxygenase involved in synthesis of xanthoxin (FIG. 1N), the precursor of the phytohormone abscisic acid (ABA; Tan et al., 1997). ABA controls embryo growth potential and endosperm cap weakening during coffee seed germination (da Silva et al., 2004).

Other members of the dioxygenase family, including an *Arabidopsis* carotenoid cleavage dioxygenase, AtCCD1, that symmetrically cleaves the 9,10(9',10') double bonds of multiple carotenoid substrates into a C$_{14}$ dialdehyde and two C$_{13}$ cyclohexone derivatives in vitro have been identified (Schwartz et al., 2001). Orthologs of AtCCD1 have been found in a variety of species including *Phaseolus vulgaris* (Schwartz et al., 2001), *Capsicum annuum* (Bouvier et al., 2003a), *Crocus sativus* (Bouvier et al., 2003a) and *Petunia hybrida* (Simkin et al., 2004a). More recently, Simkin et al. (2004b) demonstrated in transgenic tomato plants that CCD1 enzymes are responsible for the formation of a variety of C$_{13}$ cyclohexones in vivo. The potential relationships between these volatiles and their carotenoid precursors are shown in FIG. 2. Carotenoid cleaved at the 9,10(9',10") bond results in the formation of the corresponding apocarotenoid. Because CCD1 enzymes have 9,10(9',10") cleavage specificities, specific products would be generated based on the carotenoid precursor that is present. AtCCD1 and its tomato orthologues are responsible for the formation of geranylacetone and α-ionone (Schwartz et al., 2001; Simkin et al., 2004a and 2004b) and likely β-damascenone (Suzuki et al., 2002). Schwartz et al. (2001) and Simkin et al. (2004b) showed that CCD1s were also capable of forming a number of other important carotenoid-derived volatiles Schwartz et al. (2001) and Simkin et al. (2004b) purified recombinant AtCCD1 and LeCCD1A enzyme respectively and assayed multiple carotenoid substrates in vitro. The assay products were characterized by thin-layer chromatography and HPLC. In assays containing either β-carotene, zeaxanthine, lutein, violaxanthine and neoxanthine, the central C$_{14}$ dialdehyde cleavage product (4,9-dimethyldodeca-2,4,6,8,10-pentaene-1,12-dial; I) was the major compound resulting from symmetrical cleavage at the 9,10 and 9',10' positions (see FIG. 2). In assays containing β-carotene, zeaxanthine and lycopene, β-ionone (9-apo-β-caroten-9-one; II), 3-hydroxy-β-ionone (3-hydroxy-9-apo-β-caroten-9-one; III) and pseudoionone (V) were formed respectively, whereas α-carotene led to the production of both β-ionone (II) and α-ionone (VI), while δ-carotene led to α-ionone (9-apo-α-caroten-9-one; VI) and pseudoionone (6,10-dimethyl-3,5,9-undecatrien-2-one; V). In assays containing violaxanthine or neoxanthine, 5'6-epoxy-3-hydroxy-β-ionone (5,6-epoxy-3-hydroxy-9-apo-β-caroten-9-one; IV) was formed. Asymmetric cleavage also led to the formation of a $C_{27}$ epoxy-apocarotenal with these substrates. Several linear carotenoids including phytoene and ζ-carotene are thought to be the precursors of geranylacetone (6,10-dimethyl-5,9-undecatrien-2-one; VII), an important flavor volatile in tomato fruit, and precursors for a second $C_{14}$ dialdehyde (4,9-dimethyldodeca-4,6,8-triendial; XI).

In assays containing neoxanthine, the asymmetric cleavage also led to the formation of a $C_{27}$ allenic-apocarotenal and the $C_{13}$ grasshopper ketone (3,5-dihdroxy-6,7-didehydro-9-apo-β-caroten-9-one; VIII) (see FIG. 3a). The grasshopper ketone is postulated to be the precursor for the formation of β-damascenone (IX) and 3-hydroxy-β-damascenone (X; Suzuki et al., 2002). In assays containing lutein as substrate, symmetrical cleavage at the 9,10 and 9',10' positions leads to the formation of both 3-hydroxy-β-ionone (VI) and 3-hydroxy-α-ionone.

Additionally, Bouvier et al (2003b) identified a zeaxanthine-specific 7,8(7',8')-cleavage dioxygenase (CsZCD) from *Crocus sativus* encoding an enzyme capable of forming of crocetin dialdehyde (XII) and 3-hydroxy-β-cyclocitral in vitro (XIII; see FIG. 3b). Crocetin dialdehyde is known to accumulate in the flowers of *Jacquinia angustifolia* (Eugster et al., 1969) and the roots of *Coleus forskohlii* (Tandon et al., 1979). 3-hydroxy-β-cyclocitral is believed to be the first committed step in the formation of safranal, a constituent of the spice saffron in *C. sativus* (Bouvier et al., 2003a). The 7,8(7',8')-cleavage of β-carotene by a tomato ZCD orthologue is suspected of being responsible for the formation of β-cyclocitral, contributing to tomato aroma. Bouvier et al. (2003b) have also identified a lycopene-specific 5,6(5',6')-cleavage dioxygenase (BoLCD) from *Bixa orellana* (see FIG. 3c), responsible for the formation of bixin dialdehyde (XIV) and a $C_7$ cleavage product previously identified as 6-methyl-5-hepten-2-one (MHO; XV; Fay et al., 2003). Bixin dialdehyde is the precursor for the formation of the dye bixin/annatto. MHO has been identified as an important contributor to tomato flavor (Buttery et al., 1990; Baldwin et al., 2000).

Despite this extensive knowledge, little work has been done to characterize such volatile molecules in green and roasted coffee. Roasted and un-roasted coffee has been shown to contain two carotenoid derived flavor components, α-ionone and β-damascenone (Czemy et al., 2000; Akiyama et al., 2003; Variyar et al., 2003). The latter component has been identified as a major component of coffee both before and after roasting (Ortiz et al., 2004). These and other carotenoid derived volatile compounds, due to their low odor threshold, require only small amounts to cause a change in aroma.

From the foregoing discussion, it will be appreciated that modulating carotenoid and apocarotenoid content in coffee grain by genetically modulating the production of the proteins responsible for carotenoid and apocarotenoid biosynthesis would be of great utility to enhance the aroma and flavor of coffee beverages and coffee products produced from such genetically engineered coffee beans. Enhanced carotenoid and apocarotenoid content in the coffee bean may also positively contribute to the overall health and wellness of consumers of coffee beverages and products produced from such coffee beans. In addition, modulating carotenoid and apocarotenoid content in the coffee plant has implications for optimizing photosynthesis in conditions of excess or insufficient sunlight. Accordingly, a need exists to identify, isolate and utilize genes and enzymes from coffee that are involved in the biosynthesis of carotenoids and apocarotenoids.

SUMMARY OF THE INVENTION

The invention described herein features genes encoding enzymes responsible for carotenoid and apocarotenoid biosynthesis in coffee plants, their encoded polypeptides, promoter sequences from coffee carotenoid and apocarotenoid biosynthetic pathway enzyme genes, and methods for using these polynucleotides, polypeptides and promoters for gene regulation and manipulation of flavor, aroma and other features of coffee beans.

One aspect of the invention features a nucleic acid molecule isolated from coffee (*Coffea* spp.), having a coding sequence that encodes a carotenoid or apocarotenoid biosynthetic pathway enzyme. In one embodiment, the enzyme is a phytoene synthase that is at least 76% identical to SEQ ID NO:13. In another embodiment, the enzyme is a phytoene desaturase that is at least 76% identical to SEQ ID NO:14. In another embodiment, the enzyme is a plastid terminal oxidase that is at least 61% identical to SEQ ID NO:15. In another embodiment, the enzyme is a β-carotene hydroxylase that is at least 73% identical to SEQ ID NO:16. In another embodiment, the enzyme is a lycopene s-cyclase that is at least 86% identical to SEQ ID NO:17. In another embodiment, the enzyme is a zeaxanthine epoxidase that is at least 26% identical to SEQ ID NO:18. In another embodiment, the enzyme is a violaxanthine de-epoxidase that is at least 74% identical to SEQ ID NO:19. In another embodiment, the enzyme is a 9-cis-epoxycarotenoid dioxygenase that is at least 75% identical to SEQ ID NO:20. In another embodiment, the enzyme is a carotenoid cleavage dioxygenase that is at least 83% identical to SEQ ID NO:21. In another embodiment, the enzyme is a fibrillin that is at least 72% identical to SEQ ID NO:22. In another embodiment, the enzyme is a phytoene dehydrogenase-like enzyme that is at least 72% identical to SEQ ID NO:23. In another embodiment, the enzyme is a zeta-carotene desaturase that is at least 82% identical to SEQ ID NO:24.

In certain embodiments, the nucleic acid molecule is a gene having an open reading frame that comprises the coding sequence. Alternatively, it may comprise an mRNA molecule produced by transcription of that gene, or a cDNA molecule produced by reverse transcription of the mRNA molecule. The invention also features an oligonucleotide between 8 and 100 bases in length, which is complementary to a segment of the aforementioned nucleic acid molecule.

Another aspect of the invention features a vector comprising the above-described carotenoid or apocarotenoid biosynthetic pathway enzyme-encoding nucleic acid molecules. In certain embodiments, the vector is an expression vector selected from the group of vectors consisting of plasmid, phagemid, cosmid, baculovirus, bacmid, bacterial, yeast and viral vectors. In certain embodiments, the vector contains the coding sequence of the nucleic acid molecule operably linked to a constitutive promoter. In other embodiments, the coding sequence is operably linked to an inducible promoter. In other embodiments, the coding sequence of the nucleic acid molecule is operably linked to a tissue specific promoter, such as a seed specific promoter, preferably a coffee seed specific promoter. In specific embodiments, the tissue specific promoter is a coffee carotenoid or apocarotenoid biosynthetic pathway enzyme-gene promoter, such as the promoter contained in SEQ ID NO:25.

According to another aspect of the invention, a host cell transformed with the aforementioned vector is provided. The host cell may be a plant, bacterial, fungal, insect or mammalian cell. In certain embodiments, the host cell is a plant cell selected from any one of coffee, tobacco, *Arabidopsis*, maize, wheat, rice, soybean barley, rye, oats, sorghum, alfalfa, clover, canola, safflower, sunflower, peanut, cacao, tomato tomatillo, potato, pepper, eggplant, sugar beet, carrot, cucumber, lettuce, pea, aster, begonia, chrysanthemum, delphinium, zinnia, and turfgrasses. The invention also features a fertile transgenic plant produced by regenerating the transformed plant cell. In a specific embodiment, the fertile transgenic plant is a *Coffea* species.

Another aspect of the invention features a method to modulate flavor or aroma of coffee beans. The method comprises modulating production of one or more caroteonid or apocarotenoid biosynthetic pathway enzymes within coffee seeds. In some embodiments, the method comprises increasing production of the one or more caroteonid or apocarotenoid biosynthetic pathway enzymes, e.g., by increasing expression of one or more endogenous caroteonid or apocarotenoid biosynthetic pathway enzyme-encoding genes within the coffee seeds, or by introducing a caroteonid or apocarotenoid biosynthetic pathway enzyme-encoding transgene into the plant. In other embodiments, the method comprises decreasing production of the one or more caroteonid or apocarotenoid biosynthetic pathway enzymes, e.g., by introducing a nucleic acid molecule into the coffee that inhibits the expression of one or more of the caroteonid or apocarotenoid biosynthetic pathway enzyme-encoding genes.

Another aspect of the invention features a method to modulate photosynthesis in a plant, especially in conditions of excess or insufficient light, comprising modulating production of one or more polypeptides that comprise the carotenoid or apocarotenoid biosynthetic pathway within coffee seeds. This method comprises increasing production of one or more caroteonid or apocarotenoid biosynthetic pathway enzymes within the plant, e.g., by increasing expression of one or more endogenous caroteonid or apocarotenoid biosynthetic pathway enzyme-encoding genes within the coffee seeds, or by introducing a caroteonid or apocarotenoid biosynthetic pathway enzyme-encoding transgene into the plant.

According to another aspect of the invention, a promoter isolated from a caroteonid or apocarotenoid biosynthetic pathway enzyme-encoding coffee plant gene is provided. In certain embodiments, the caroteonid or apocarotenoid biosynthetic pathway enzyme-encoding coffee gene encodes a caroteonid or apocarotenoid biosynthetic pathway enzyme having the one or more of the features described above. In certain embodiments, the promoter comprises one or more regulatory sequences selected from the group consisting of a TATA box, an abscisic acid responsive element, an RY repeat (CATGCA(T/a)(A/g) of a leguminin box for regulating expression of leguminin-type proteins, at least one dehydration responsive element/C-repeat cis-acting sequence motif (G/ACCGAC) and at least one E-box motif (CANNTG). In a specific embodiment, the promoter comprises SEQ ID NO:25.

The invention also features a chimeric gene comprising a promoter of a coffee carotenoid or apocarotenoid biosynthetic pathway enzyme-encoding gene, operably linked to one or more coding sequences. A vector for transforming a cell, comprising the chimeric gene, is also provided, as well as cells transformed with the vector and fertile transgenic plants produced by regenerating a plant cell transformed with the vector.

Other features and advantages of the present invention will be understood from the drawings, detailed description and examples that follow.

BRIEF DESCRIPTION OF THE DRAWINGS

FIG. 1. Overview of the biosynthesis of isoprenoids in plastids. Schematic of biosynthetic pathway for plant carotenoids. Abbreviations used are as follows: PSY: Phytoene synthase. PDS: phytoene desaturase ZDS: ζ-carotene desaturase. PTOX: plastid terminal oxidase. LβCY: lycopene β-cyclase. LεCY: lycopene ε-cyclase. βCHY: β-carotene hydroxylase. εCHY: ε-carotene hydroxylase. ZEP: zeaxanthine epoxidase. VDE: violaxanthine de-epoxidase. NYS: neoxanthine synthase. CCD1: carotenoid cleavage dioxygenase 1. FIB: CCD4: carotenoid cleavage dioxygenase 4. Fibrillin. NCED3: 9-cis-epoxycarotenoid dioxygenase. PDHY: phytoene dehydrogenase-like.

A) Transcript levels of CCD1 in the grain of three *C. canephora* genotypes, (BP409, FRT05, FRT64; black bars) and *C. arabica* (T2308; grey bars) determined by quantitative PCR. Reverse transcription was carried out with equal amounts of total RNA. SG, Small green grain; LG, large grain; YG, yellow grain; RG, ripe grain.

B) Activity of CCD1 following over-expression in *E. coli* previously engineered to accumulate lycopene, β-carotene or zeaxanthine. NI, non-induced; I, induced.

C) HPLC characterisation of Lyc, β-C and Zea lines before and after induction. The arrow indicates the loss of the carotenoid peak following induction of CCD1. Astaxanthin (⊙) was added to samples and used to normalise results.

FIG. 7. Activity of βCHY in *E. coli* previously engineered to accumulate β-carotene or zeaxanthine. A) *E. coli* lines engineered to accumulate β-carotene or zeaxanthin transformed with pDEST17-CcβCHY either before (NI); or after (I), induction. B) HPLC characterization of α-carotene producing cell lines before and after induction. β-C, β-carotene; zea, zeaxanthin.

Figure 8A:
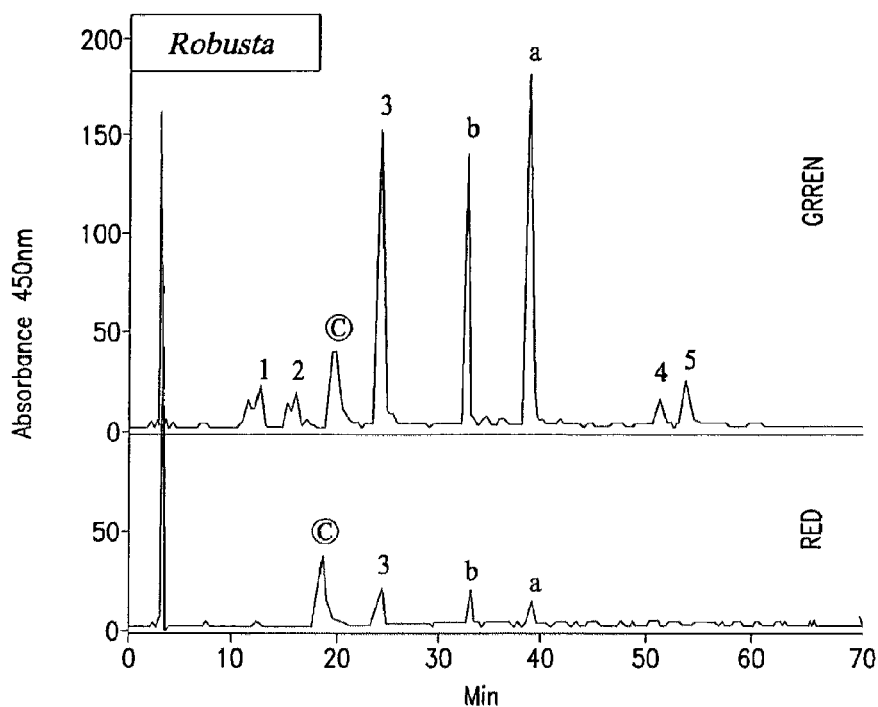
Figure 8B:
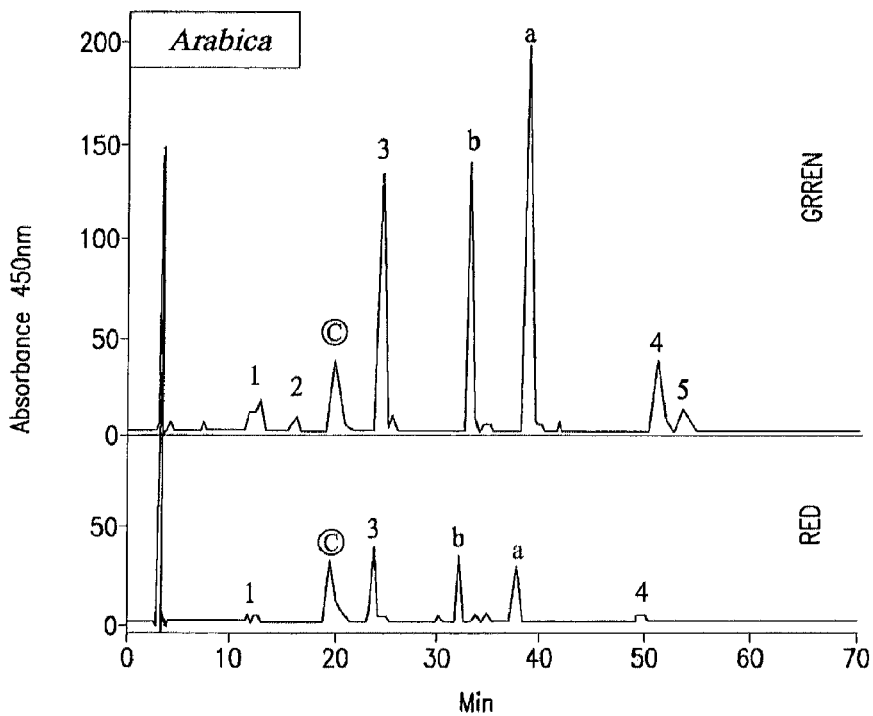

FIG. 8. HPLC analysis of *Coffea canphora* and *C. arabica* green and red grain. Absorbance profiles at 450 nm. Peaks are: (1) neoxanthin, (2) violaxanthin, (3) lutien, (4) α-carotene, (5) β-carotene, (a) chlorophyll A, (b) chlorophyll B. Astaxanthin (⊙) was added prior to extraction and used to normalise results. Green=grain from large green pericarp stage (LG). Red=grain from mature red pericarp stage (RG).

Figure 9A:
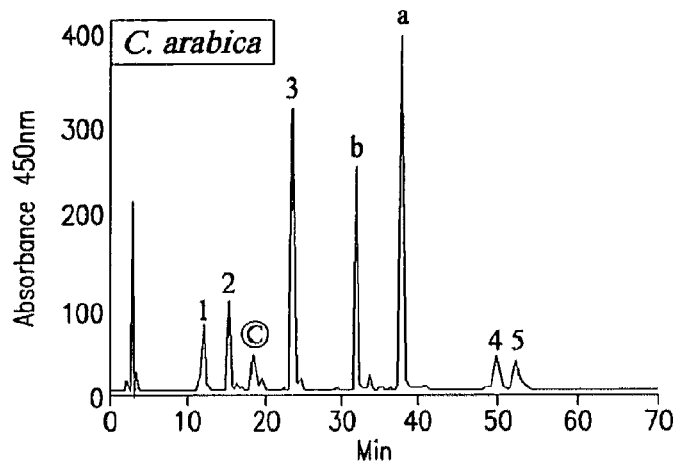
Figure 9B:
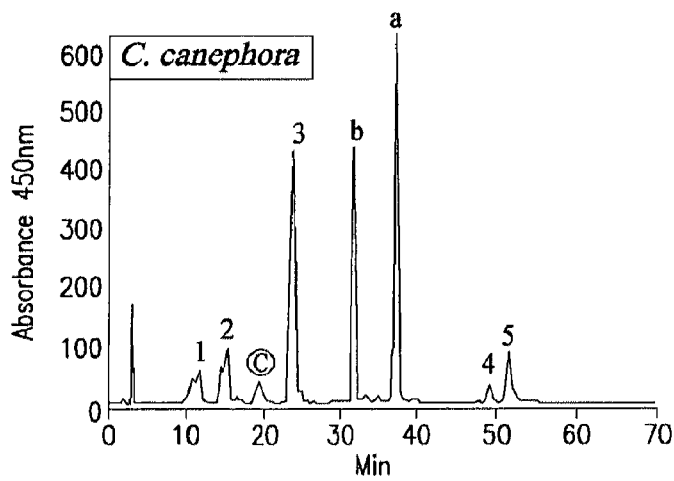

FIG. 9. HPLC analysis of *Coffea arabica, C. canephora* and *Arabidopsis thaliana* mature leaves. Absorbance was monitored at 450 nm. 60 mg samples were extracted as described in materials and methods. Peaks are: (1) neoxanthin, (2) violaxanthin, (3) lutein, (4) α-carotene, (5) β-carotene, (a) chlorophyll A, (b) chlorophyll B. Astaxanthin (⊙) was added to coffee samples prior to extraction and used to normalise results.

Figure 10:
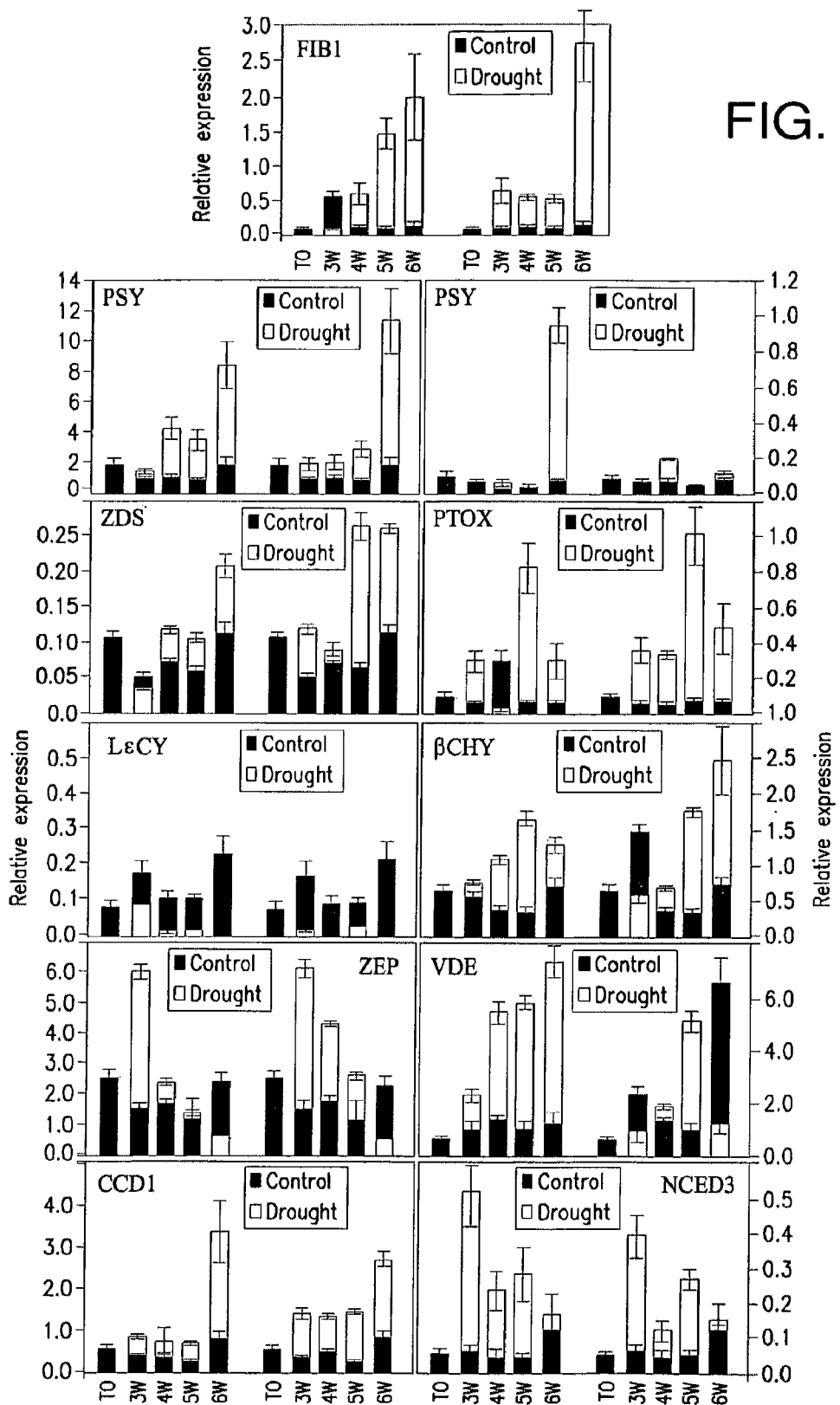

FIG. 10. Expression of carotenoid biosynthetic genes and carotenoid cleavage dioxygenase genes in the leaves of *Coffea arabica* (catimor) under drought stress. Transcript levels for PSY, PDS, ZDS, PTOX, LϵCY, βCHY, ZEP, VDE, CCD1, NCED3 and FIB1 were determined by quantitative RT-PCR. Expression was determined relative to the expression of transcripts of the constitutively expressed RPL39 gene in the same samples. The black bars in each case represent the mean transcript levels in two well-watered controls. Transcript levels in two independent water-stressed plants are shown in grey bars.

DETAILED DESCRIPTION OF ILLUSTRATIVE EMBODIMENTS

Definitions

Various terms relating to the biological molecules and other aspects of the present invention are used throughout the specification and claims.

The term "carotenoid and apocarotenoid biosynthetic pathway" refers to polypeptides that participate in carotenoid or apocarotenoid biosynthesis in plants, and more specifically, in coffee plants. This term encompasses the specific mechanism of action of each respective protein in the pathway, including the enzyme-mediated derivation of apocarotenoids from carotenoids. The polypeptides include without limitation, phytoene synthase, phytoene desaturase, ζ-carotene desaturase, plastid terminal oxidase, lycopene β-cyclase, lycopene ϵ-cyclase, β-carotene hydroxylase, ϵ-carotene hydroxylase, zeaxanthine epoxidase, violaxanthine de-epoxidase, neoxanthine synthase, carotenoid cleavage dioxygenase 1, carotenoid cleavage dioxygenase 4, Fibrillin, 9-cis-epoxycarotenoid dioxygenase, phytoene dehydrogenase, and the like, as exemplified herein.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

"Polynucleotide," also referred to as "nucleic acid molecule", generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., Analysis for Protein Modifications and Nonprotein Cofactors, Meth Enzymol (1990) 182:626-646 and Rattan et al., Protein Synthesis: Posttranslational Modifications and Aging, Ann NY Acad Sci (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions, fusions or truncations in any combination. A substituted or inserted amino acid residue may or may not be one encoded by the genetic code. A variant of a polynucleotide or polypeptide may be naturally occurring, such as an allelic variant, or it may be a variant that is not known to occur naturally. Non-naturally occurring variants of polynucleotides and polypeptides may be made by mutagenesis techniques or by direct synthesis.

In reference to mutant plants, the terms "null mutant" or "loss-of-function mutant" are used to designate an organism or genomic DNA sequence with a mutation that causes a gene product to be non-functional or largely absent. Such mutations may occur in the coding and/or regulatory regions of the gene, and may be changes of individual residues, or insertions or deletions of regions of nucleic acids. These mutations may also occur in the coding and/or regulatory regions of other genes, which may regulate or control a gene and/or encoded protein, so as to cause the protein to be non-functional or largely absent.

The term "substantially the same" refers to nucleic acid or amino acid sequences having sequence variations that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

"Identity" and "similarity" can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

"Antibodies" as used herein includes polyclonal and monoclonal antibodies, chimeric, single chain, and humanized antibodies, as well as antibody fragments (e.g., Fab, Fab', $F(ab')_2$ and $F_v$), including the products of a Fab or other immunoglobulin expression library. With respect to antibodies, the term, "immunologically specific" or "specific" refers to antibodies that bind to one or more epitopes of a protein of interest, but which do not substantially recognize and bind other molecules in a sample containing a mixed population of antigenic biological molecules. Screening assays to determine binding specificity of an antibody are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, and the like).

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, when the sequence is expressed. The coding sequence may comprise untranslated sequences (e.g., introns) within translated regions, or may lack such intervening untranslated sequences (e.g., as in cDNA).

"Intron" refers to polynucleotide sequences in a nucleic acid that do not code information related to protein synthesis. Such sequences are transcribed into mRNA, but are removed before translation of the mRNA into a protein.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene". Such a nucleic acid construct may contain a coding sequence for a gene product of interest, along with a selectable marker gene and/or a reporter gene.

A "marker gene" or "selectable marker gene" is a gene whose encoded gene product confers a feature that enables a cell containing the gene to be selected from among cells not containing the gene. Vectors used for genetic engineering typically contain one or more selectable marker genes. Types of selectable marker genes include (1) antibiotic resistance genes, (2) herbicide tolerance or resistance genes, and (3) metabolic or auxotrophic marker genes that enable transformed cells to synthesize an essential component, usually an amino acid, which the cells cannot otherwise produce.

A "reporter gene" is also a type of marker gene. It typically encodes a gene product that is assayable or detectable by standard laboratory means (e.g., enzymatic activity, fluorescence).

The term "express," "expressed," or "expression" of a gene refers to the biosynthesis of a gene product. The process involves transcription of the gene into mRNA and then translation of the mRNA into one or more polypeptides, and encompasses all naturally occurring post-translational modifications.

"Endogenous" refers to any constituent, for example, a gene or nucleic acid, or polypeptide, that can be found naturally within the specified organism.

A "heterologous" region of a nucleic acid construct is an identifiable segment (or segments) of the nucleic acid molecule within a larger molecule that is not found in association with the larger molecule in nature. Thus, when the heterologous region comprises a gene, the gene will usually be flanked by DNA that does not flank the genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Grain," "seed," or "bean," refers to a flowering plant's unit of reproduction, capable of developing into another such plant. As used herein, especially with respect to coffee plants, the terms are used synonymously and interchangeably.

As used herein, the term "plant" includes reference to whole plants, plant organs (e.g., leaves, stems, shoots, roots), seeds, pollen, plant cells, plant cell organelles, and progeny thereof. Parts of transgenic plants are to be understood within the scope of the invention to comprise, for example, plant cells, protoplasts, tissues, callus, embryos as well as flowers, stems, seeds, pollen, fruits, leaves, or roots originating in transgenic plants or their progeny.

Description:

In one of its aspects the present invention features nucleic acid molecules from coffee that encode a variety of proteins involved in the carotenoid and apocarotenoid biosynthetic pathway. Representative examples of nucleic acid molecules encoding proteins that comprise the carotenoid and apocarotenoid biosynthetic pathway were identified from databases of over 47,000 expressed sequence tags (ESTs) from several *Coffea canephora* (robusta) cDNA libraries made with RNA isolated from young leaves and from the grain and pericarp tissues of cherries harvested at different stages of development. Overlapping ESTs were identified and "clustered" into unigenes (contigs) comprising complete coding sequences. The unigene sequences were annotated by performing a BLAST search of each individual sequence against the NCBI (National Center for Biotechnology Information) non-redundant protein database.

BLAST searches of the coffee EST databases using biochemically characterized protein sequences from public databases revealed gene sequences representing several important enzymes of the carotenoid biosynthetic pathway in the coffee plant, and sequences coding for two enzymes (NCED3 and CCD1) that participate in the generation of apocarotenoids. The full open reading frames (ORFs) of several of these sequences were obtained, and a partial sequence of two other carotenoid biosynthetic enzyme (PDS and ZDS) was also cloned using degenerate primers and non-degenerate primers. These cDNAs and their encoded proteins are referred to herein as follows:

herein, this invention is intended to encompass nucleic acids and encoded proteins from other *Coffea* species that are sufficiently similar to be used interchangeably with the *C. canephora* polynucleotides and proteins for the purposes described below. Accordingly, when the term polypeptides or proteins that "comprise the carotenoid and apocarotenoid biosynthetic pathway" is used herein, it is intended to encompass all *Coffea* proteins that have the general physical, biochemical, and functional features described herein, as well as the polynucleotides that encode them.

Considered in terms of their sequences, the polynucleotides of the invention that encode proteins that comprise the carotenoid and apocarotenoid biosynthetic pathway include allelic variants and natural mutants of SEQ ID NOs: 1-12, which are likely to be found in different varieties of *C. canephora*, and homologs of SEQ ID NOs: 1-12 likely to be found in different coffee species. Because such variants and homologs are expected to possess certain differences in nucleotide and amino acid sequence, this invention provides isolated polynucleotides encoding proteins that comprise the carotenoid and apocarotenoid biosynthetic pathway that have at least about 60%, preferably at least about 61%, 62%, 63%, 64%, 65%, 66%, 67%, 68%, 69% or 70%, more preferably at least about 71%, 72%, 73%, 74%, 75%, 76%, 77%. 78%, 79%, or 80%, even more preferably 81%, 82%, 83%, 84%, 85%, 86%, 87%, 88%, 89%, and even more preferably 90%, 91%, 92%, 93%, 94%, 95%, and most preferably 96%, 97%, 98% and 99% or more identity with any one of SEQ ID NOs:13-24, and comprise a nucleotide sequence having equivalent ranges of identity to any one of SEQ ID NOs:1-12. Because of the natural sequence variation likely to exist among proteins that comprise the carotenoid and apocarotenoid biosynthetic pathway, and the genes encoding them in different coffee varieties and species, one skilled in the art would expect to find this level of variation, while still maintaining the unique properties of the polypeptides and polynucleotides of the present invention. Such an expectation is due in part to the degeneracy of the genetic code, as well as to the known evolutionary success of conservative amino acid

| Enzyme | cDNA | (SEQ ID NO:) | encoded protein | (SEQ ID NO:) |
|---|---|---|---|---|
| Phytoene synthase | CcPSY | 1 | CcPSY | 13 |
| Phytoene desaturase | CcPDS | 2 | CcPDS | 14 |
| Plastid terminal oxidase | CcPTOX | 3 | CcPTOX | 15 |
| β-carotene hydroxylase | CcβCHY | 4 | CcβCHY | 16 |
| Lycopene ε-cyclase | CcLεCY | 5 | CcLεCY | 17 |
| Zeaxanthine epioxidase | CcZEP | 6 | CcZEP | 18 |
| Violaxanthine de-epoxidase | CcVDE | 7 | CcVDE | 19 |
| 9-cis-epoxycarotenoid dioxygenase | CcNCED3 | 8 | CcNCED3 | 20 |
| Carotenoid cleavage dioxygenase | CcCCD1 | 9 | CcCCD1 | 21 |
| Fibrillin | CcFIB | 10 | CcFIB | 22 |
| Phytoene dehydrogenase-like | CcPDH | 11 | CcPDH | 23 |
| Zeta-carotene desaturase | CcZDS | 12 | CcZDS | 24 |
| | Promoter Region (SEQ ID NO:) | | | |
| Promoter CcNCED3 | pNCED3 | 25 | | |

Another aspect of the invention features promoter sequences and related elements that control expression of carotenoid and apocarotenoid biosynthetic pathway genes in coffee. As described in greater detail in the examples, a promoter sequence (contained in SEQ ID NO:25), from CcNCED3 was identified by PCR-assisted primer walking, as described in the examples.

Although polynucleotides encoding proteins that catalyze key steps the carotenoid and apocarotenoid biosynthetic pathway from *Coffea canephora* are described and exemplified sequence variations, which do not appreciably alter the nature of the encoded protein. Accordingly, such variants and homologs are considered substantially the same as one another and are included within the scope of the present invention.

The gene regulatory sequences associated with genes encoding proteins that comprise the carotenoid and apocarotenoid biosynthetic pathway are of practical utility and are considered within the scope of the present invention. The *C. canephora* NCED3 promoter is exemplified herein. The upstream region of the *C. canephora* NCED3 genomic sequence is set forth herein as SEQ ID NO:25, and contains part or all of an exemplary promoter of the invention, though other portions of the promoter may be found at other locations in the gene, as explained in the definition of "promoter" set forth hereinabove. However, promoters and other gene regulatory sequences of genes encoding proteins that comprise the carotenoid and apocarotenoid biosynthetic pathway from any coffee species may be obtained by the methods described below, and may be utilized in accordance with the present invention. Promoters and regulatory elements governing tissue specificity and temporal specificity of the expression of genes encoding proteins that comprise the carotenoid and apocarotenoid biosynthetic pathway may be used to advantage, alter or modify the expression of proteins that comprise the carotenoid and apocarotenoid biosynthetic pathway toward the goal of enhancing the flavor and aroma of coffee products produced from coffee beans comprising such modifications, among other utilities.

The following sections set forth the general procedures involved in practicing the present invention. To the extent that specific materials are mentioned, it is merely for the purpose of illustration, and is not intended to limit the invention. Unless otherwise specified, general biochemical and molecular biological procedures, such as those set forth in Sambrook et al., Molecular Cloning, Cold Spring Harbor Laboratory (1989) or Ausubel et al. (eds), Current Protocols in Molecular Biology, John Wiley & Sons (2005) are used.

Nucleic Acid Molecules, Proteins and Antibodies:

Nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA having SEQ ID NOs:1-12, or the regulatory sequence of SEQ ID NO:25, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

In accordance with the present invention, nucleic acids having the appropriate level sequence homology with part or all of the coding and/or regulatory regions genes encoding proteins that comprise the carotenoid and apocarotenoid biosynthetic pathway may be identified by using hybridization and washing conditions of appropriate stringency. It will be appreciated by those skilled in the art that the aforementioned strategy, when applied to genomic sequences, will, in addition to enabling isolation coding sequences for genes encoding proteins that comprise the carotenoid and apocarotenoid biosynthetic pathway, also enable isolation of promoters and other gene regulatory sequences associated with genes encoding proteins that comprise the carotenoid and apocarotenoid biosynthetic pathway, even though the regulatory sequences themselves may not share sufficient homology to enable suitable hybridization. Moreover, the annotation of at least a partial coding sequence will enable the skilled artisan to determine the remaining coding sequence, as well the promoter or other gene regulatory sequences associated with the carotenoid or apocarotenoid protein of interest by the technique of upstream or downstream genome walking. Such techniques are established in the art. (Mishra R N et al., 2002; Rishi A S et al., 2004).

As a typical illustration, hybridizations may be performed according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45-55° C. in 2×SSC and 0.1% SDS, changing the solution every 30 minutes.

One common formula for calculating the stringency conditions required to achieve hybridization between nucleic acid molecules of a specified sequence homology (Sambrook et al., 1989):

$$Tm = 81.5° C. + 16.6 \text{ Log } [Na+] + 0.41(\% G+C) - 0.63 (\% \text{ formamide}) - 600/\#bp \text{ in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. In one embodiment, the hybridization is at 37° C. and the final wash is at 42° C.; in another embodiment the hybridization is at 42° C. and the final wash is at 50° C.; and in yet another embodiment the hybridization is at 42° C. and final wash is at 65° C., with the above hybridization and wash solutions. Conditions of high stringency include hybridization at 42° C. in the above hybridization solution and a final wash at 65° C. in 0.1×SSC and 0.1% SDS for 10 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.),pBluescript (Stratagene, La Jolla, Calif.), pCR4-TOPO (Invitrogen, Carlsbad, Calif.) or pET28a+(Novagen, Madison, Wis.), all of which can be propagated in a suitable *E. coli* host cell.

Nucleic acid molecules of the invention include cDNA, genomic DNA, RNA, and fragments thereof which may be single-, double-, or even triple-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting genes encoding proteins that comprise the carotenoid and apocarotenoid biosynthetic pathway or mRNA in test samples of plant tissue, e.g., by PCR amplification, or for the positive or negative regulation of expression genes encoding proteins that comprise the carotenoid and apocarotenoid biosynthetic pathway at or before translation of the mRNA into proteins. Methods in which oligonucleotides or polynucleotides may be utilized as probes for such assays include, but are not limited to: (1) in situ hybridization; (2) Southern hybridization (3) northern hybridization; and (4) assorted amplification reactions such as polymerase chain reactions (PCR) (including RT-PCR) and ligase chain reaction (LCR).

Polypeptides encoded by nucleic acids of the invention may be prepared in a variety of ways, according to known methods. If produced in situ the polypeptides may be purified from appropriate sources, e.g., seeds, pericarps, or other plant parts.

Alternatively, the availability of isolated nucleic acid molecules enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis., BRL, Rockville, Md. or Invitrogen, Carlsbad, Calif.

According to a preferred embodiment, larger quantities of polypeptides that comprise the carotenoid and apocarotenoid biosynthetic pathway may be produced by expression in a suitable prokaryotic or eukaryotic system. For example, part or all of a DNA molecule, such as the cDNAs having SEQ ID NOs: 1-12, may be inserted into a plasmid vector adapted for expression in a bacterial cell (such as E. coli) or a yeast cell (such as Saccharomyces cerevisiae), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The polypeptides that comprise the carotenoid and apocarotenoid biosynthetic pathway produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The polypeptides that comprise the carotenoid and apocarotenoid biosynthetic pathway of the invention, prepared by the aforementioned methods, may be analyzed according to standard procedures.

Polypeptides that comprise the carotenoid and apocarotenoid biosynthetic pathway purified from coffee, or produced recombinantly, may be used to generate polyclonal or monoclonal antibodies, antibody fragments or derivatives as defined herein, according to known methods. Antibodies that recognize and bind fragments of the polypeptides that comprise the carotenoid and apocarotenoid biosynthetic pathway of the invention are also contemplated, provided that the antibodies are specific for polypeptides that comprise the carotenoid and apocarotenoid biosynthetic pathway. For example, if analyses of the proteins or Southern and cloning analyses (see below) indicate that the cloned genes belongs to a multigene family, then member-specific antibodies made to synthetic peptides corresponding to nonconserved regions of the protein can be generated.

Kits comprising an antibody of the invention for any of the purposes described herein are also included within the scope of the invention. In general, such a kit includes a control antigen for which the antibody is immunospecific.

Carotenoids and apocarotenoids play a role in many aspects of human health and wellness. Carotenoids have been demonstrated to be powerful antioxidants (DiMascio, P et al. 1991), are efficient in protection from ultraviolet light (Sies, H et al. 2004), have immunoprotective roles and may facilitate immune cell proliferation (Watzl, B. et al. 1999; Boelsma, E et al. 2001; Aust, O et al. 2005), may be used to treat photosensitivity diseases (Matthews-Roth, M. et al. 1993), are protective against age-related macular degeneration (Seddon J M, et al. 1994), are protective against cataracts (Taylor A 1993), may guard against cardiovascular disease (Gaziano J M et al. 1993), and demonstrate a preventative and possible chemotherapeutic effect against many human cancers such as lung, orolaryngeal, colorectal, breast, prostate, and cervical cancers, among others (Mayne, S1996). In addition, carotenoids such as alpha- and beta-carotene play a key role in vitamin A synthesis. (Britton G, 1995). This list of health benefits attributable to carotenoids and apocarotenoids is meant to be illustrative and not exhaustive, and it is presumed that there are many other beneficial health effects attributable to carotenoids presently unknown. Accordingly, the coffee polypeptides that comprise the biosynthetic pathway of carotenoids and apocarotenoids described and exemplified herein are expected to find utility in a variety of food, health, and wellness applications. For example, the coffee polypeptides that comprise the biosynthetic pathway of carotenoids and apocarotenoids, or their respective carotenoid or apocarotenoid products, may be utilized as dietary supplements. In addition, the antioxidant and photoprotective properties of carotenoids and apopcarotenoids may prove advantageous in both food and cosmetic products.

One or more of the aforementioned applications for the polypeptides that comprise the carotenoid and apocarotenoid biosynthetic pathway may be pursued by exploiting the availability of the polynucleotides encoding polypeptides that comprise the carotenoid and apocarotenoid biosynthetic pathaway described herein to generate significant quantities of pure protein using recombinant organisms (e.g., in the yeast Picia pastoris or in food compatible Lactobacilli, or in plant cells), and then testing the proteins in new or established assays for antioxidant potential, immunoproliferative potential, chemoprotective or chemotherapeutic potential, and the like. Similar testing may be carried out using the carotenoids or apocarotenoids produced by these proteins according to suitable means established or developed in the art. If specific purified proteins, or carotenoid or apocarotenoid products produced by such proteins are found to be particularly useful, natural versions of those proteins and their carotenoid or apocarotenoid products also may be isolated from coffee grains or other plant parts, or from tissues and organs of other plants enriched in those carotenoid and apocarotenoid biosynthetic pathway enzymes.

Vectors, Cells, Tissues and Plants:

Also featured in accordance with the present invention are vectors and kits for producing transgenic host cells that contain a polynucleotide encoding polypeptides that comprise the carotenoid and apocarotenoid biosynthetic pathway, or an oligonucleotide, or homolog, analog or variant thereof in a sense or antisense orientation, or a reporter gene and other constructs under control of cell or tissue-specific promoters, particularly carotenoid- or apocarotenoid-encoding gene promoters as described herein, and other regulatory sequences. Suitable host cells include, but are not limited to, plant cells, bacterial cells, yeast and other fungal cells, insect cells and mammalian cells. Vectors for transforming a wide variety of these host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. Typically, kits for producing transgenic host cells will contain one or more appropriate vectors and instructions for producing the transgenic cells using the vector. Kits may further include one or more additional components, such as culture media for culturing the cells, reagents for performing transformation of the cells and reagents for testing the transgenic cells for gene expression, to name a few.

The present invention includes transgenic plants comprising one or more copies of a gene encoding a polypeptide that comprises the carotenoid and apocarotenoid biosynthetic pathway, or nucleic acid sequences that inhibit the production or function of a plant's endogenous polypeptides that comprise the carotenoid and apocarotenoid biosynthetic pathway. This is accomplished by transforming plant cells with a transgene that comprises part of all of a coding sequence for a polypeptide that comprises the carotenoid and apocarotenoid biosynthetic pathway, or mutant, antisense or variant thereof, including RNA, controlled by either native or recombinant regulatory sequences, as described below. Transgenic plants coffee species are preferred, including, without limitation, *C. abeokutae, C. arabica, C. arnoldiana, C. aruwemiensis, C. bengalensis, C. canephora, C. congensis C. dewevrei, C. excelsa, C. eugenioides,* and *C. heterocalyx, C. kapakata, C. khasiana, C. liberica, C. moloundou, C. rasemosa, C. salvatrix, C. sessiflora, C. stenophylla, C. travencorensis, C. wightiana* and *C. zanguebariae*. Plants of any species are also included in the invention; these include, but are not limited to, tobacco, *Arabidopsis* and other "laboratory-friendly" species, cereal crops such as maize, wheat, rice, soybean barley, rye, oats, sorghum, alfalfa, clover and the like, oil-producing plants such as canola, safflower, sunflower, peanut, cacao and the like, vegetable crops such as tomato tomatillo, potato, pepper, eggplant, sugar beet, carrot, cucumber, lettuce, pea and the like, horticultural plants such as aster, begonia, chrysanthemum, delphinium, petunia, zinnia, lawn and turf-grasses and the like.

Transgenic plants can be generated using standard plant transformation methods known to those skilled in the art. These include, but are not limited to, *Agrobacterium* vectors, polyethylene glycol treatment of protoplasts, biolistic DNA delivery, UV laser microbeam, gemini virus vectors or other plant viral vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., Methods for Plant Molecular Biology (Weissbach & Weissbach, eds., 1988); Methods in Plant Molecular Biology (Schuler & Zielinski, eds., 1989); Plant Molecular Biology Manual (Gelvin, Schilperoort, Verma, eds., 1993); and Methods in Plant Molecular Biology—A Laboratory Manual (Maliga, Klessig, Cashmore, Gruissem & Varner, eds., 1994).

The method of transformation depends upon the plant to be transformed. *Agrobacterium* vectors are often used to transform dicot species. *Agrobacterium* binary vectors include, but are not limited to, BIN19 and derivatives thereof, the pBI vector series, and binary vectors pGA482, pGA492, pLH7000 (GenBank Accession AY234330) and any suitable one of the pCAMBIA vectors (derived from the pPZP vectors constructed by Hajdukiewicz, Svab & Maliga, (1994) Plant Mol Biol 25: 989-994, available from CAMBIA, GPO Box 3200, Canberra ACT 2601, Australia or via the worldwide web at CAMBIA.org). For transformation of monocot species, biolistic bombardment with particles coated with transforming DNA and silicon fibers coated with transforming DNA are often useful for nuclear transformation. Alternatively, *Agrobacterium* "superbinary" vectors have been used successfully for the transformation of rice, maize and various other monocot species.

DNA constructs for transforming a selected plant comprise a coding sequence of interest operably linked to appropriate 5' (e.g., promoters and translational regulatory sequences) and 3' regulatory sequences (e.g., terminators). In a preferred embodiment, a coding sequence encoding a polypeptide that comprises the carotenoid and apocarotenoid biosynthetic pathway under control of its natural 5' and 3' regulatory elements is utilized. In other embodiments, coding and regulatory sequences are swapped (e.g., CcPSY1 coding sequence operably linked to LβCY promoter) to alter the protein content of the seed of the transformed plant for a phenotypic improvement, e.g., in flavor, aroma or other feature.

In an alternative embodiment, the coding region of the gene is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase and octopine synthase promoters. In other embodiments, a strong monocot promoter is used, for example, the maize ubiquitin promoter, the rice actin promoter or the rice tubulin promoter (Jeon et al., Plant Physiology. 123: 1005-14, 2000).

Transgenic plants with coding sequences to express polypeptides that comprise the carotenoid and apocarotenoid biosynthetic pathway under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g. hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name only a few.

Tissue specific and development-specific promoters are also contemplated for use in the present invention, in addition to the carotenoid or apocarotenoid protein promoters of the invention. Non-limiting examples of seed-specific promoters include Cim1 (cytokinin-induced message), cZ19B1 (maize 19 kDa zein), milps (myo-inositol-1-phosphate synthase), and celA (cellulose synthase) (U.S. application Ser. No. 09/377,648), bean beta-phaseolin, napin, beta-conglycinin, soybean lectin, cruciferin, maize 15 kDa zein, 22 kDa zein, 27 kDa zein, g-zein, waxy, shrunken 1, shrunken 2, and globulin 1, soybean 11S legumin (Bäumlein et al., 1992), and *C. canephora* 11S seed storage protein (Marraccini et al., 1999, Plant Physiol. Biochem. 37: 273-282). See also WO 00/12733, where seed-preferred promoters from end1 and end2 genes are disclosed. Other *Coffea* seed specific promoters may also be utilized, including but not limited to the oleosin gene promoter described in commonly-owned, co-pending Provisional Application No. 60/696,445 and the dehyrdin gene promoter described in commonly-owned, co-pending Provisional Application No. 60/696,890. Examples of other tissue-specific promoters include, but are not limited to: the ribulose bisphosphate carboxylase (RuBisCo) small subunit gene promoters (e.g., the coffee small subunit promoter as described by Marracini et al., 2003) or chlorophyll a/b binding protein (CAB) gene promoters for expression in photosynthetic tissue; and the root-specific glutamine synthetase gene promoters where expression in roots is desired.

The coding region is also operably linked to an appropriate 3' regulatory sequence. In embodiments where the native 3' regulatory sequence is not use, the nopaline synthetase polyadenylation region may be used. Other useful 3' regulatory regions include, but are not limited to the octopine synthase polyadenylation region.

The selected coding region, under control of appropriate regulatory elements, is operably linked to a nuclear drug resistance marker, such as kanamycin resistance. Other useful selectable marker systems include genes that confer antibiotic or herbicide resistances (e.g., resistance to hygromycin, sulfonylurea, phosphinothricin, or glyphosate) or genes conferring selective growth (e.g., phosphomannose isomerase, enabling growth of plant cells on mannose). Selectable marker genes include, without limitation, genes encoding antibiotic resistance, such as those encoding neomycin phosphotransferase II (NEO), dihydrofolate reductase (DHPR) and hygromycin phosphotransferase (HPT), as well as genes that confer resistance to herbicidal compounds, such as glyphosate-resistant EPSPS and/or glyphosate oxidoreducatase (GOX), Bromoxynil nitrilase (BXN) for resistance to bromoxynil, AHAS genes for resistance to imidazolinones, sulfonylurea resistance genes, and 2,4-dichlorophenoxyacetate (2,4-D) resistance genes.

In certain embodiments, promoters and other expression regulatory sequences encompassed by the present invention are operably linked to reporter genes. Reporter genes contemplated for use in the invention include, but are not limited to, genes encoding green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), β-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (FPH), thymidine kinase (TK), lacZ (encoding α-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). As with many of the standard procedures associated with the practice of the invention, skilled artisans will be aware of additional sequences that can serve the function of a marker or reporter.

Additional sequence modifications are known in the art to enhance gene expression in a cellular host. These modifications include elimination of sequences encoding superfluous polyadenylation signals, exon-intron splice site signals, transposon-like repeats, and other such well-characterized sequences that may be deleterious to gene expression. Alternatively, if necessary, the G/C content of the coding sequence may be adjusted to levels average for a given coffee plant cell host, as calculated by reference to known genes expressed in a coffee plant cell. Also, when possible, the coding sequence is modified to avoid predicted hairpin secondary mRNA structures. Another alternative to enhance gene expression is to use 5' leader sequences. Translation leader sequences are well known in the art, and include the cis-acting derivative (omega') of the 5' leader sequence (omega) of the tobacco mosaic virus, the 5' leader sequences from brome mosaic virus, alfalfa mosaic virus, and turnip yellow mosaic virus.

Plants are transformed and thereafter screened for one or more properties, including the presence of the transgene product, the transgene-encoding mRNA, or an altered phenotype associated with expression of the transgene. It should be recognized that the amount of expression, as well as the tissue- and temporal-specific pattern of expression of the transgenes in transformed plants can vary depending on the position of their insertion into the nuclear genome. Such positional effects are well known in the art. For this reason, several nuclear transformants should be regenerated and tested for expression of the transgene.

Methods:

The nucleic acids and polypeptides of the present invention can be used in any one of a number of methods whereby the protein products can be expressed in coffee plants in order that the proteins may play a role in photosynthesis, and in the enhancement of flavor and/or aroma of the coffee beverage or coffee products ultimately produced from the bean of the coffee plant expressing the protein. Similarly, the polypeptides of the invention can be used in any one of a number of methods whereby the carotenoids, apocarotenoids, and other such phytochemical products synthesized from the polypeptides may play a role in photosynthesis, and in the enhancement of flavor and/or aroma of the coffee beverage or coffee products ultimately produced from the bean of the coffee plant containing the carotenoids and apocarotenoids.

With respect to photosynthesis, carotenoids play a role in photoprotection under light stress, and in light collection in shady environments. In fact, many plants alter their carotenoid composition in response to shady conditions versus full sunlight. (Demmig-Adams et al., 1996). Therefore, the ability to manipulate production of polypeptides that comprise the biosynthetic pathway for carotenoids and apocarotenoids in a plant, or even to use the polynucleotides and proteins of the invention to monitor such gene expression, will enable study and manipulation of the response of the coffee plant to varying levels of sunlight. This knowledge enables the generation of modified coffee plants that are better equipped for photosynthesis in sub-optimal conditions such as excess light, where carotenoids protect photosynthetic pigments, or insufficient light, where a decrease in accessory pigments enables more efficient light harvesting.

With respect to flavor and aroma of roasted coffee grain, it is expected that the polypeptides that comprise the carotenoid and apocarotenoid biosynthetic pathway exert some influence on the generation of coffee flavors via the Maillard reaction that occurs during roasting, by means of the content of the proteins themselves, or the products such as carotenoids or apocarotenoids they produce. Proteins, and particularly protein degradation products (peptides and amino acids), represent an important group of flavor precursors (Spanier et al., 2004). Therefore, relatively abundant proteins such as those that comprise the carotenoid and apocarotenoid biosynthetic pathway can be expected to make some contribution to the flavor generating reactions that occur during coffee roasting. Such a contribution may stem from the concentration of the proteins themselves in the coffee bean, or the concentration of the carotenoids or apocarotenoids ultimately produced from the proteins. The ability to monitor (e.g., through marker-assisted breeding) or manipulate protein expression profiles for polypeptides that comprise the carotenoid or apocarotenoid biosynthetic pathway is provided by the polynucleotides of the present invention, in accordance with the methods described herein.

Thus, one aspect of the present invention features methods to alter the profile of polypeptides that comprise the carotenoid or apocarotenoid biosynthetic pathway in a plant, preferably coffee, comprising increasing or decreasing an amount or activity of one or more polypeptides that comprise the carotenoid or apocarotenoid biosynthetic pathway in the plant. For instance, in one embodiment of the invention, a gene encoding a polypeptide that comprises the carotenoid or apocarotenoid biosynthetic pathway under control of its own expression-controlling sequences is used to transform a plant for the purpose of increasing production of that polypeptide in the plant. Alternatively, a coding region for a polypeptide that comprises the carotenoid or apocarotenoid biosynthetic pathway is operably linked to heterologous expression controlling regions, such as constitutive or inducible promoters.

Increasing carotenoid and apocarotenoid production in coffee seeds is expected to have a variety of beneficial effects. Coffee has been shown to contain two carotenoid derived flavor components, α-ionone and β-damascenone (Czerny et al., 2000; Akiyama et al., 2003; Variyar et al., 2003), the latter being identified as major components of coffee both before and after roasting (Ortiz et al., 2004). Czemy et al. (2000) identified a 800-fold increase in β-damascenone after roasting. Due to their low odor threshold, only small amounts of these and other carotenoid derived volatile compounds are needed to alter the aroma of roasted coffee.

Increasing carotenoid content in coffee grain is therefore expected to lead to an increase in carotenoid derived volatiles implicated in aroma during the roasting process. The 800-fold increase in β-damascenone during roasting is likely due to the thermal breakdown of the carotenoid precursor. Increased production of carotenoids may lead to an increase in β-damascenone as well as the formation of new apocarotenoids not previously detected in coffee, such as β-ionone, pseudoionone, geranylacetone, β-cyclocitral, citral and 6-methyl-5-hepten-2-one. In other systems, e.g., tomato, the aroma of the "high beta" mutant, which accumulates α-carotene, is dominated by the β-carotene derived β-ionone, whereas the Jubilee mutant, which produces mainly acyclic carotenes has been shown to produce geranylacetone (Stevens, 1970). Acyclic carotenes such as 1-carotene have been shown to be the precursors of geranylacetone (Simkin et al., 2004b). Thus, modifications in carotenoid content or of specific carotenoids can lead to changes in related carotenoid derived volatiles.

The polynucleotides and methods provided in accordance with the present invention also enable the overproduction of novel ketocarotenoids, such as astaxanthin (3,3'dihydroxy-4, 4'diketo-β,β-carotene) formed from β-carotene and zeaxanthin, by the overexpression of *Adonis aestivalis* ketocarotenoid biosynthetic genes (Cunningham and Gantt, 2005). Astaxanthin is involved in cancer prevention (Tanaka et al, 1994) and has been described as an immune system enhancer (Jyonouchi et al., 1993) Astaxanthin is used as a food supplement and in animal and fish feed. Its presence in coffee could impart a health benefit and could result in the formation of novel apocarotenoids during roasting.

The over-expression of phytoene synthase (PSY) in transgenic tomatoes redirected metabolites from the diterpenoid pathway for the formation of carotenoids (Fray et al, 1995). All diterpenoids are derived from geranylgeranyl diphosphate, the precursor of the first carotenoid-phytoene (Richman et al., 1998). Two diterpenoids of interest are cafestol and kahweol, which have been associated with negative health impacts of espresso coffee. Accordingly, seed-specific overexpression of PSY in coffee seeds may lead to a decrease in the undesirable diterpenoids (cafestol and kahweol) by diverting metabolites for the formation of health beneficial carotenoids.

The capacity for light collection in shady environments in a plant such as the coffee plant may be improved by decreasing production of one or more of the polypeptides that comprise the carotenoid or apocarotenoid biosynthetic pathway in the plant, by screening naturally-occurring variants for decreased expression of polypeptides that comprise the carotenoid or apocarotenoid biosynthetic pathway, or by screening naturally-occurring variants for decreased levels of the various carotenoids or apopcarotenoids. For instance, loss-of-function (null) mutant plants may be created or selected from populations of plant mutants currently available. It will also be appreciated by those of skill in the art that mutant plant populations may also be screened for mutants that over-express a particular polypeptide that comprises the carotenoid or apocarotenoid biosynthetic pathway, utilizing one or more of the methods described herein. Mutant populations can be made by chemical mutagenesis, radiation mutagenesis, and transposon or T-DNA insertions, or targeting induced local lesions in genomes (TILLING, see, e.g., Henikoff et al., 2004, Plant Physiol. 135(2): 630-636; Gilchrist & Haughn, 2005, Curr. Opin. Plant Biol. 8(2): 211-215). The methods to make mutant populations are well known in the art.

The nucleic acids of the invention can be used to identify mutant polypeptides that comprise the carotenoid and apocarotenoid biosynthetic pathway in various plant species. In species such as maize or *Arabidopsis*, where transposon insertion lines are available, oligonucleotide primers can be designed to screen lines for insertions in the genes encoding polypeptides that comprise the carotenoid and apocarotenoid biosynthetic pathway. Through breeding, a plant line may then be developed that is heterozygous or homozygous for the interrupted gene.

A plant also may be engineered to display a phenotype similar to that seen in null mutants created by mutagenic techniques. A transgenic null mutant can be created by a expressing a mutant form of a selected polypeptide that comprises the carotenoid and apocarotenoid biosynthetic pathway to create a "dominant negative effect." While not limiting the invention to any one mechanism, this mutant protein will compete with wild-type protein for interacting proteins or other cellular factors. Examples of this type of "dominant negative" effect are well known for both insect and vertebrate systems (Radke et al., 1997, Genetics 145: 163-171; Kolch et al., 1991, Nature 349: 426-428).

Another kind of transgenic null mutant can be created by inhibiting the translation of mRNA encoding the polypeptides that comprise the carotenoid and apocarotenoid biosynthetic pathway by "post-transcriptional gene silencing." The gene from the species targeted for down-regulation, or a fragment thereof, may be utilized to control the production of the encoded protein. Full-length antisense molecules can be used for this purpose. Alternatively, antisense oligonucleotides targeted to specific regions of the mRNA that are critical for translation may be utilized. The use of antisense molecules to decrease expression levels of a pre-determined gene is known in the art. Antisense molecules may be provided in situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al., 1998, PNAS 95: 13959-13964). In this regard, dsRNA containing sequences that correspond to part or all of at least one intron have been found particularly effective. In one embodiment, part or all of the coding sequence antisense strand is expressed by a transgene. In another embodiment, hybridizing sense and antisense strands of part or all of the coding sequence for polypeptides that comprise the carotenoid and apocarotenoid biosynthetic pathway are transgenically expressed.

In another embodiment, carotenoid and apocarotenoid genes may be silenced through the use of a variety of other post-transcriptional gene silencing (RNA silencing) techniques that are currently available for plant systems. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner (for reviews of RNA silencing in plants, see Horiguchi, 2004, Differentiation 72: 65-73; Baulcombe, 2004, Nature 431: 356-363; Herr, 2004, Biochem. Soc. Trans. 32: 946-951).

Small interfering RNAs may be chemically synthesized or transcribed and amplified in vitro, and then delivered to the cells. Delivery may be through microinjection (Tuschl T et al., 2002), chemical transfection (Agrawal N et al., 2003), electroporation or cationic liposome-mediated transfection (Brummelkamp T R et al., 2002; Elbashir S M et al., 2002), or any other means available in the art, which will be appreciated by the skilled artisan. Alternatively, the siRNA may be expressed intracellularly by inserting DNA templates for siRNA into the cells of interest, for example, by means of a plasmid, (Tuschl T et al., 2002), and may be specifically targeted to select cells. Small interfering RNAs have been successfully introduced into plants. (Klahre U et al., 2002).

A preferred method of RNA silencing in the present invention is the use of short hairpin RNAs (shRNA). A vector containing a DNA sequence encoding for a particular desired siRNA sequence is delivered into a target cell by any common means. Once in the cell, the DNA sequence is continuously transcribed into RNA molecules that loop back on themselves and form hairpin structures through intramolecular base pairing. These hairpin structures, once processed by the cell, are equivalent to siRNA molecules and are used by the cell to mediate RNA silencing of the desired protein. Various constructs of particular utility for RNA silencing in plants are described by Horiguchi, 2004, supra. Typically, such a construct comprises a promoter, a sequence of the target gene to be silenced in the "sense" orientation, a spacer, the antisense of the target gene sequence, and a terminator.

Yet another type of synthetic null mutant can also be created by the technique of "co-suppression" (Vaucheret et al., 1998, Plant J. 16(6): 651-659). Plant cells are transformed with a copy of the endogenous gene targeted for repression. In many cases, this results in the complete repression of the native gene as well as the transgene. In one embodiment, a gene encoding a polypeptide that comprises the carotenoid and apocarotenoid biosynthetic pathway from the plant species of interest is isolated and used to transform cells of that same species.

Mutant or transgenic plants produced by any of the foregoing methods are also featured in accordance with the present invention. Preferably, the plants are fertile, thereby being useful for breeding purposes. Thus, mutant or plants that exhibit one or more of the aforementioned desirable phenotypes can be used for plant breeding, or directly in agricultural or horticultural applications. They will also be of utility as research tools for the further elucidation of the participation of polypeptides that comprise the carotenoid and apocarotenoid biosynthetic pathway in flavor, aroma and other features of coffee seeds associated with pigments and photosynthesis. Plants containing one transgene or a specified mutation may also be crossed with plants containing a complementary transgene or genotype in order to produce plants with enhanced or combined phenotypes.

The present invention also features compositions and methods for producing, in a seed-preferred or seed-specific manner, any selected heterologous gene product in a plant. A coding sequence of interest is placed under control of a seed-specific coffee promoter such as a carotenoid or apocarotenoid protein-encoding gene promoter, and other appropriate regulatory sequences, to produce a seed-specific chimeric gene. The chimeric gene is introduced into a plant cell by any of the transformation methods described herein or known in the art. These chimeric genes and methods may be used to produce a variety of gene products of interest in the plant, including but not limited to: (1) detectable gene products such as GFP or GUS, as enumerated above; (2) gene products conferring an agronomic or horticultural benefit, such as those whose enzyme activities result in production of micronutrients (e.g., pro-vitamin A, also known as beta-carotene) or antioxidants (e.g., ascorbic acid, omega fatty acids, lycopene, isoprenes, terpenes); or (3) gene products for controlling pathogens or pests, such as described by Mourgues et al., (1998), TibTech 16: 203-210 or others known to be protective to plant seeds or detrimental to pathogens.

The following examples are provided to illustrate the invention in greater detail. The examples are intended illustrate, not to limit, the invention.

EXAMPLE 1

Materials and Methods for Subsequent Examples

Plant material. Freshly harvested roots, young leaves, stems, flowers and fruit at different stages of development were harvested from *Coffea arabica* L. cv. *Caturra* T-2308 and *Coffea canephora* var. *BP*409 grown under greenhouse conditions (25° C., 70 RH) and also from *Coffea canephora* BP-409 grown in the field in East Java, Indonesia. The development stages are defined as follows: small green fruit (SG), large green fruit (LG), yellow fruit (Y) and red fruit (R). Fresh tissues were frozen immediately in liquid nitrogen, then stored at −80° C. until used for RNA extraction.

Cloning of full-length cDNA Sequences. The 5' upstream region of phytoene synthase (PSI) from *Coffea canephora* was recovered using the Genewalker kit (3D Biosciences) and the primers GWPSY1 (5'-ACTTCACCGCAGCGATCAT-AAGCTTCAC-3') (SEQ ID NO.:26) followed by nested PCR using primer GWPSY2 (5'-TTCACGTCCCAATCTTCTC-GAGATCTC-3') (SEQ ID NO.:27). PCR reactions contained 1× buffer and 5 mM MgCl$_2$, 200 µM each of dATP, dCTP, dGTP and dTTP, and 1 units of LA Taq polymerase (Takara, Combrex Bio, Belgium) and 200 nM primer GWPSY1 and 200 nM primer AP1 (5'-GTAATACGACTCACTATAGGGC-3'; Genewalker kit) (SEQ ID NO.:28). The reaction mixture was incubated for 10 min at 94° C., followed by 7 amplification cycles of 25 sec at 94° C./4 min at 72° C. and then 32 amplification cycles of 25 sec at 94° C./4 min at 67° C. The PCR reaction was diluted 1/200 with sterile distilled water and the used for a second PCR reaction using 200 nM of nested primer GWPSY2 and 200 nM of nested primer AP2 (5'-ACTATAGGGCACGCGTGGT-3'; Genewalker kit) (SEQ ID NO.:29). Nested PCR was incubated for 10 min at 94° C., followed by 5 amplification cycles of 25 sec at 94° C./4 min at 72° C. and then 22 amplification cycles of 25 sec at 94° C./4 min at 67° C. A band of approximately 1.8 kb was recovered following PCR and cloned into pCR4-TOPO to make pCR4-GWPSY1, and the insert of this plasmid was sequenced resulting in the recovery of the full-length ORF PSY after the in silico assembly of the sequences.

Using the Genewalker kit, the 5' region of Violaxanthin de-epoxidase was recovered from *Coffea canephora* using primers GWVDE1 (5'-ACATTTCTTTCGTGAGACTGCA-CACTC-3') (SEQ ID NO.:30), followed by nested PCR using primer GWVDE2 (5'-ATCACCACATTTGATCTGGCAT-TCAGTC-3') (SEQ ID NO.: 31). A band of approximately 2.3 kb was recovered and cloned into pCR4-TOPO to generate pCR4-GWVDE, and the insert of this clone was sequenced resulting in the generation of the full-length ORF for VDE. The ORF contained two introns of 128 bp and 841 bp at positions 282 and 447, respectively, of the ORF. After the in-silico assembly of the sequences, the 1248 bp ORF was re-cloned by RT-PCR using the primers VDEFWR (5'-CACC ATGGCTTCTGCTTTGCATTCAGC-3') (SEQ ID NO.:32) and VDEREV (5'-ACTACCTTAGCTTCCTAATTGG-3') (SEQ ID NO.:33), and cloned into pENTR/D (Invitrogen) to make pENTR-CcVDE. This clone was then verified by sequencing.

Using the Genewalker kit, the missing 5' region of CCD1 was recovered using nested primers GWCCD11 (5'-AA-CAATCCGAACAGCCCCTTGAGATCCC-3') (SEQ ID NO.:34) and GWCCD12 (5'-GTTTAAGCCTTGATGTCT-TCACGTACCG-3') (SEQ ID NO.:35). A fragment 2475 bp was recovered and cloned into pCR4-TOPO to generate pCR4-GWCCD1 #1, and the insert of this clone was sequenced, resulting in the generation of an extended-length coding sequence for CCD1 containing three introns of 1604 bp, 267 bp and 605 bp at positions 237, 309 and 324, respectively, of the ORF. Because this step did not produce a full length coding sequence, a second round of genome walking was carried out using the nested primers GWCCD13 (5'-TGCCAAGTTACTGTTCAATGACTAGGC-3') (SEQ ID NO.:36) and GWCCD14 (5'-AAGCAATTTAATCCCGTC-CTTAATCTGG-3') (SEQ ID NO.:37). This genome walking step resulted in a fragment 1045 bp, which was cloned into pCR4-TOPO to generate pCR4-GWCCD1 #2, and the insert of this clone was sequenced. The full-length coding sequence was generated from the two over-lapping genewalker sequences and the EST sequence (cccwc22w2a6). After the in-silico assembly of the sequences, the ORF of 1647 bp was re-cloned by RT-PCR using primers CCD1FWR (5'-CACC ATGGGTAGGCAAGAAGGAGAAG-3') (SEQ ID NO.:38) and CCD1REV (5'-ACTCTCCAGGACATGGTCCAGC-3') (SEQ ID NO.:39), and cloned into pENTR/D (Invitrogen) to generate pENTR-CcCCD1. This clone was then sequenced.

Using the Genewalker kit, the full coding sequence of NCED3 was obtained using nested primers GWNCED3F (5'-AAGCAGAAGCAGTCAGGGACTTCTACC-3') (SEQ ID NO.:40) and GWNCED3R (5'-TATCCAGTACAC-CGAATCTTGACACC-3') (SEQ ID NO.:41). This generated a 2.5 kb fragment, which was cloned into pCR4-TOPO to generate pCR4-GWNCED#4. The insert of this clone was sequenced, resulting in the full-length open reading frame of 1908 bp and 1104 bp upstream of the ATG. Consistent with other reported NCEDs, CcNCED3 contains no introns.

The in-silico assembly of the ORF will be confirmed by RT-PCR using primers NCED3FWR (5'-CACCAT-GATGGGCTTGGGTTTGGGTTGC-3') (SEQ ID NO.:42) and NCED3REV (5'-TCACAAGTTTCTTTCaGTTC-CAGGC-3') (SEQ ID NO.:43). The CcNCED3 will be cloned into pENTR/D (Invitrogen) to generate pENTR-CcNCED3, and this clone will then be verified by sequencing.

The full-length β-carotene hydroxylase cDNA was recovered from grain by RT-PCR using primers βCHYFWR (5'-CACCATGGCTGCCGGAATTGCCGTC-3') (SEQ ID NO.: 44) and βCHYREV (5'-CAAGTTGCGTAAGGGTTCA TAA-3') (SEQ ID NO.:45) and cloned into pENTR/D (Invitrogen) to generate pENTR-CcβCHY. This clone was verified by sequencing.

cDNA Isolation Using Degenerate Primers:

A search of the EST database for PDS revealed no corresponding sequences. However, a partial length cDNA of 897 bp was recovered from yellow robusta grain by RT-PCR using degenerate primers DegPDS2 FWR (5'-GGTG-GAAAGRTAGCTGCATGGA-3') (SEQ ID NO.:46) and DegPDS4 REV (5'-TGTTACRGACATGTCAGCATACAC-3') (SEQ ID NO.:47), which correspond to the conserved peptide sequences GGKVAAW (SEQ ID NO.:48) and VYADMSVT (SEQ ID NO.:49) found in LePDS (CAA55078), CaPDS (CAA48195) and AtPDS (AAA20109) orthologues. To generate the cDNA, PCR was carried out as follows: 3 min 94° C., followed by 10 cycles of 1 min 94° C.; 30 sec 60-50° C. (temperature decreasing by 1° C. per cycle); 2 min 72° C., followed by an additional 25 cycles of 1 min 94° C.; 30 sec 50° C.; 2 min 72° C.

Using the Genewalker kit, the partial coding sequence of PDS was extended using nested primers GWPDS1 (5'-AT-CATTGAATGCTCCTTCCACTGCAAC-3') (SEQ ID NO.: 50) and GWPDS2 (5'-TCATTAATTCCTAGTTCTCCAAA-CAGG-3') (SEQ ID NO.:51). This generated of a fragment of 2066 bp. This fragment was cloned into pCR4-TOPO to generate pCR4-GWPDS#5. The insert of this clone was sequenced, resulting in an additional 225 bp of the coding sequence and a partial ORF of 1077 bp containing 3 introns of 616 bp, 373 bp and 609 bp at positions 122 bp, 215 bp and 272 bp of the partial ORF, respectively.

No corresponding sequences were detected in the EST database for ZDS, however, a partial cDNA clone of 472 bp was recovered using the non-degenerate primers DegZDS1 FWR (5'-TTGCAGGCATGTCGACTGCTG-3') (SEQ ID NO.:52) and DegZDS3 REV (5'-GTGGGATCCTGTTG-CATATGCTCT-3') (SEQ ID NO.:50), which encode the conserved amino acid sequences LAGMSTAV (SEQ ID NO.:54) and MWDPVAYAL (SEQ ID NO.:55) in the Zeta-carotene desaturase orthologues LeZDS (AF195507), CaZDS (X89897) and AtZDS (U38550). The coffee cDNA used to recover this partial cDNA clone was generated from robusta grain at the yellow stage. The PCR conditions are the same as used for cloning the PDS cDNA (described above). The partial cDNA fragment obtained was cloned into pCR4-TOPO to generate pCR4-CcZDS#1.

Extraction of Total RNA and Generation of cDNA:

Plant tissue samples stored at −80° C. were ground into a powder and total RNA was extracted from this powder using the method described by Lepelley et al. (this is the HQT/HCT reference). To remove DNA, samples were treated with DNase using the kit "Qiagen RNase-Free DNase" according to the manufacturer's instructions. All RNA samples were analysed by formaldehyde agarose gel electrophoresis. Ribosomal RNA bands were visualized with ethidium bromide staining.

Using oligo $(dT_{20})$ as a primer, cDNA was prepared from approximately 4 μg total RNA according to the protocol in the Superscript II Reverse Transcriptase kit (Invitrogen, Carlsbad, Calif.). To test for the presence of contaminating genomic DNA in the cDNA preparations, a primer pair was designed spanning a known intron of a specific ubiquitously expressed coffee cDNA, chalcone isomerase (CHI). RT-PCR was carried out using 10-fold dilution of cDNA corresponding to 0.1 μg of original RNA. Conventional-PCR reactions contained 1× buffer and 5 mM MgCl$_2$, 200 μM each of dATP, dCTP, dGTP and dTTP, and 1 unit of polymerase and 800 nM of each gene specific primers —FWD-CCCACCTGGAGC-CTCTATTCTGTT (SEQ ID NO.:56) and REV-CCCCGTCGGCCTCAAGTTTC (SEQ ID NO.:57) for 35 cycles. A cDNA band of 272 bp was observed following PCR. A second band which would correspond to the cDNA+intron at 750 bp was not observed, indicating an absence of genomic DNA in the samples (data not shown). These RNA samples were later used to generate full-length ORF sequences according to the methods described above. These ORF's were subsequently cloned into pENTR/D (Invitrogen).

Quantitative TaqMan-PCR was carried out with cDNA using the protocol recommended by the manufacturer (Applied Biosystems, Perkin-Elmer). All reactions contained 1× TaqMan buffer (Perkin-Elmer) and 5 mM MgCl$_2$, 200 μM each of dATP, dCTP, dGTP and dTTP, and 0.625 units of AmpliTaq Gold polymerase. PCR was carried out using 800 nM of each gene specific primers, forward and reverse, and 200 nM for the TaqMan probe and 1000-fold dilution of cDNA corresponding to 0.001 μg of original RNA. Primers and probes were designed using PRIMER EXPRESS software (Applied Biosystems: see Table 1). The cross specificity of the primers and probes is summarized in Table 4. The reaction mixture was incubated for 2 min at 50° C., then 10 min at 95° C., followed by 40 amplification cycles of 15 sec at 95° C./1 min at 60° C. Samples were quantified in the GeneAmp 7500 Sequence Detection System (Applied Biosystems). Transcript levels were normalized to the levels of the control gene rpl39.

Table 1

Primers and probes used in real-time quantitative RT-PCR. The right-hand column indicates size of the amplicon.

| Gene | Sequence | SEQ ID NO.: |
|---|---|---|
| PSY | Forward TGATGAGGCAGAGAAAGGAGTGA | 58 |
| | Reverse GATGCCCATACAGGCCATCT | 59 |
| | Probe[1] CGAGCTCAACTCTG | 60 |
| PDS | Forward TGGTAACCCTCCAGAGAGACTTTG | 61 |
| | Reverse TCTGCCTCCTCGTGACTCAA | 62 |
| | Probe[1] ATGCCGATTGTTGAGCA | 63 |
| ZDS | Forward GCTGATAAAAATTTGCTCGTGAAG | 64 |
| | Reverse CACCAATTTCACCCCCTTTG | 65 |
| | Probe[1] ATCATACTCACACATTTGTT | 66 |
| PTOX | Forward AAACGGAGAGCCACCTGATG | 67 |
| | Reverse TGCTCAATCTTTACAACCCATTTC | 68 |
| | Probe[1] TCATCCTCTAGTGGTTTGG | 69 |
| LeCY | Forward GCCGCAAGAGAGGAAACG | 70 |
| | Reverse GCAAAATAAGTGCCAATCCAAA | 71 |
| | Probe[1] CAGAGAGCATTCTTC | 72 |
| βCHY | Forward CGCCGTCCCTGCCATA | 73 |
| | Reverse AATGAGGCCCTTGTGGAAGA | 74 |
| | Probe[1] CCCTCCTTTCTTATGGC | 75 |
| ZEP | Forward TTGGTTCTGACAAGGGTGCAT | 76 |
| | Reverse CGAGAACGGTGGCTGGTT | 77 |
| | Probe[1] CCGGGTAAAGGTCA | 78 |
| VDE | Forward CCCCTTGTCGAGAGATTGGA | 79 |
| | Reverse ACCTCCCTTACGATTGTCCTTTC | 80 |
| | Probe[1] AAGACAGTGGAAGAAGG | 81 |

Table 1-continued

Primers and probes used in real-time quantitative RT-PCR. The right-hand column indicates size of the amplicon.

| Gene | Sequence | SEQ ID NO.: |
|---|---|---|
| CCD1 | Forward CCTAGGACCAGGAAGGTTTGG | 82 |
| | Reverse CCAGGCTGGCGTGGAA | 83 |
| | Probe[1] CGGAGGCTATCTTT | 84 |
| NCED3 | Forward GGAAATCGGAGCTTAGAATTGTCA | 85 |
| | Reverse CAGCTGCACTGATGCCTCTAAT | 86 |
| | Probe[1] CGCCATGACATTGG | 87 |
| FIB1 | Forward CTGTCCAGGACACAGCATCCT | 88 |
| | Reverse TCAGTGGTGGTCGGCTAGAAA | 89 |
| | Probe[1] GTCGCAAAGTCC | 90 |
| RPL39 | Forward GAACAGGCCCATCCCTTATTG | 91 |
| | Reverse CGGCGCTTGGCAATTGTA | 92 |
| | Probe[2] ATGCGCACTGACAACA | 93 |

All sequences are given 5' to 3'.
[1] MGB Probes were labelled at the 5' end with fluorescent reporter dye 6-carboxyfluorescein (FAM) and at the 3' end with quencher dye 6-carboxy-tetramethyl-rhodamine (TAMRA).
[2] RPL39 probe were labelled at the 5' end with fluorescent reporter dye VIC and at the 3' end with quencher TAMRA.

Functional Evaluation of Selected cDNAs in E. coli:

The functionality of some encoded proteins was tested by co-expression of the corresponding cDNA containing complete ORF sequences in carotenoid accumulating strains of E. coli. The full-length Coffea CCD1 was recovered from grain by RT-PCR using the primers CCD1FWR (5'-CACC ATGGGTAGGCAAGAAGGAGAAG-3') (SEQ ID NO.:38) and CCD1REV (5'-ACTCTCCAGGACATGGTCCAGC-3') (SEQ ID NO.:39), and cloned into the gateway vector pENTR/D (Invitrogen) to make pENTR-CcCCD1. The sequence of clone pENTR-CcCCD1 was identical to that of the previous in-silico sequence. The CCD1 ORF was transferred into the gateway bacterial expression vector pDEST17 (Invitrogen) by recombination as described by the manufacturer (Invitrogen) to make pDEST17-CcCCD1.

At the same time, the full-length Coffea βCHY was recovered from grain by RT-PCR using primers βCHYFWR (5'-CACCATGGCTGCCGGAATTGCCGTC-3') (SEQ ID NO.: 44) and βCHYREV (5'-CAAGTTGCGTAAGGGTTCA TAA-3') (SEQ ID NO.:45) and cloned into pENTR/D (Invitrogen) to make pENTR-CcβCHY, and then sequenced. The βCHY ORF was transferred into the gateway bacterial expression vector pDEST17 (Invitrogen) by recombination as described by the manufacturer (Invitrogen) to make pDEST17-CcβCHY.

Figure 6A:
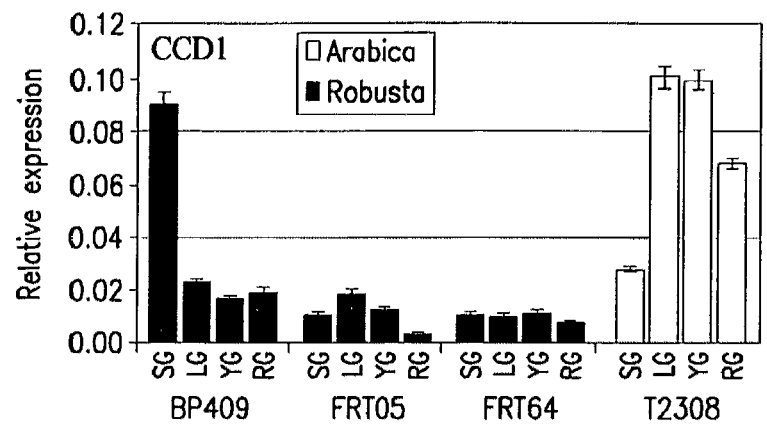
FIG. 6. Expression of CCD1 transcripts during seed development and activity of CcCCD1 in *E. Coli*.
Figure 7A:
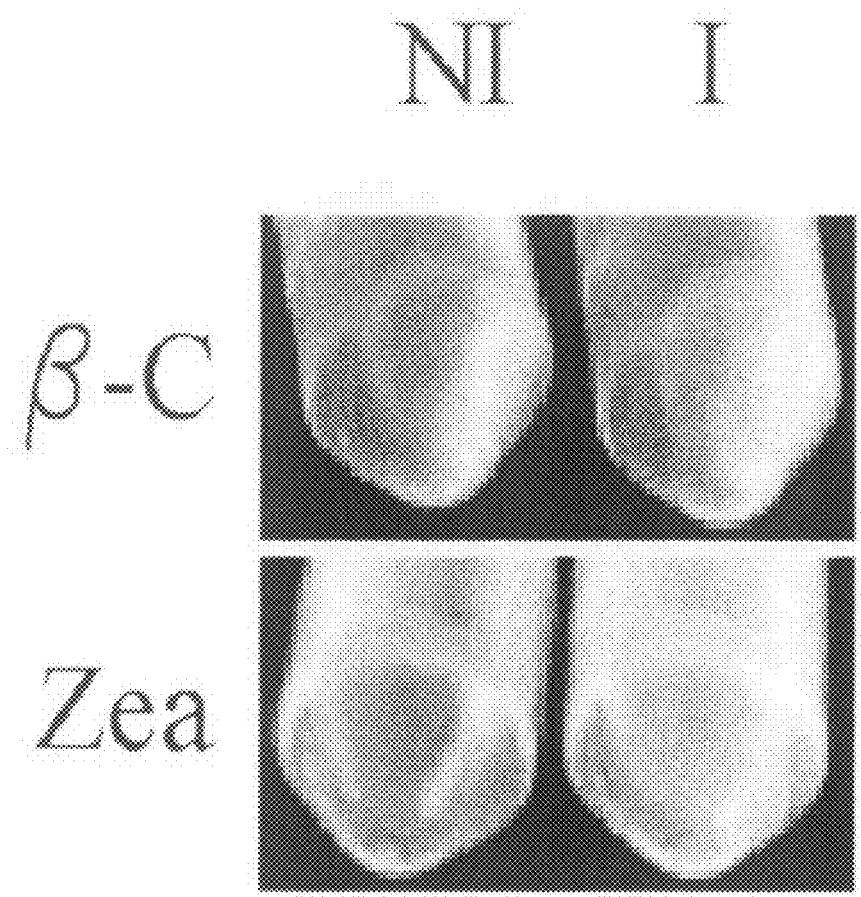

Plasmids pAC-LYC, pAC-BETA and pAC-ZEAX containing specific sets of functional carotenoid biosynthetic genes of Erwinia herbicola responsible for the formation of lycopene, β-carotene and zeaxanthine, respectively (Cunningham et al., 1994; Cunningham et al., 1996; Sun et al., 1996; Cunningham and Gantt, 2001) were co-transformed into E. coli strain BL21-AI with either the pDEST17-CcCCD1 or pDEST17-CcβCHY constructs described above. An overnight 3 ml culture of each strain, which is selected to contain both sets of plasmids by the addition of chloramphenicol (pAC plasmids) and ampicillin (pDEST17 plasmid), was used to inoculate 50 ml of LB medium containing the appropriate antibiotics and 0.2% glucose. The cultures were grown at 28° C. until a cell density corresponding to an absorbance at 600 nm of 0.5 was reached. Expression of the protein was induced by addition of 0.2% arabinose and the cultures were grown at 28° C. overnight. 2 ml of the E. coli culture was centrifuged, and the cell pellet was photographed (FIGS. 6A and 7A). The remaining E. coli culture was centrifuged, and the cell pellet was resuspended in an equal volume of formaldehyde. An equal volume of methanol was then added, followed by two volumes of ethyl acetate. The phases were separated by the addition of water, and the ethyl acetate phase was retained for HPLC analysis. The ethyl acetate was evaporated under vacuum and analysed by HPLC as described below.

Carotenoid Analysis:

The method used to analyze and quantify carotenoids is detailed in Fraser et al. (2000). Typically, grain tissues were ground into a powder and were freeze-dried and, 10-50 mg aliquots were extracted using methanol:chloroform (1:3 by vol) and partitioned against 50 mM Tris-HCl pH 7.0 (2 vols). The aqueous phase was re-extracted twice. HPLC separations were performed on a C30 reverse-phase column (250× 4.6 mm) purchased from YMC, Wilmington, N.C. The mobile phases used were methanol (A), water/methanol (20/80 by vol) containing 0.2% ammonium acetate (B) and tert-methyl butyl ether (C). The gradient used was 95% A/5% B isocratically for 12 minutes, a step to 80% A/5% B/ and 15% C at 12 minutes, followed by a linear gradient to 30% A/5% B/65% C for 30 min (Fraser et al., 2002).

EXAMPLE 2

Isolation and Identification of Carotenoid Biosynthetic Pathway Genes from *Coffea canephora*

ESTs representing the longest available cDNA for genes of the carotenoid biosynthetic pathway and those involved in the formation of the carotenoid-derived apocarotenoids were isolated from the appropriate library and sequenced. The fully sequenced cDNAs were then analyzed for homologies with known sequences, and named as follows: phytoene synthase (PSY) (cccs30w7e6), β-carotene hydroxylase (BCH) (cccs46w21b8), lycopene ε-cyclase (LεCY) (cccp8f16), zeaxanthin epoxidase (ZEP) (cccp129g15), violaxanthin de-epoxidase (VDE) (cccp13a9), and carotenoid cleavage dioxygenase 1 (CCD1) (cccwc22w2a6). Additional ESTs encoding for the Fibrillin (FIB) structural protein implicated in carotenoid stockage (cccs16w15e14), and an ortholog of the plastid terminal oxidase, a co-factor for carotenoid desaturation (PTOX; cccl24o10) and a putative lycopene ε-cyclase (LεCY) (cccp8f16) were also identified. The number and distribution of the associated ESTs are shown in Table 2.

TABLE 2

Number and distribution of ESTs in the unigene

| | | Number of ESTs | | | | | |
|---|---|---|---|---|---|---|---|
| | Unigene | Seed 18w | Seed 30w | Seed 46w | pericarp | leaf | Total |
| CcPSY | 123321 | 0 | 2 | 0 | 1 | 0 | 3 |
| CcPTOX | 121182 | 0 | 0 | 0 | 0 | 3 | 3 |
| CcβCHY | 123117 | 0 | 1 | 1 | 3 | 3 | 8 |
| CcLεCY | 131043 | 0 | 0 | 0 | 1 | 0 | 1 |
| CcZEP | 112969 | 0 | 0 | 0 | 2 | 1 | 3 |
| CcVDE | 130454 | 0 | 0 | 0 | 1 | 0 | 1 |
| CcNCED3 | 130641 | 0 | 0 | 0 | 1 | 0 | 1 |
| CcCCD1 | 121850 | 0 | 3 | 0 | 0 | 0 | 3 |
| CcFIB | 119688 | 0 | 0 | 1 | 1 | 0 | 2 |
| CcPDH | 125598 | 0 | 0 | 0 | 0 | 1 | 1 |

PSY: Phytoene synthase; PTOX: plastid terminal oxidase; βCHY: β-carotene hydroxylase; LεCY: lycopene ε-cyclase; ZEP: zeaxanthine epoxidase; VDE: violaxanthine de-epoxidase; NCED3: 9-cis-epoxycarotenoid dioxygenase; CCD1: carotenoid cleavage dioxygenase 1; FIB: Fibrillin; PDH: phytoene dehydrogenase-like.

A. Phytoene Synthase

The first true carotenoid is formed by the condensation of two molecules of geranylgeranyl diphosphate into phytoene and is catalyzed by the enzyme phytoene synthase (PSY; EC 2.5.1.32). A partial-length cDNA clone encoding PSY (cccs30w7e6) was identified in the Cornell *Coffea canephora* EST database. Because this clone was missing the 5' end of the ORF, genome walking was employed to recover the missing 258 bp 5' sequence. Using nested primers GWPSY1 (5'-ACTTCACCGCAGCGATCATAAGCTTCAC-3') (SEQ ID NO.:26) and GWPSY2 (5'-TTCACGTCCCAATCTTCTC-GAGATCTC-3') (SEQ ID NO.:27) a fragment approximately 1800 bp in length was recovered, cloned into pCR4-TOPO to make pCR4-GWPSY1, and sequenced. In "silico" assembly of the sequence revealed the full-length ORF of PSY. As shown in Table 3, the deduced amino acid sequence of CcPSY was determined to have 76% identity to the *Capsicum annuum* PSY1 (X68017; Romer et al., 1993), 74% identity to the *Lycopersion esculentum* PSY1 (X60441; Ray et al., 1992) and 70% identity to *Arabidopsis thaliana* PSY (NM_121729).

TABLE 3

Identity of the *Coffea canephora* phytoene synthase amino acid sequence with the most homologous GenBank sequences. NP = Not published.

| Gene name (accession number) | Publication | % identity[1] |
|---|---|---|
| *Coffea canephora* | NP[2] | 100 |
| *Capsicum annuum* (X68017) | Romer et al., 1993 | 76 |
| *Lycopersicon esculentum* (X60441) | Ray et al., 1992 | 74 |
| *Arabidopsis thaliana* (NM_121729) | NP | 70 |

[1]Identities were individually calculated with clustal W using default parameters with the full-length ORF
[2]NP = not published The condensation of two molecules of geranylgeranyl diphosphate into phytoene by PSY has been found to be a rate-limiting reaction in several different plant species and tissues at different stages of development. The over-expression of PSY in a grain specific manner is thus expected to be useful for the overproduction of carotenoids and carotenoid-derived flavor molecules in the coffee grain. Seed-specific over expression of PSY has been carried out in other species. For example, the seed-specific over-expression of PSY in *Arabidopsis* led to increased carotenoids, increased chlorophyll content, a delay in germination and an increase in ABA (Lindgren et al., 2003). Seed specific over-expression of PSY and a bacterial phytoene desaturase (CRTI, from *Erwinia uredovora*) in rice endosperm was shown to drive β-carotene synthesis as well as the formation of further downstream xanthophylls (Beyer et al., 2002; Paine et al., 2005). Overexpression of PSY in canola seeds led to a 50-fold increase in carotenoid production (Shewmaker et al, 1999).

Figure 4A:
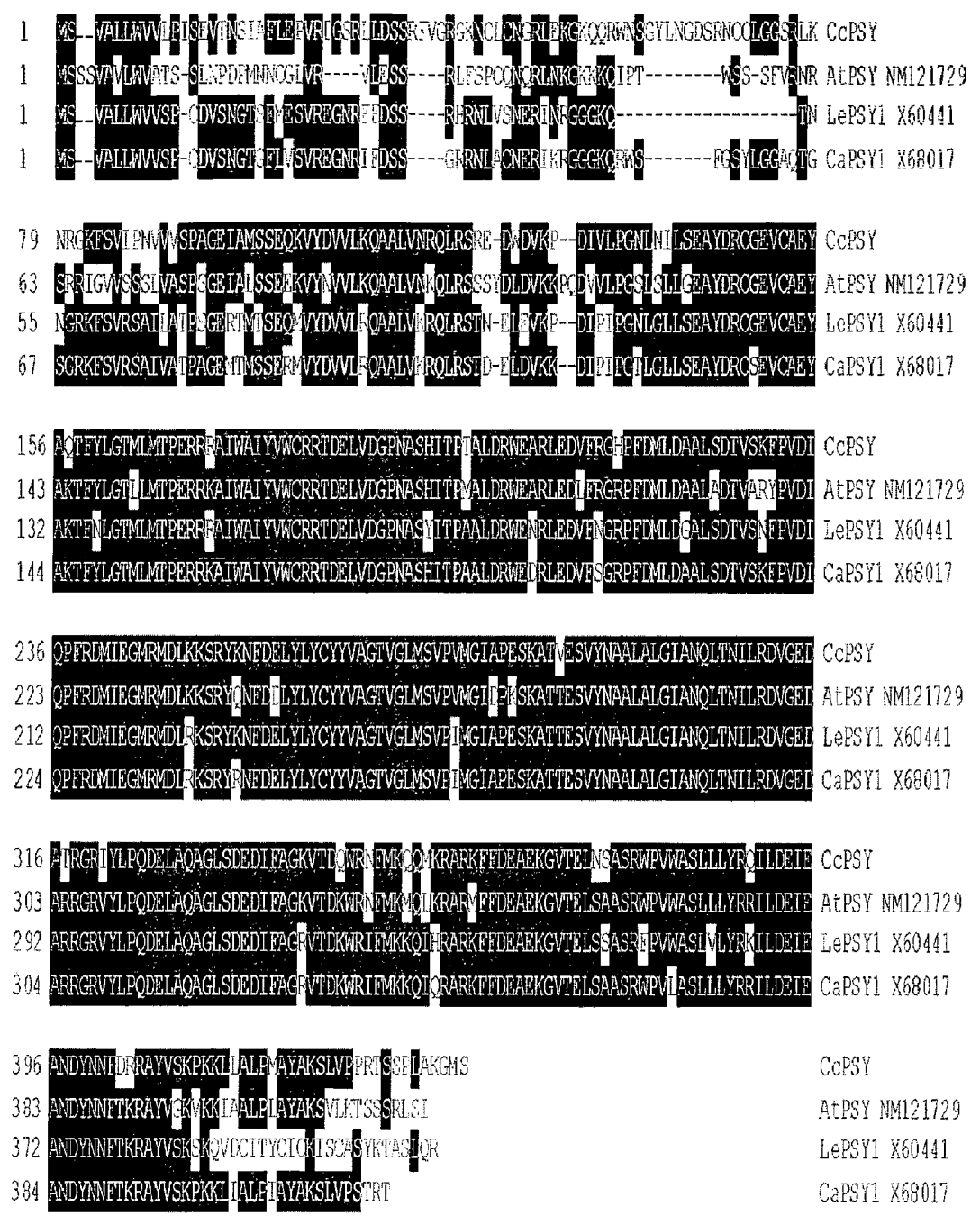

FIG. 4A shows the *Coffea canephora* (CcPSY) amino acid sequence aligned with the most homologous sequences in the GenBank non-redundant protein database.

B. Phytoene desaturase, ζ-carotene desaturase and lycopene cyclases

Phytoene can undergo four consecutive desaturation steps catalyzed by the enzymes phytoene desaturase (PDS; EC 1.3.99) and 4-carotene desaturase (ZDS; EC 1.14.99.30) (Bartley et al., 1992, Hugueney et at., 1992; Albrecht et al., 1995). These desaturation steps require the presence of a plastid terminal oxidase (PTOX) as a co-factor.

i) Phytoene Dehydrogenase

Figure 1:
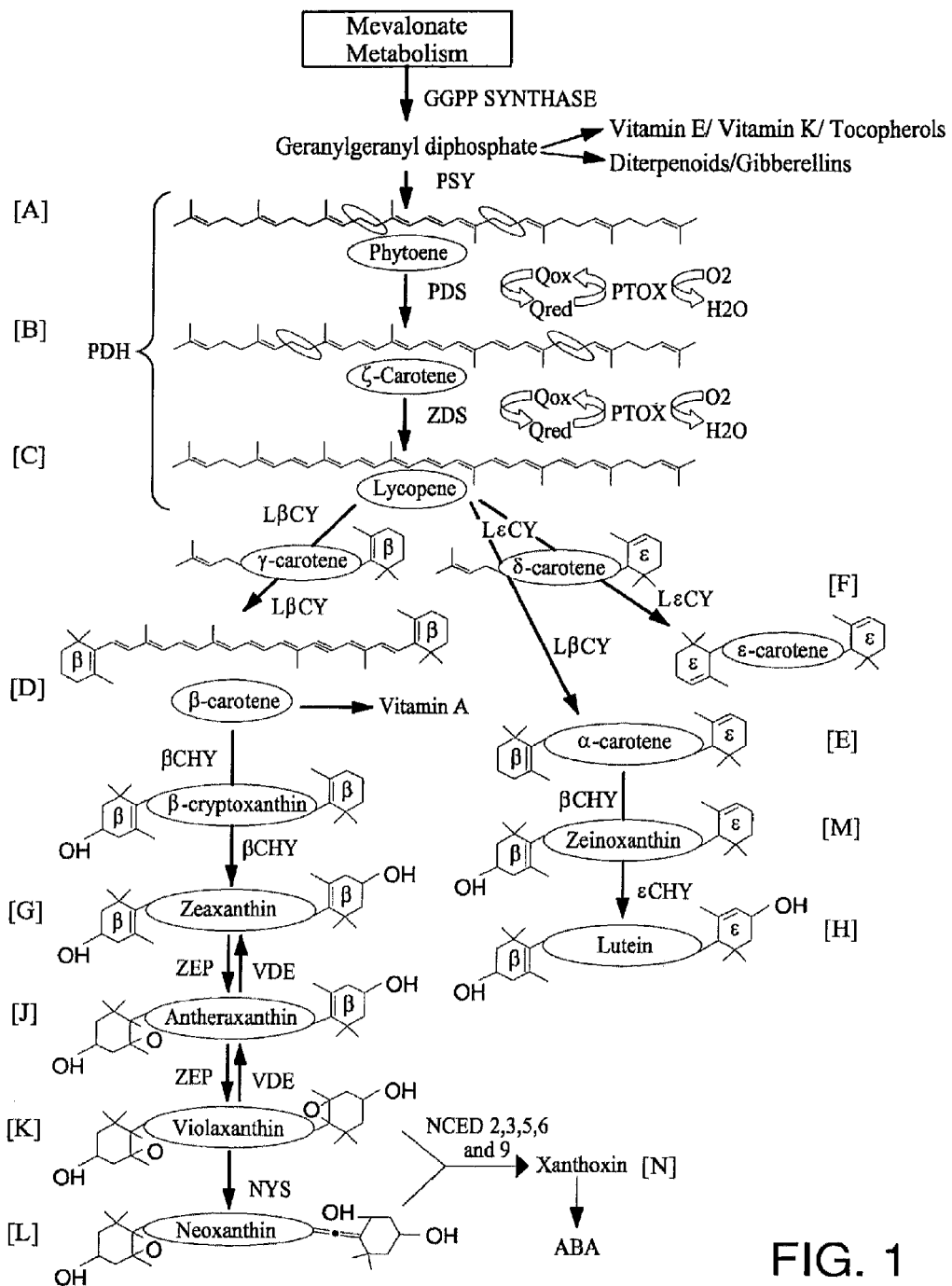

No corresponding sequences were detected in the EST database for PDS or ZDS. However, two partial length clones (PDH, ccc131g22; PDH2, cccs46w13n19) encoding phytoene dehydrogenase-like (PDH) proteins were detected. The coffee PDH1 was found to have 72% homology to an *Arabi*- dopsis PDH-like and 23% homology to the *Phycomyces blakesleeanus* PDH protein. The *Phycomyces blakesleeanus* PDH protein is capable of introducing the four double bonds into phytoene to form lycopene, thereby replacing PDS and ZDS in *Phycomyces* (Arrach et al., 2001; see FIG. 1). It is believed that this protein carries out a similar function in one or more coffee tissues.

ii) Phytoene Desaturase

Because clone for PDS was found in the coffee EST libraries, experiments were carried out to generate a PDS cDNA clone de-novo. These experiments resulted in the generation of a partial PDS cDNA of 897 bp using RT-PCR with cDNA generated from yellow robusta grain. RT-PCR was carried out using the degenerate primers DegPDS2 FWR (5'-GGTG-GAAAGRTAGCTGCATGGA-3') (SEQ ID NO.:46) and DegPDS4 REV (5'-TGTTACRGACATGTCAGCATACAC-3') (SEQ ID NO.:47), which were designed from the conserved peptide sequences GGKVAAW (SEQ ID NO.:48) and VYADMSVT (SEQ ID NO.:49) found in LePDS (CAA55078), CaPDS (CAA48195) and AtPDS (AAA20109). The PCR product of 897 bp was cloned in pCR4-TOPO to generate pCR4-PDS. Using the Genewalker kit, the partial coding sequence of PDS was extended using nested primers GWPDS1 (5'-ATCATTGAATGCTCCTTC-CACTGCAAC-3') (SEQ ID NO.:50) and GWPDS2 (5'-TCATTAATTCCTAGTTCTCCAAACAGG-3') (SEQ ID NO.:51), resulting in the generation of a fragment of 2066 bp. This fragment was cloned into pCR4-TOPO to generate pCR4-GWPDS#5. The resulting clone was sequenced resulting in an additional 225 bp of the coding sequence and a partial open-reading frame of 1077 bp containing 3 introns of 616 bp, 373 bp and 609 bp at positions 122 bp, 215 bp and 272 bp of the partial ORF, respectively. FIG. 4B shows the *Coffea canephora* (CcPDS) partial PDS amino acid sequence deduced from plasmids pCR4-CcPDS and pCR4-GW-PDS#5. The partial ORF was aligned with the most homologous sequences in the GenBank non-redundant protein database

TABLE 4

Identity of the *Coffea canephora* phytoene desaturase amino acid sequence with the most homologous GenBank sequences

| Gene name (accession number) | Publication | % identity[1] |
|---|---|---|
| *Coffea canephora* (*****) | NP[2] | 100 |
| *Capsicum annuum* (X68058) | Hugueney et al., 1992 | 89 |
| *Lycopersicon esculentum* (X59948) | Pecker et al., 1992 | 89 |
| *Arabidopsis thaliana* (TC261857) | TIGR | 85 |

[1]Identities were individually calculated with clustal W using default parameters with partial PDS sequence from *Coffea canephora* and the corresponding regions from orthologues
[2]NP = not published iii) Zeta-Carotene Desaturase Because no clone for ZDS was found in the coffee EST libraries, experiments were carried out to generate a ZDS cDNA clone de-novo. These experiments resulted in the generation of a partial ZDS cDNA of 472 bp using RT-PCR with cDNA generated from yellow robusta grain. The RT-PCR was carried out using the non-degenerate primers DegZDS1 FWR (5'-TTGCAGGCATGTCGACTGCTG-3') (SEQ ID NO.:52) and DegZDS3 REV (5'-GTGGGATCCTGTTGCATAT-GCTCT-3') (SEQ ID NO.:53), which were designed from the conserved peptide sequences LAGMSTAV (SEQ ID NO.:54) and MWDPVAYAL (SEQ ID NO.:55) of LeZDS (AF195507), CaZDS (X89897) and AtZDS (U38550) orthologues.

Figure 4C:
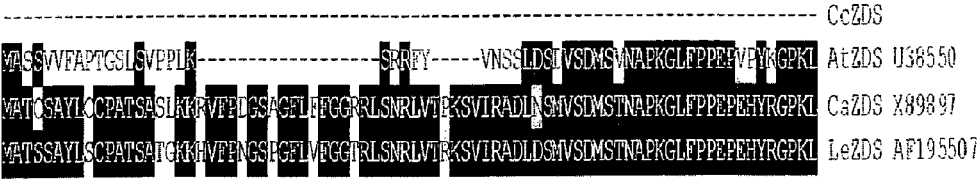
FIG. 4. Optimal alignment of *Coffea canephora* protein sequences with the closest databank sequences. A) CcPSY (SEQ ID NO.:13) aligned with AtPSY (SEQ ID NO.:94), LePSY1 (SEQ ID NO.:95), and CaPSY1 (SEQ ID NO.:96); B) CcPDS (SEQ ID NO.:14) aligned with AtPDS (SEQ ID NO.:97), LePDS (SEQ ID NO.:98), and CaPDS (SEQ ID NO.:99); C) CcZDS (SEQ ID NO.:24) aligned with AtZDS (SEQ ID NO.:100), CaZDS (SEQ ID NO.:101), and LeZDS (SEQ ID NO.:102); D) CcPTOX (SEQ ID NO.:15) aligned with AtPTOX (SEQ ID NO.:103), CaPTOX (SEQ ID NO.:104), and CaPTOX (SEQ ID NO.:105); E) CcβCHY (SEQ ID NO.:16) aligned with AtβCHY (SEQ ID NO.:106), and Leβ-CHY (SEQ ID NO.:107); F) CcLεCY (SEQ ID NO.:17) aligned with LsLεCY (SEQ ID NO.:108), and TeLεCY (SEQ ID NO.:108); G) CcZEP (SEQ ID NO.:18) aligned with LeZEP (SEQ ID NO.:109), PdZEP (SEQ ID NO.:110), OsZEP (SEQ ID NO.:111), and AtZEP (SEQ ID NO.:112); H) CcVDE (SEQ ID NO.:19) aligned with AtVDE (SEQ ID NO.:113), OsVDE (SEQ ID NO.:114), and NtVDE (SEQ ID NO.:115); I) CcNCED3 (SEQ ID NO.:20) aligned with AtNCED3 (SEQ ID NO.:116), AtNCED5 (SEQ ID NO.: 117), LeNCED1 (SEQ ID NO.:118), StNCED1 (SEQ ID NO.:119), and VvNCED1 (SEQ ID NO.:120); J) CcCCD1 (SEQ ID NO.:21) aligned with PhCCD1 (SEQ ID NO.:121), LeCCD1B (SEQ ID NO.:122), LeCCD1A (SEQ ID NO.:123), and AtCCD1 (SEQ ID NO.:124); and K) CcFIB (SEQ ID NO.:22) aligned with AtFIB1b (SEQ ID NO.:125), AtFIB1a (SEQ ID NO.:126), CaFIB (SEQ ID NO.:127), and LeFIB (SEQ ID NO.:128). The alignments were generated with the clustal W program in the Lasergene software package (DNASTAR) and then adjusted manually to optimize the alignment.

The PCR product of 472 bp was cloned in pCR4-TOPO to generate pCR4-ZDS#1. FIG. 4C shows the *Coffea canephora* (CcZDS) partial ZDS amino acid sequence deduced from the plasmid pCR4-CcZDS#1 in an alignment with the most homologous sequences in the GenBank non-redundant protein database. Table 5 shows the % identity of the sequences in FIG. 4C in the regions of overlap. The high levels of homology are consistent with the notion that pCR4-Cc-ZDS#1 encodes a partial cDNA encoding the *Coffea canephora* ZDS gene CcZDS. The remaining 5' and 3' coding regions of this gene can be obtained using the well-known techniques of 5' and 3' RACE and primer assisted walking.

TABLE 5

Identity of the *Coffea canephora* zeta-carotene desaturase amino acid sequence with the most homologous GenBank sequences. NP = Not published.

| Gene name (accession number) | Publication | % identity[1] |
|---|---|---|
| *Coffea canephora* | NP[2] | 100 |
| *Capsicum annuum* (X89897) | Albrecht et al., 1995 | 92 |
| *Lycopersicon esculentum* (AF195507) | Bartley and Ishida, 1999 | 92 |
| *Arabidopsis thaliana* (U38550) | Scolnik and Bartley, 1995 | 85 |

[1]Identities were individually calculated with clustal W using default parameters with partial ZDS sequence from *Coffea canephora* and the corresponding regions from orthologues
[2]NP = not published iv) Plastid Terminal Oxidase A full-length cDNA clone encoding PTOX (ccc124o10), a co-factor for phytoene desaturation (Carol et al., 1999; Josse et al., 2000; for review see Kuntz, 2004), was detected in the *C. canephora* EST database. Alignment of PTOX with the most homologous GenBank sequences revealed 60% homology to the tomato (AF177980), and 61% homology to the pepper (AF177981), and 46% homology to the *Arabidopsis* (AJ004881) PTOX proteins (see Table 6). The C-terminal amino acid sequence was aligned with the three closest sequences in the NCBI database. This alignment is set forth in FIG. 4D.

TABLE 6

Identity of the *Coffea canephora* plastid terminal oxidase amino acid sequence with the most homologous GenBank sequences.

| Gene name (accession number) | Publication | % identity[1] |
|---|---|---|
| *Coffea canephora* | NP[2] | 100 |
| *Capsicum annuum* (AF177981) | Josee et al., 2000 | 61 |
| *Lycopersicon esculentum* (AF177980) | Josse et al., 2000 | 60 |
| *Arabidopsis thaliana* (AJ004881) | Carol et al., 1999 | 46 |

[1]Identities were individually calculated with clustal W using default parameters with the full-length ORF
[2]NP = not published Lycopene itself is the precursor of pseudoionone (FIG. 2V) via a 9' 10 cleavage dioxygenase (CCD1; Simkin et al., 2004b) and 6-methyl-5-hepten-2-one (MHO) via a 5'6 cleavage dioxygenase (CCD4; Bouvier et al., 2004a). Both MHO and pseudoionone are potent contributors to tomato fruit flavor (Buttery et al., 1990; Baldwin et al., 2000). Without intending to be bound to any particular theory, it is believed that although neither has been detected in coffee grain to date, these carotenoid-derived products may go undetected because they co-elute with other more abundant volatiles in coffee.

β-carotene is formed by the enzyme lycopene β-cyclase (LβCY; Cunningham et al., 1996), which introduces two β-ring structures at the ends of the carbon chain and α-carotene is formed by the enzymes lycopene ε-cyclase (LεCY; Ronen et al., 1999) and LβCY, which introduce one ε-ring and one β-ring respectively. A corresponding cDNA for a putative coffee LεCY (cccp8f16) has been identified in the Nestlé-Cornell C. canephora EST database.

C. β-Carotene Hydroxylase

Oxygenated carotenoids are formed by two successive hydroxylation steps. β-carotene is converted zeaxanthin by the action of the enzyme β-carotene hydroxylase (βCHY; EC 1.14.13-; Sandmann, 1994) and α-carotene is converted to lutein by the actions of βCHY and ε-carotene hydroxylase (εCHY) together. εCHY has only recently been cloned (Tian at al., 2004; Tian and DellaPenna, 2004; for review see Inoue, 2004), and a lutein deficient mutant (lut1) has been characterised (Pogson et al., 1996; Tian and DellaPenna, 2001).

A full-length clone (cccs46w21b8)+intron encoding a protein with 73% identity to L. esculentum (Y14809; Hirshberg et al., 1998) ACHY, and 67% identity to the A. thaliana (NM_124636) βCHY has been identified in the C. canephora EST database (see Table 7).

TABLE 7

Identity of the Coffea canephora β-carotene hydroxylase complete amino acid sequence with the most homologous GenBank sequences. NP = Not published.

| Gene name (accession number) | Publication | % identity[1] |
|---|---|---|
| Coffea canephora | NP[2] | 100 |
| Lycopersicon esculentum (Y14809) | Hirschberg et al., 1998 | 73 |
| Arabidopsis thaliana (NM_124636) | NP[2] | 67 |

[1]Identities were individually calculated with clustal W using default parameters with the full-length ORF
[2]NP = not published FIG. 4E shows the CcβCHY amino acid sequence aligned with the most homologous sequences in the GenBank non-redundant protein database shown in Table 7.

D. Lycopene ε-Cyclase

Lycopene is converted to α-carotene (β,ε-carotene, FIG. 1E) and β-carotene by the activity of two enzymes, lycopene δ-cyclase (LεCY; Ronen et al., 1999) and lycopene β-cyclase (LβCY). LεCY introduces one ε-ring and LβCY introduces one β-ring to form α-carotene. The activity of LεCY also results in the formation of the intermediate δ-carotene (ε,ψ-carotene) having one ε-ring and one uncyclized psi end. In plants such as Lactuca sativa (lettuce), LεCY introduces two ε-ring structures at the ends of the carbon chain, resulting in the formation of ε-carotene (ε,ε-carotene; Cunningham and Gantt 2001) (FIG. 1F).

A partial cDNA (pcccp8f16) representing the C-terminal domain of a protein with 86% identity to T. erecta (AF251016; Moehs et al., 2001) βLεCY and 77% identity to the L. sativa (AF321538; Cunningham et al., 2001) LεCY has been identified in the C. canephora EST database (Table 8).

TABLE 8

Identity of the Coffea canephora Lycopene ε-cyclase C-terminal amino acid sequence with the most homologous GenBank sequences. NP = Not published.

| Gene Gene name (accession number) | Publication | % identity[1] |
|---|---|---|
| Coffea canephora | NP[2] | 100 |
| Tagetes erecta (AF251016) | Moehs et al,. 2001 | 86 |
| Lactuca sativa (AF321538) | Cunningham et al., 2001 | 77 |

[1]Identities were individually calculated with clustal W using default parameters with with partial LεCY sequence from Coffea canephora and the corresponding regions from orthologues
[2]NP = not published FIG. 4F shows the C-terminal partial CcLεCY amino acid sequence aligned with the most homologous sequences in the GenBank non-redundant protein database.

E. Zeaxanthin Epoxidase and Violaxanthin De-Epoxidase

The hydroxylated β-rings of zeaxanthine are epoxylated by the enzyme zeaxanthine epoxidase (ZEP; Marin et al., 1996; Bouvier et al., 1996) and de-epoxylated by the activity of violaxanthine de-epoxidase (VDE) in a reversible cycle implicated in the adaptation of plastids to changing environmental light conditions. Partial cDNAs clones for both VDE (cccp13a9) and ZEP (ccc129g15) were identified in the C. canephora EST database.

The deduced C-terminal amino acid sequence of Coffea canephora ZEP (CcZEP) was aligned with the most homologous GenBank sequences, and found to encode a protein with 72% homology to the C-terminal amino acid sequence of L. esculentum (Z83835; Burbridge et al., 1997) ZEP, 71% homology to the C-terminal amino acid sequence of Prunus armeniaca (AF159948; Mbeguie-A-Mbeguie and Fils-Lycaon, 2000) ZEP, 60% homology to the C-terminal amino acid sequence of Oryza sativa (AB050884; Agrawal et al., 2001) ZEP, and 52% homology to the C-terminal amino acid sequence of Arabidopsis thaliana (NM_126103) ZEP (Table 9).

TABLE 9

Identity of the Coffea canephora zeaxanthin epoxidase C-terminal amino acid sequence with the most homologous GenBank sequences. NP = Not published.

| Gene name (accession number) | Publication | % identity[1] |
|---|---|---|
| Coffea canephora | NP[2] | 100 |
| Lycopersicon esculentum (Z83835) | Burbidge, 1997 | 72 |
| Prunus armeniaca (AF159948) | Mbeguie-A-Mbeguie, 2000 | 71 |
| Oryza sativa (AB050884) | Agrawal et al., 2001 | 60 |
| Arabidopsis thaliana (NM_851285) | NP | 52 |

Figure 4G:
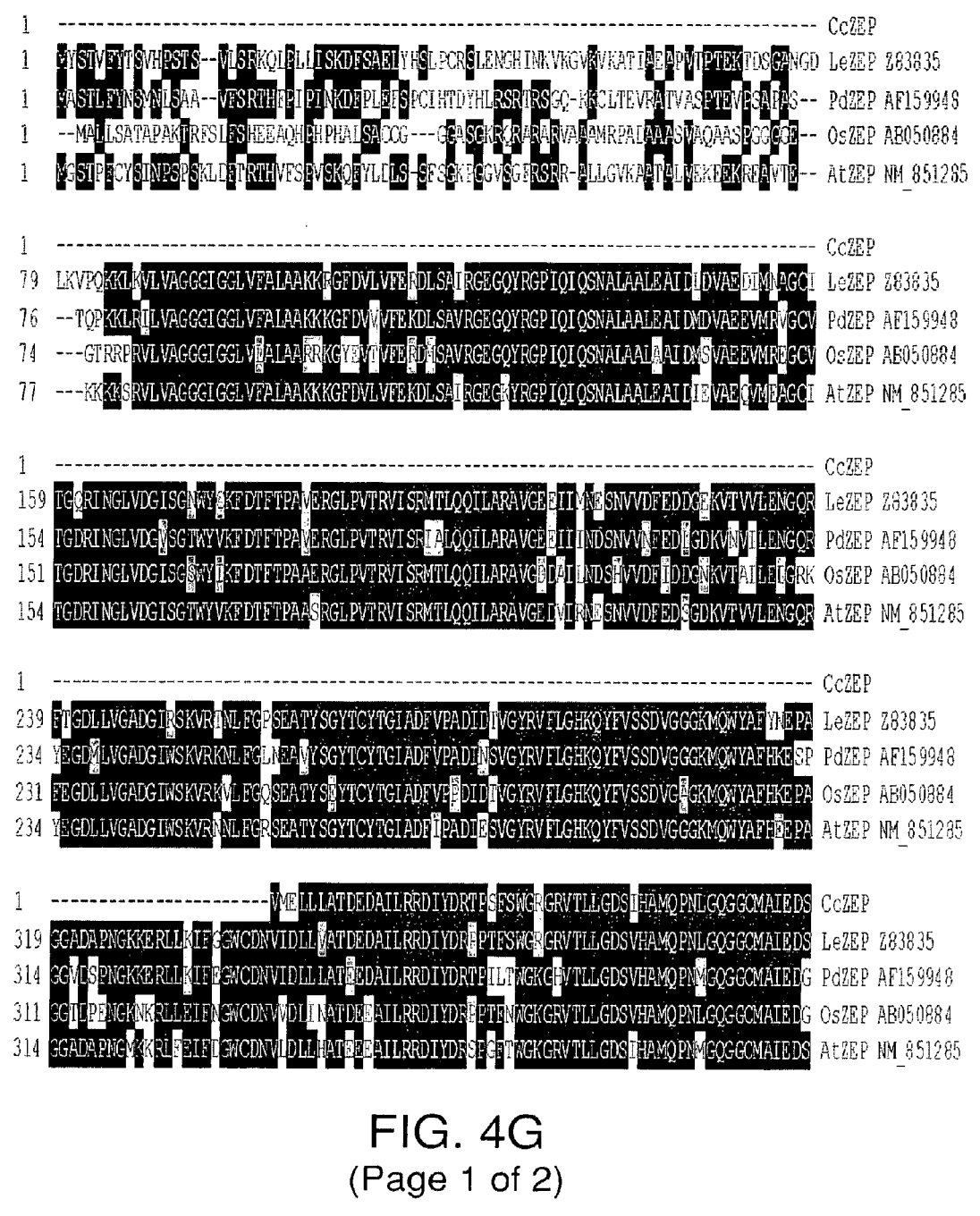
Figure 4G:
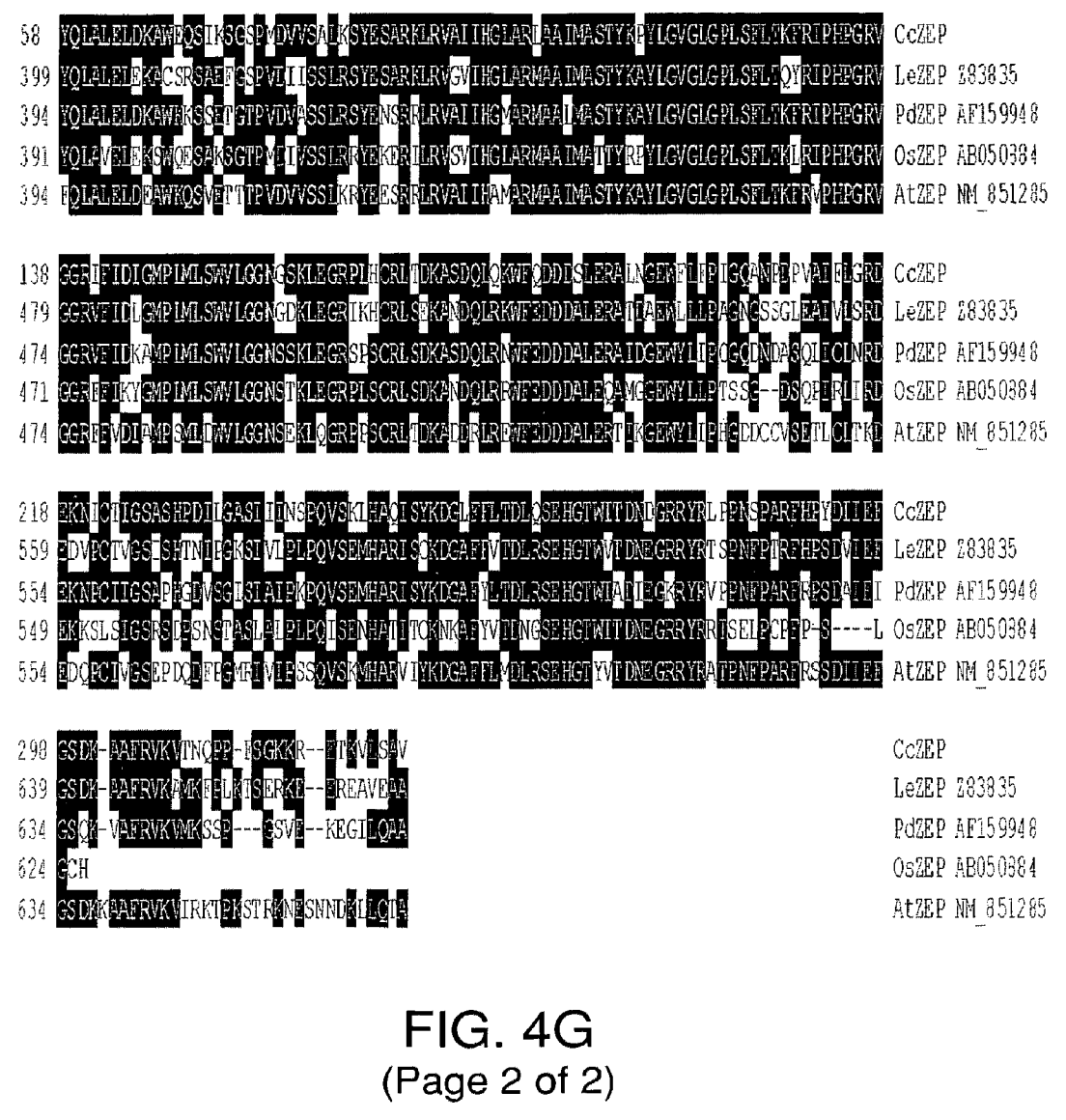

[1]Identities were individually calculated with clustal W using default parameters with with partial ZEP sequence from Coffea canephora and the corresponding regions from orthologues.
[2]NP = not published FIG. 4G shows the N-terminal partial CcZEP amino acid sequence aligned with the most homologous sequences in the GenBank non-redundant protein database.

A partial length cDNAs clone of VDE (ccc129g15, insert 1132 bp) was identified in the C. canephora Nestlé-Cornell EST database. The coding sequence of this gene was extended using the GenomeWalker kit. The remaining part of the ORF of CcVDE was obtained using GenomeWalker kit and nested primers GWVDE1 (5'-ACATTTCTTTCGT-GAGACTGCACACTC-3') (SEQ ID NO.:30) and GWVDE2 (5'-ATCACCACATTTGATCTGGCATTCAGTC-3') (SEQ ID NO.:31). This genome walk resulted in the generation of a 2.3 kb fragment. This fragment was cloned into pCR4-TOPO to generate pCR4-GWVDE. The insert of this clone was sequenced resulting in the full length ORF of 1248 bp after in-silico reconstruction.

The deduced full-length amino acid sequence of *Coffea canephora* VDE (CcVDE) was aligned with the most homologous GenBank sequences, and found to encode a protein with 74% homology to the amino acid sequence of *Nicotiana tabacum* (U34817; Bugos et al., 1998) VDE, 67% homology to the amino acid sequence of *Oryza sativa* (AF411133) VDE, and 67% homology to the *Arabidopsis thaliana* (AY063067) VDE (Table 10).

TABLE 10

Identity of the *Coffea canephora* violaxanthin de-epoxidase amino acid sequence with the most homologous GenBank sequences. NP = Not published.

| Gene name (accession number) | Publication | % identity[1] |
|---|---|---|
| *Coffea canephora* | NP[2] | 100 |
| *Nicotiana tabacum* (U34817) | Bugos et al., 1998 | 74 |
| *Oryza sativa* (AF411133) | NP | 67 |
| *Arabidopsis thaliana* (AY063067) | NP | 67 |

[1]Identities were individually calculated with clustal W using default parameters with the full-length ORF
[2]NP = not published FIG. 4H shows the full CcVDE amino acid sequence aligned with the three most homologous sequences in the GenBank non-redundant protein database.

F. 9-Cis-Epoxycarotenoid Dioxygenase 1

A partial clone of a 9-cis-epoxycarotenoid dioxygenase (NCED3; cccwc22w23o20), involved in synthesis of the phytohormone abscisic acid from neoxanthine (Tan et al. 1997) was detected in the *C. canephora* EST database. In *Arabidopsis thaliana*, 5 cDNAs are responsible for this 9-cis cleavage reaction, NCED2 (NM117945), NCED3 (NM112304), NCED5 (NM102749), NCED6 (NM113327), and NCED9 (NM106486). The *C. canephora* cDNA identified here showed highest orthology to the AtNCED3 (NM112304) and was thus named CcNCED3. ABA is a carotenoid-derived apocarotenoid formed by the action of NCED3 (Tan et al., 1997). NCEDs are 11,12-carotenoid cleavage dioxygenases, which cleave neoxanthin, in a similar reaction to the formation of a variety of carotenoid derived apocarotenoids implicated in flavor and aroma of various plant foods, to form xanthoxin, the precursor of ABA.

CcNCED3 full coding sequence was obtained using the GenomeWalker kit and nested primers GWNCED3F (5'-AAGCAGAAGCAGTCAGGGACTTCTACC-3') (SEQ ID NO.:40) and GWNCED3R (5'-TATCCAGTACAC-CGAATCTTGACACC-3') (SEQ ID NO.:41), generating a fragment of 2.5 kb. This fragment was cloned into pCR4-TOPO to generate pCR4-GWNCED#4. The insert of this clone was sequenced resulting in the full-length ORF of 1908 bp and 1104 bp, upstream of the ATG. Like all reported NCEDs, CcNCED3 contains no introns. The deduced N-terminal amino acid sequence of *Coffea canephora* NCED3 (CcNCED3) was aligned with the most homologous GenBank sequences, and found to encode a protein with 75% homology to the amino acid sequence of *L. esculentum* (CAD30202; Thompson et al., 2004) NCED1, 75% homology to the *Solanum tuberosum* (AAT75151) NCED1, 70% homology to the *Vitis vinifera* (AF159948; Sato et al., 2004) NCED1, and 66% homology to the *Arabidopsis thaliana* (BAB01336) NCED3 (Table 11).

TABLE 11

Identity of the *Coffea canephora* 9-cis-epoxycarotenoid dioxygenase 1 amino acid sequence with the most homologous GenBank sequences. NP = Not published.

| Gene name (accession number) | Publication | % identity* |
|---|---|---|
| *Coffea canephora* | NP[2] | 100 |
| *Solanum tuberosum* (AAT75151) | NP[2] | 75 |
| *Lycopersicon esculentum* (CAD30202) | Thompson et al 2004 | 75 |
| *Vitis vinifera* (AAR11193) | Soar et al., 2004 | 70 |
| *Arabidopsis thaliana* (NM112304)) | Sato et al., 2000 | 66 |
| *Arabidopsis thaliana* (NM102749) | Sato et al., 2000 | 63 |

Figure 4I:
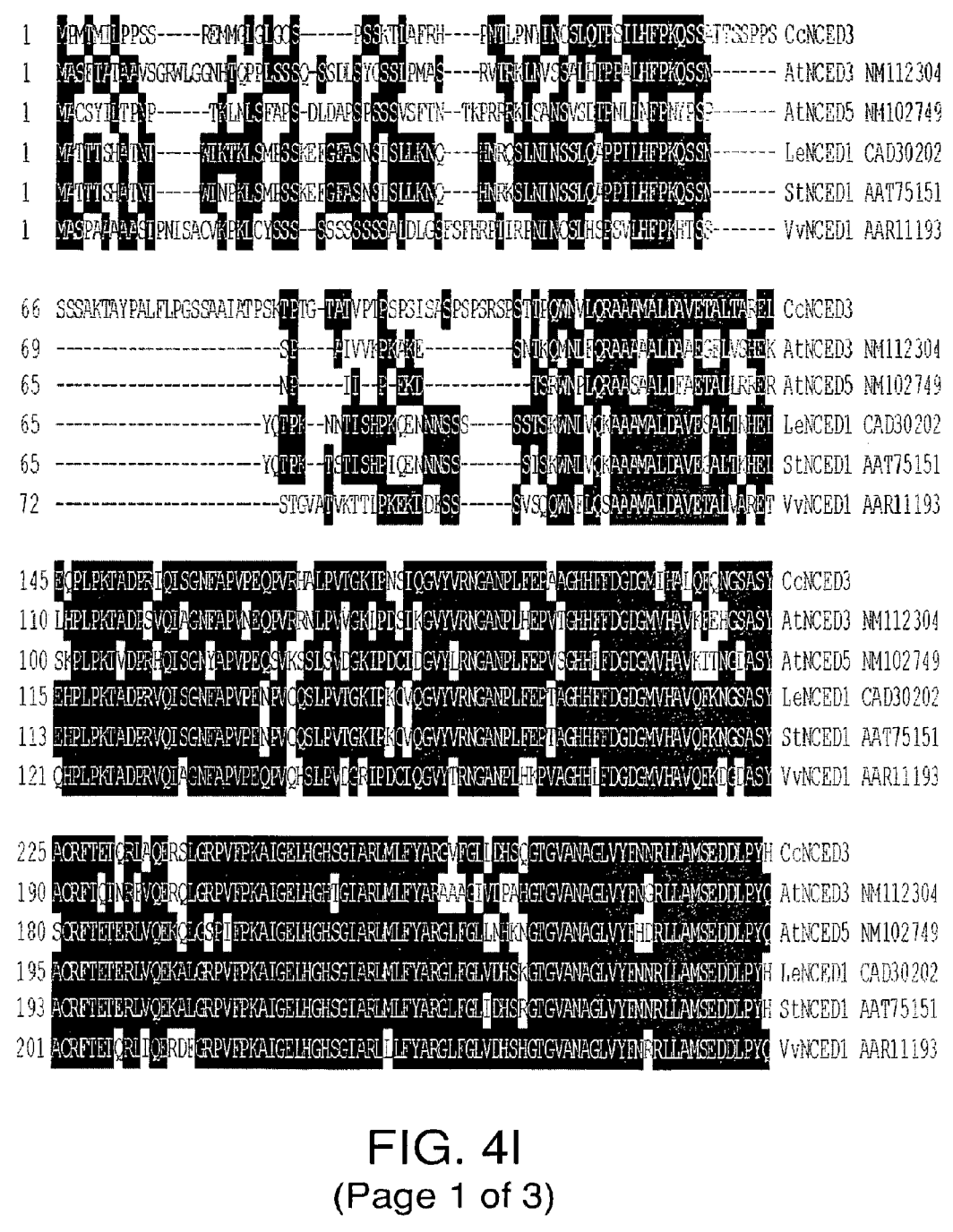

1. Identities were individually calculated with clustal W using default parameters with the full-length ORF
[2]NP = not published FIG. 4I shows the CcNCED3 full amino acid sequence aligned with the four most homologous sequences in the GenBank non-redundant protein database.

G. Carotenoid Cleavage Dioxygenase 1

Figure 2:
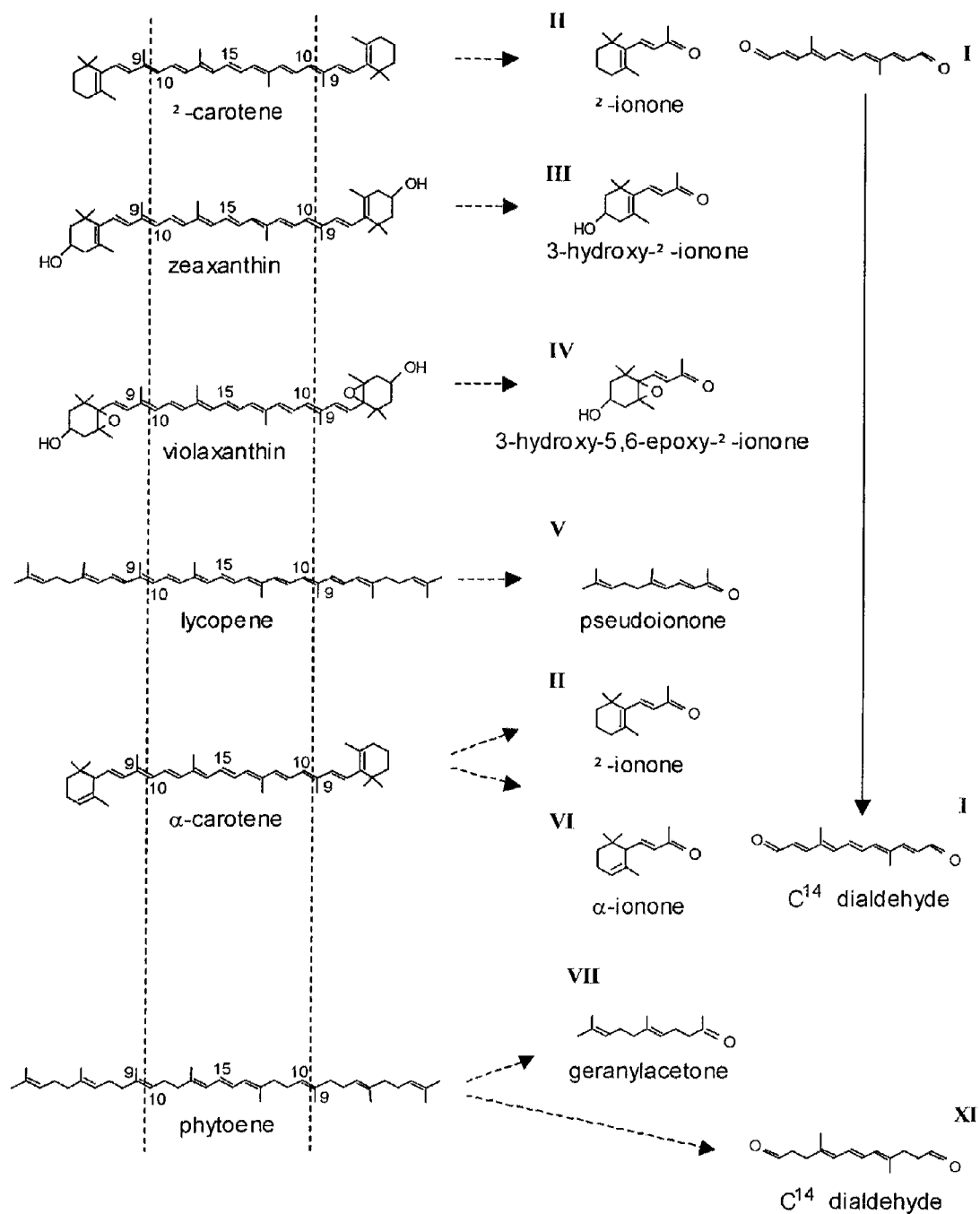
FIG. 2. Scheme for the reactions catalyzed CCD1 proteins. The carotenoid substrates (left) when cleaved at the 9,10 and 9',10' positions (indicated by dotted line) would yield two monoaldehydes and a central dialdehyde product. I, 4,9-dimethyldodeca-2,4,6,8,10-pentaene-1,12-dial ($C_{14}$ dialdehyde). II, 9-apo-β-caroten-9-one (β-ionone). III, 3-hydroxy-9-apo-β-caroten-9-one (3-hydroxy-α-ionone). IV, 3-hydroxy-5,6-epoxy-9-apo-α-caroten-9-one (3-hydroxy-5'6-epoxy-β-ionone). V, 6,10-dimethyl-3,5,9-undecatrien-2-one (pseudoionone). VI, 9-apo-α-caroten-9-one (α-ionone). VII, 6,10-dimethyl-5,9-undecatrien-2-one (geranylacetone).
Figure 3:
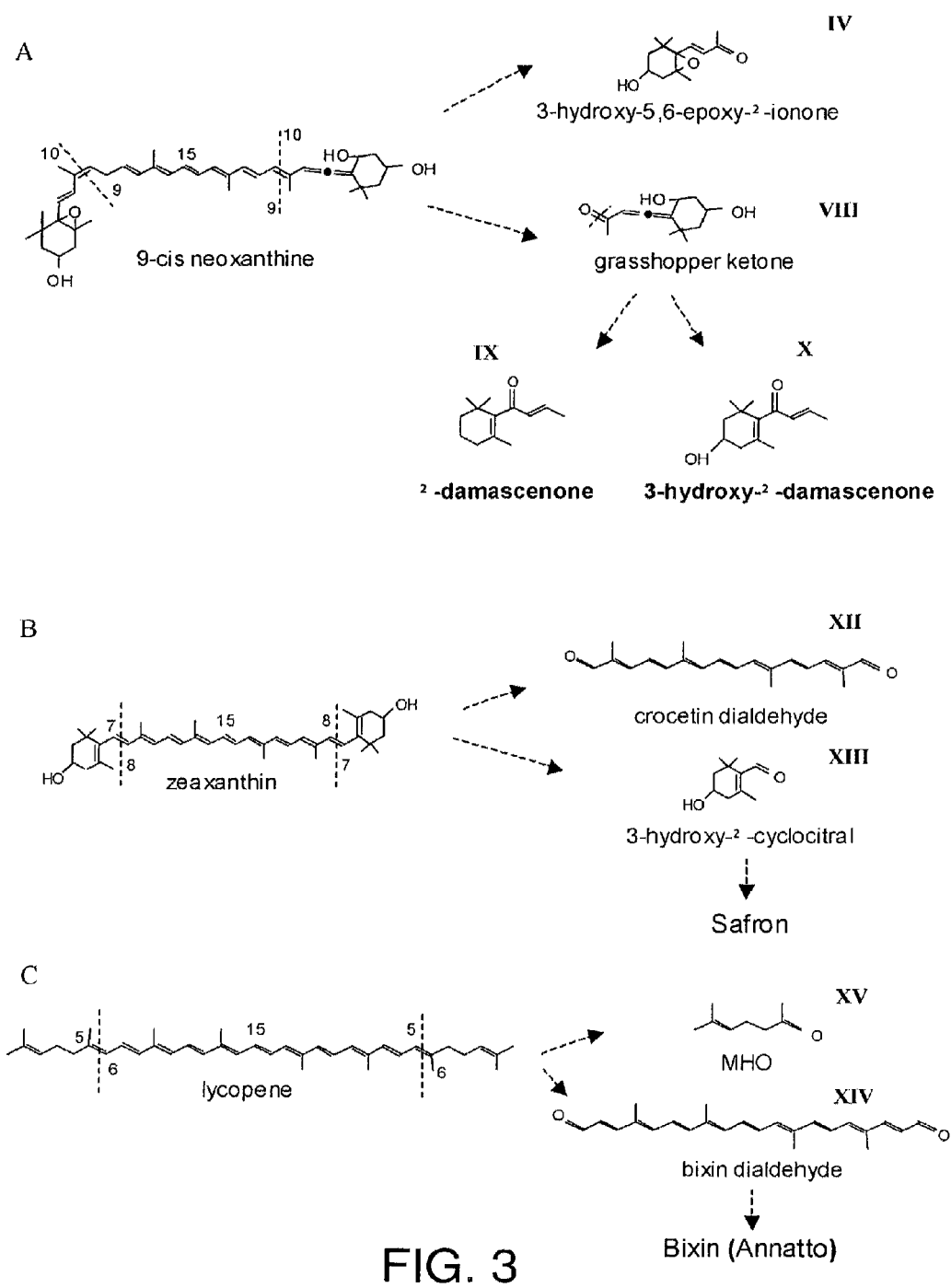
FIG. 3. Schematic for CCD-catalyzed formation of aroma compounds. A) Neoxanthine is cleaved to form VIII, (3S,5R, 6R)-3,5-dihydroxy-6,7-didehydro-5,6-dihydro-9-apo-β-caroten-9-one (grasshopper ketone; Schwartz et al., 2001) by the 9,10(9'10) cleavage dioxygenase CCD1. The grasshopper ketone is the precursor for the formation of IX, β-damascenone and X, 3-hydroxy-β-damascenone (Suzuki et al., 2002). B) CsZCD is a 7,8(7'8) cleavage dioxygenase resulting in the formation of 3-hydroxy-β-cyclocitral from zeaxanthine. C) BoLCD is a lycopene specific 5,6(5'6) cleavage dioxygenase resulting in the formation of the $C_7$ cleavage product previously identified as 6-methyl-5-hepten-2-one (MHO).

Carotenoid Cleavage Dioxygenase 1 (CCD1) has been shown to be involved in the formation of β-ionone, α-ionongeranylacetone, and pseudoionone in vivo (Simkin et al., 2004b; see FIG. 2). This gene is of particular interest due to its role in the formation of the $C_{13}$ grasshopper ketone from Neoxanthin (FIG. 3). Without being bound to any particular theory or mechanism of action, the grasshopper ketone is postulated to be the precursor for the formation of β-damascenone and 3-hydroxy-β-damascenone (Suzuki et al., 2002) (FIG. 2), which are important flavor volatiles of green and roasted coffee.

A partial cDNA sequence (pcccwc22w2a6) for the *Coffea canephora* CCD1 (CcCCD1) was identified in the *C. canephora* EST database. The missing 5' sequence was recovered using the GenomeWalker kit and the primers GWCCD11 (5'-AACAATCCGAACAGCCCCTTGAGATCCC-3') (SEQ ID NO.:34) and GWCCD12 (5'-GTTTAAGCCTTGAT-GTCTTCACGTACCG-3') (SEQ ID NO.:35). A fragment of 2475 bp was recovered and cloned into pCR4-TOPO to generate pCR4-GWCCD1 #1, and the insert of this clone was sequenced. Because this step did not produce a full length coding sequence, a second round of genome walking was carried out, using the nested primers GWCCD13 (5'-TGC-CAAGTTACTGTTCAATGACTAGGC-3') (SEQ ID NO.:36) and GWCCD14 (5'-AAGCAATTTAATCCCGTC-CTTAATCTGG-3') (SEQ ID NO.:37), and a fragment of 1045 bp was recovered. This fragment was cloned into pCR4-TOPO to generate pCR4-GWCCD1 #2. The insert was sequenced resulting in the full-length CCD1 ORF after in silico assembly of the appropriate sequences. CcCCD1 was then aligned with the most homologous GenBank sequences, and found to encode a protein with 83% homology to *L. esculentum* (AY576001) and 78% homology to *L. esculentum* (AY576002; Simkin et al., 2004b) CCD1s, 82% homology to the *Petuniaxhybrida* (AY576003; Simkin et al., 2004a) CCD1, and 79% homology to *Arabidopsis thaliania* (AJ005813; Neill et al., 1998) CCD1 (Table 12).

TABLE 12

Identity of the *Coffea camphora* carotenoid cleavage dioxygenase 1 full amino acid sequence with the most homologous GenBank sequences.

| Gene name (accession number) | Publication | % identity[1] |
|---|---|---|
| *Coffea canephora* | NP[2] | 100 |
| *Lycopersicon esculentum* (AY576001) | Simkin et al., 2004b | 83 |
| *Petunia x hybrida* (AY576003) | Simkin et al., 2004a | 82 |

TABLE 12-continued

Identity of the *Coffea camphora* carotenoid cleavage dioxygenase 1 full amino acid sequence with the most homologous GenBank sequences.

| Gene name (accession number) | Publication | % identity[1] |
|---|---|---|
| *Arabidopsis thaliana* (AJ005813) | Neill et al., 1998 | 79 |
| *Lycopersicon esculentum* (AY576002) | Simkin et al., 2004b | 78 |

Figure 4J:
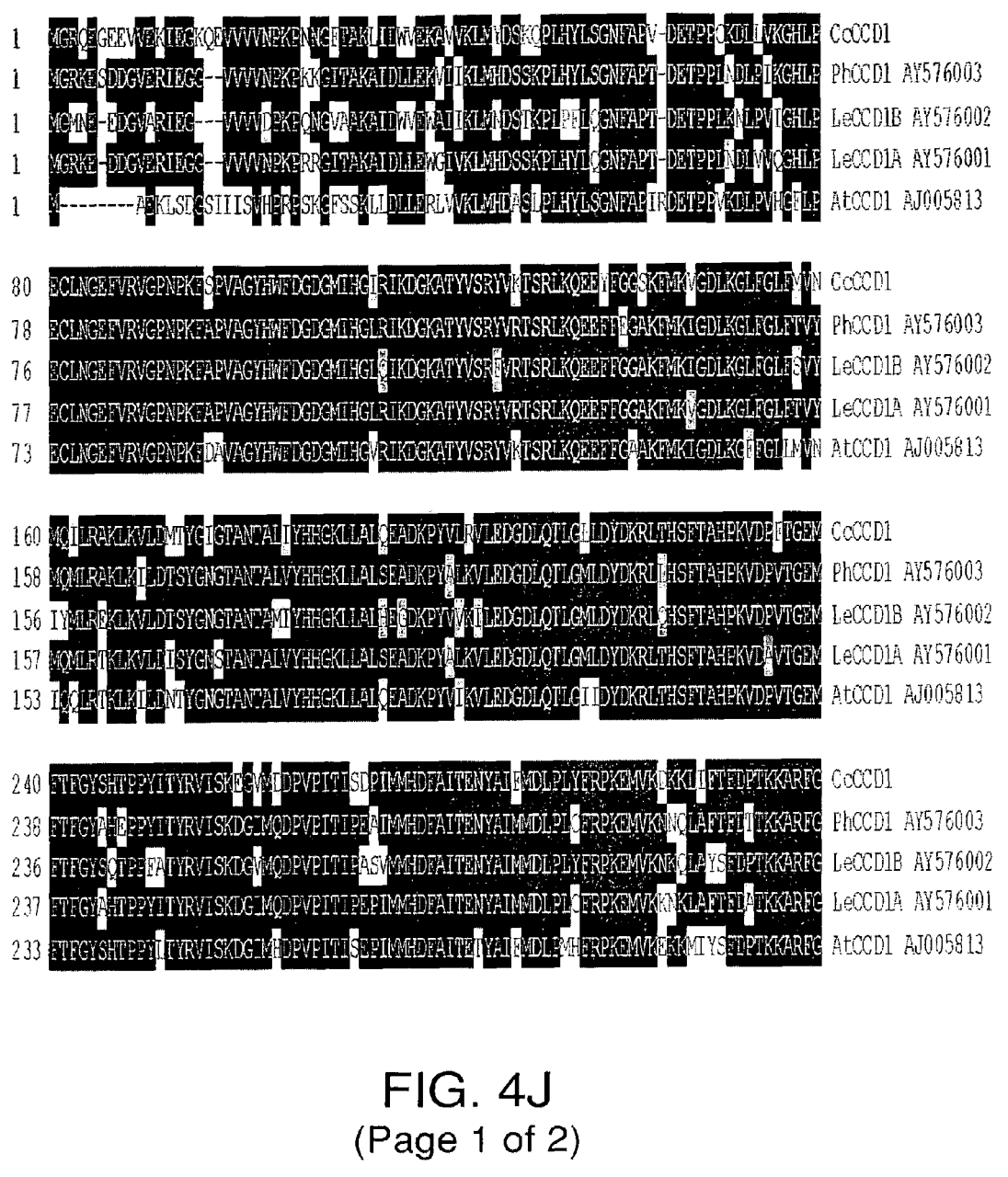

[1]Identities were individually calculated with clustal W using default parameters with the full-length ORF
[2]NP = not published FIG. 4J shows the CcCCD1 full amino acid sequence aligned with the four most homologous sequences in the GenBank non-redundant protein database.

II. Fibrillin

Proteins referred to as plant fibrillins or plastid lipid associated proteins are widespread from cyanobacteria to higher plants (Laizet et al., 2004), and in the latter case in diverse tissues, in association with a variety of different lipidic structures. Without being bound to any particular theory or mechanism of action, fibrillin proteins are believed to be involved in the stabilization of lipid structures in an aqueous environment (Vishnevetsky et al., 1999). In addition, lipoprotein structures in which fibrillins have been found may contain carotenoids (in greater or lesser quantities). The overexpression of fibrillin in tobacco chloroplasts was reported to lead to an increase in plastoglobule number, lipoprotein structures implicated in carotenoid sequestration (Rey et al., 2000). It may be, therefore, that fibrillin can lead to modifications in the carotenoid "sink". This is supported by the results of Li et al. (2001) who reported that carotenoid over-accumulation might be associated with the proliferation of deposition structures rather than changes in the expression of the carotenogenic genes or the abundance of the enzymes in the *Brassica oleracea* mutant Or. Likewise, overexpression of the fibrillin protein in coffee grain may lead to carotenoid stockage during grain development.

A full-length cDNA clone (cccs16w15e14) showing 70%, 61% and 60% homology with the fibrillin proteins of *Capsicuin annuum* (S56633; Deruère et al., 1994a) and *Arabidopsis thaliana* (NM-118350 and NM-116640; Laizet et al., 2004) respectively has been identified in the *C. canephora* EST database (Table 13).

TABLE 13

Identity of the *Coffea canephora* fibrillin amino acid sequence with the most homologous GenBank sequences.

| Gene name (accession number) | Publication | % identity[1] |
|---|---|---|
| *Coffea canephora* | NP[2] | 100 |
| *Lycopersicon esculentum* (SGN-U213598) | TIGR | 72 |
| *Capsicum annuum* (S56633) | Deruère et al., 1994a | 70 |
| *Arabidopsis thaliana* (NM-118350) | Laizet et al., 2004 | 61 |
| *Arabidopsis thaliana* (NM-116640) | Laizet et al., 2004 | 60 |

[1]Identities were individually calculated with clustal W using default parameters with the full-length ORF
[2]NP = not published FIG. 4K shows the *Coffea canephora* fibrillin amino acid sequence aligned with the three most homologous sequences in the GenBank non-redundant protein database.

EXAMPLE 3

Transcript Expression in Coffee Grain

Using the TaqMan assays, relative amounts of transcripts for PSY, PDS, ZDS, PTOX, LεCY, βCHY, ZEP, VDE, CCD1, NCED3 and FIB1 were quantified in coffee grain from *Coffea canephora* and *C. arabica*.

Figure 5J:
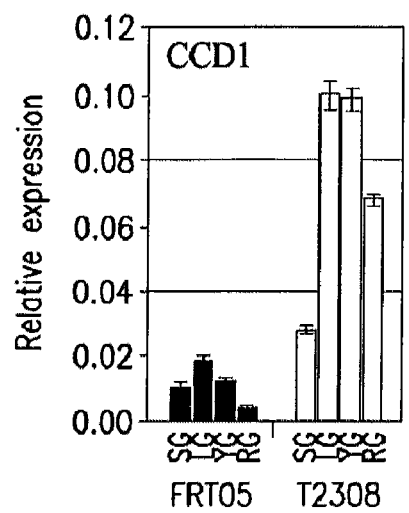
FIG. 5. Expression of carotenoid and apocarotenoid biosynthetic genes during seed maturation: Comparison between Robusta FRT-05 and Arabica T2308. Transcript levels for A) PSY, B) PDS, C) ZDS, D) PTOX, E) LϵCY, F) βCHY, G) ZEP, H) VDE, J) CCD1, K) NCED3 and L) FIB1, in the grain of *C. canephora*, (FRT05; black bars) and *C. arabica* (T2308; grey bars). The expression levels are determined relative to the expression of transcripts of the constitutively expressed RPL39 gene in the same samples. SG, Small green grain; LG, large grain; YG, yellow grain; RG, ripe grain.
Figure 5K:
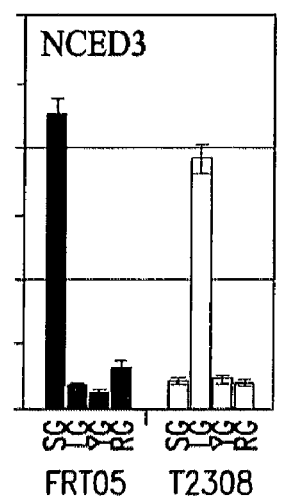
Figure 5L:
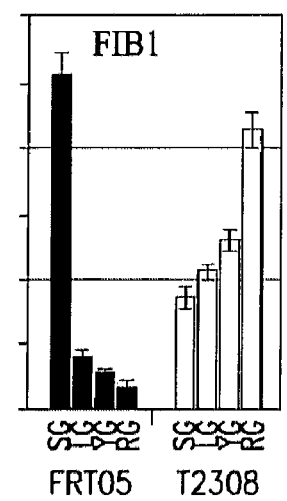

The results shown in FIG. 5 provide a comparison of the QRT-PCR expression data obtained for *C. canephora* (FRT05) with those from *C. arabica* (T2308). Apart from some clear expression differences for the small green stage, the two robusta samples showed relatively similar expression patterns but showed significant expression pattern differences with the single arabica sample analysed. These data suggest that there are potentially significant differences in the expression patterns of the carotenoid pathway genes in the coffee grain of arabica and robusta varieties.

Moreover, as can be seen in FIG. 5 confirm that each transcript exhibits expression in grain during development. Low expression of PSY, the first biosynthetic enzyme, in coffee grain may be important for carotenoid accumulation in coffee grain (FIG. 5A). The condensation of two molecules of geranylgeranyl diphosphate into phytoene by PSY has been found to be a rate limiting reaction in several different plant species and tissues at different stages of development. A significant difference between arabica and robusta grain was observed at the level of PTOX transcript accumulation (FIG. 5D). PTOX transcripts have been shown to be significantly higher in all grain stages in arabica when compared to robusta grain. Given the importance of PTOX in phytoene desaturation, determined in the arbidopsis mutant immutans (Carol et al., 1999) and tomato ghost mutant (Josse et al., 2000), it is believed that PTOX may play an important role in carotenoid biosynthesis during grain development. Another important, difference between arabica and robusta grain is observed with CCD1 transcript levels, which appear to increase in arabica grain during development in contrast to a decrease observed in robusta (FIG. 5J). Given the importance of CCD1 in flavor volatile formation, a more detailed analysis of CCD1 transcript levels in the grain of three *C. canephora* genotypes (BP409, FRT05, FRT64) and one *C. arabica* (T2308) genotype was carried out. In all three *C. canephora* genotypes, CCD1 transcript either decreased or remained low during development (FIG. 6A). In contrast, CCD1 transcript in *C. arabica* (T2308) increased 4-fold early on in development and remained high throughout development (FIG. 6A). At the end of the maturation period, CCD1 transcript levels were approximately 4-fold (BP409) to 20-fold (FRT05) higher in *C. arabica* when compared to *C. canephora*.

EXAMPLE 4

Activity of CCD1 and βCHY in *E. coli*

Figure 6C:
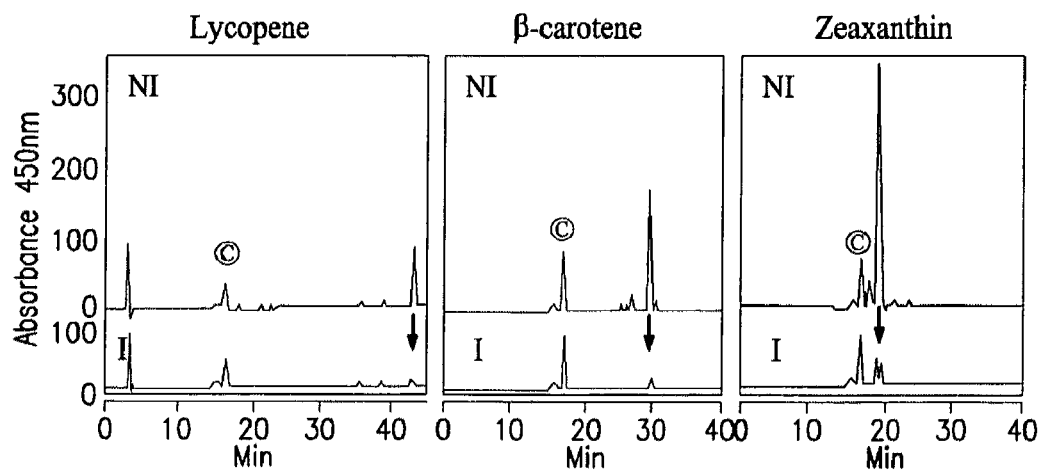
Figure 6B:
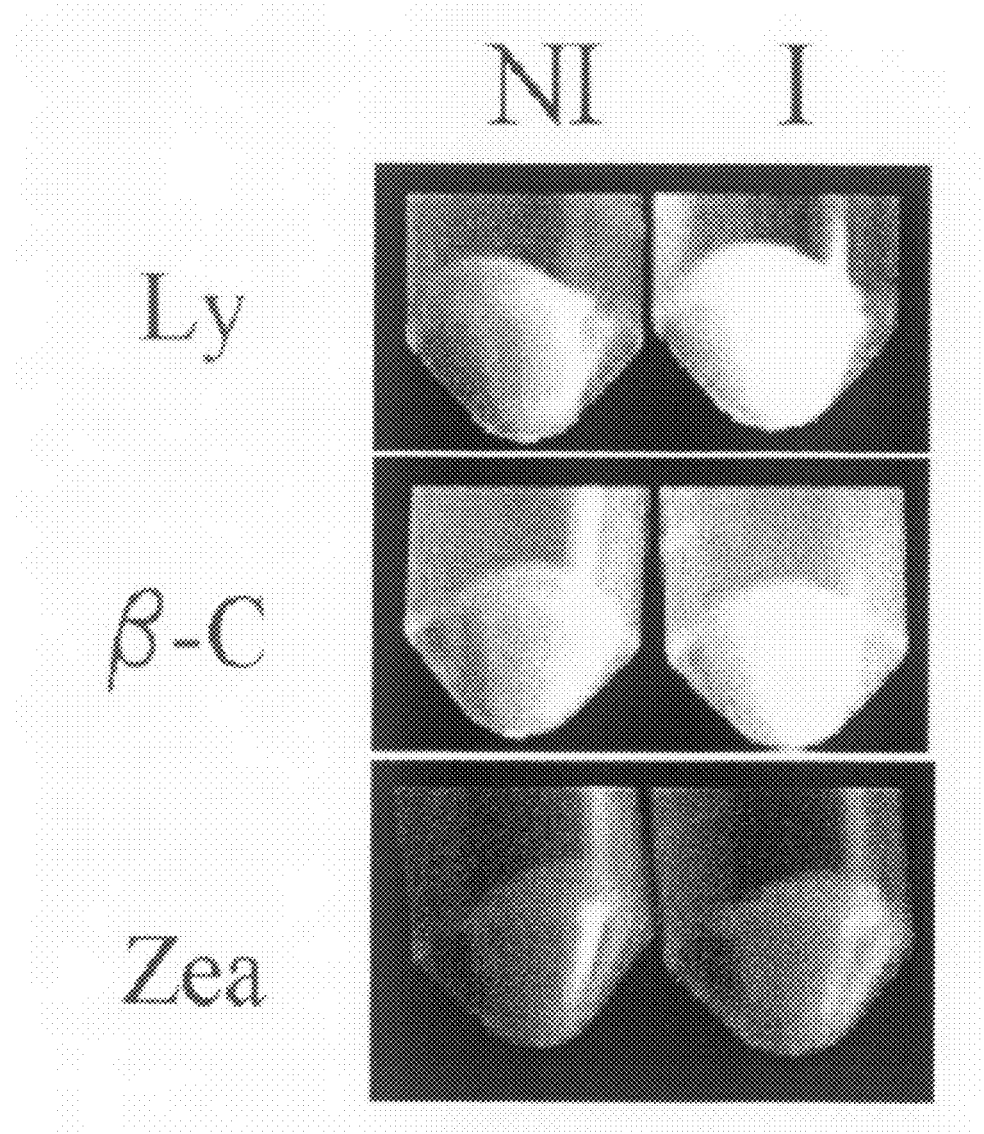

Plasmids expressing recombinant CcCCD1 protein (pD-EST17-CcCCD1) were introduced into strains of *E. coli* previously engineered to accumulate different carotenoid compounds (Cunningham et al. 1994; Cunningham et al. 1996; Sun et al. 1996). The carotenoids that accumulate in these strains impart color upon the cells and a change or loss of color indicates that the carotenoids have been modified by the new gene product introduced. When each of the two recombinant proteins was expressed in cells producing lycopene, β-carotene or zeaxanthin, loss of color was observed (FIG. 6B). These observations are consistent with the results previously reported by Simkin et al. (2004b). These results confirm that the coffee CCD1 enzyme can catabolize a range of linear and cyclic carotenoid substrates resulting in the formation of a range of apocarotenoids depending on the carotenoid substrate provided.

Plasmids expressing recombinant CcβCHY protein (pD-EST17-CcβCHY) were introduced into strains of *E. coli* previously engineered to accumulate β-carotene or zeaxanthin. The loss of colour observed in FIG. 6B was confirmed by HPLC-PDA analysis (FIG. 6C). To assess the loss of colour observed, carotenoids were analysed and quantified as follows:

Analysis and detection of carotenoids from *E. coli* by HPLC-PDA. The method of Fraser et al. (2002) was used to perform HPLC-PDA analyses. The separations were performed on a C30 reverse-phase column (250×4.6 mm) manufactured by YMC and purchased from Interchim (France). The mobile phases used were methanol (A), water/methanol (20/80 by vol) containing 0.2% ammonium acetate (B) and tert-methyl butyl ether (C). The gradient used was 95% A/5% B isocratically for 12 minutes, a step to 80% A/5% B/15% C at 12 minutes, followed by a linear gradient to 30% A/5% B/65% C for 30 min. Fraser et al. (2000)

Analysis and detection of carotenoids from *Coffea* by HPLC. The method used to analyse and quantify carotenoids from *C. arabica* (T2308) and *C. canephoia* (FRT05) grain is detailed in Senger et al. (1993). Briefly, 8 to 9 grains were ground in liquid nitrogen and freeze dried. A known quantity of astaxanthin dissolved in methanol was added to an empty tube and lyophilised. Sixty milligrams (60 mg) of freeze dried material was added to the tube and was extracted using methanol:chloroform (1:3 by vol) and partitioned against 50 mM Tris-HCl pH 7.0 (2 vols). HPLC separations were performed on a C18 reverse-phase column (Macherey-Nagel). The solvent consisted initially of 85% acetonitrilelmethanol (75:25) and 15% water, followed by a gradient decreasing water content to 8% in 12 min, to 5% over the next 10 min and then to 0% over the next 3 min. 100% acetonitrile/methanol was then kept until the end of the run.

Figure 7B:
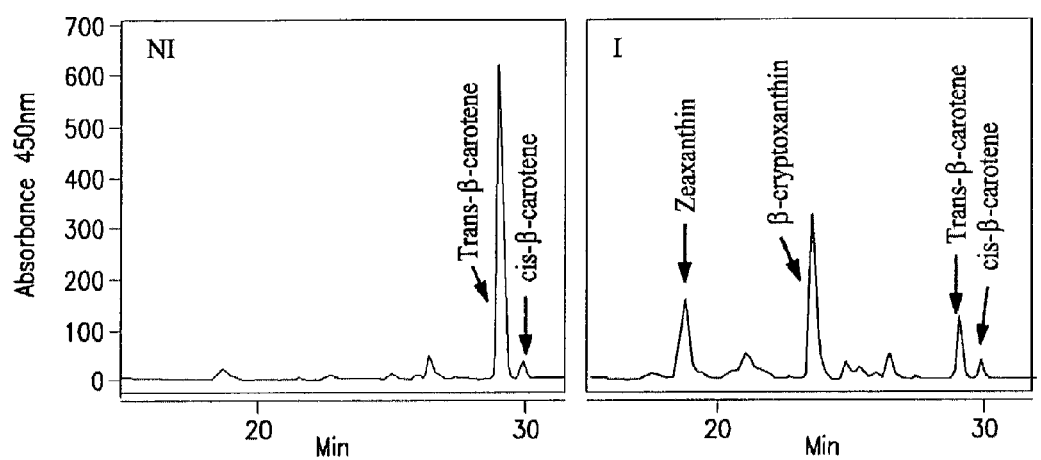

Quantification of carotinoids was achieved from dose-response curves and identification of carotenoids was achieved by co-chromatography and comparative spectral properties acquired on-line. A color change from a deep-orangey yellow to a bright yellow was observed in the presence of α-carotene due to the activity of βCHY, which converts β-carotene to zeaxanthin via the intermediate β-cryptoxanthin (FIG. 1D to 1G). These observations are consistent with the results previously reported by Sun et al. (1996). No such color change was observed in zeaxanthin accumulating strains, which were bright yellow before and after induction (FIG. 7A). To confirm the color change, carotenoids were extracted from the cells and analyzed by HPLC. FIG. 7B confirms the presence of β-carotene as the principal carotenoid prior to induction of pDEST17-CcβCHY. Following the induction, the peak representing β-carotene has been reduced and two new peaks representing zeaxanthin and the intermediate β-cryptoxanthin are observed. These data show that CcβCHY has a β-carotene hydroxylase activity resulting in the formation of β-cryptoxanthin and zeaxanthin from β-carotene.

Also, as can be seen in FIG. 6C, in the non-induced cultures (NI), peaks representing lycopene, β-carotene and zeaxanthin are observed. Following induction of CCD1, the accumulation of each of these carotenoids was significantly reduced (I), whilst the peak of astaxanthin added to the extract as a loading control remains the same size. These data indicate that the coffee CCD1 protein can catabolize both linear and cyclic carotenoid substrates. Significant expression of CCD1 in coffee grain (particularly arabica grain) has been detected indicating that this enzyme is probably generating carotenoid degradation products in the grain, molecules that are both normal cell metobolites and, in some cases, potential coffee aroma/aroma precursors.

EXAMPLE 5

Analysis of the Carotenoids in Immature and Mature Green Grain of Coffee

It has recently been shown that mature arabica and robusta coffee grain contain low levels of the carotenoids lutein and zeaxanthin (Degenhardt et al., 2004). As it is known that carotenoid levels in some seeds diminish as maturation progresses (Bonham-Smith et al., 2006), we examined the carotenoid levels found in immature arabica and robusta grain and compared these to the levels found in mature grain from the same varieties. The HPLC profiles obtained are presented in FIG. 8 and the quantified levels are given in Table 14.

The presence of diverse carotenoids in the coffee grain was shown by the HPLC analysis. As shown in FIGS. 8A and B, a chromatogram taken at 450 nm shows the presence of neoxanthin (1), violaxanthin (2), lutein (3), α-carotene (4), and β-carotene (5) in the green coffee grain. Significant level of chlorophylls A and B (peaks a and b) were also detected, which is likely responsible for the green color of non-roasted coffee beans. Lycopene was not detected in coffee grain, possibly due to the rapid turnover of this intermediate in the pathway. A chromatogram taken at 280 nm shows a peak that may represent phytoene, the first true carotenoid and a potential precursor for the formation of geranylacetone (VI) (data not shown).

As anticipated, significantly higher levels of lutein was found in the immature grain versus the mature grain. Interestingly, the experiments presented here also detected several other carotenoids in the coffee grain. In the immature grain, low levels of four other carotenoids can be clearly seen, neoxanthin, violaxanthin, α-carotene and β-carotene. As noted previously for coffee leaves (below), the presence of α-carotene was unexpected, but the identity of this peak was confirmed when its spectrum and retention time was found to be identical to an α-carotene standard extracted from carrot root (data not shown).

We observed no significant quantities of zeaxanthin in either mature arabica or robusta grain samples used in contrast to the previous report (Degenhardt et al., 2004). To confirm the observation that zeaxanthin is not present, samples were reanalyzed on a C30 column as described by Fraser et al. (2000), providing a more complete separation of lutein and zeaxanthin. Even using this method, no zeaxanthin was detected in these samples (data not shown).

ESTs for PSY and BCH were detected in the grain at 30 weeks of development. Given the presence of the terminal carotenoids lutein and neoxanthin in coffee grain (see FIG. 1 and FIG. 8), it is believed that all the enzymes involved in carotenoid biosynthesis are expressed at sufficient levels to maintain flux through the pathway. The CCD1 transcript was also detected in grain at 30 weeks development and is likely responsible for the formation of α-ionone (VI) and β-damascenone (IX) in vivo.

TABLE 14

Carotenoids content (μg/g dw) in *Coffea arabica* (T2308) and *C. canephora* (FRT05) grain.

| peak | carotenoid | T2308 | FRT05 |
|---|---|---|---|
| | LARGE GREEN GRAIN | | |
| 4 | α-Carotene | 7.7 (±1.7) | 2.5 (±0.3) |
| 5 | β-Carotene | 2.6 (±0.6) | 4.1 (±0.7) |

TABLE 14-continued

Carotenoids content (μg/g dw) in *Coffea arabica* (T2308) and *C. canephora* (FRT05) grain.

| peak | carotenoid | T2308 | FRT05 |
|---|---|---|---|
| 3 | Lutein | 24.2 (±4.8) | 29.4 (±1.8) |
| 2 | Violaxanthin | 1.9 (±0.3) | 2.7 (±0.3) |
| 1 | Neoxanthin | 4.6 (±0.9) | 5.3 (±0.3) |
|   | Total μg/g dw | 41.0 | 44.0 |
| a | Chlorophyll a | 180.9 (±17.0) | 156.7 (±9.3) |
| b | Chlorophyll b | 61.6 (±11.8) | 76.3 (±6.9) |
| RED GRAIN | | | |
| 4 | ι-Carotene | 0.3 (±0.1) | 0.1 (±0.0) |
| 5 | ι-Carotene | 0.1 ((0.0) | 0.2 ((0.0) |
| 3 | Lutein | 3.4 ((0.9) | 2.1 ((0.3) |
| 2 | Violaxanthin | 0.2 ((0.1) | ND |
| 1 | Neoxanthin | 0.4 (( | ND |
|   | Total μg/g dw | 4.5 | 2.5 |
| a | Chlorophyll a | 12.7 (±3.9) | 6.7 (±2.4) |
| b | Chlorophyll b | 8.1 (±2.4) | 5.2 (±1.1) |

Numbers represent the peaks in FIG. 8. Values are means of 3 to 4 determinations. Standard deviations are shown in brackets. 60 mg samples were extracted as described in materials and methods. ND = Not detected The results presented here show that green coffee seeds contains at least five different carotenoids. The presence of the terminal carotenoids—lutein and neoxanthin—in coffee grain (see FIG. 8 and Table 14) indicates that all the enzymes involved in carotenoid biosynthesis are expressed at sufficient levels to maintain flux through the pathway. Coffee grains develop within small cherries surrounded by a thin pericarp, thus they are shielded from direct sunlight. However, coffee grain were found to contain both chlorophyll a and b, which is likely responsible for the green colour of un-roasted coffee beans.

We also detected the presence of a quantity of α-carotene at a concentration of 2-18% of total carotenoids depending on the variety. Generally, green tissues such as leaves accumulate significant quantities of β-carotene and lutein (for review see Frank and Cogdell, 1996 and references therein) but not α-carotene. However, α-carotene can be found in the leaves of some plants such as carrot (Kock and Goldman, 2005). The presence of α-carotene in mature green coffee grain is consistent with the previous report of α-carotene in coffee leaves (Simkin et al., submitted), with the mature green grain of *C. arabica* containing a higher relative level than *C. canephora*. These higher α-carotene levels in the mature green grain of *C. arabica* may be related to higher LϵCY transcript levels, which we found to be significantly higher in *C. arabica* when compared to *C. canephora* (see FIG. 5). LϵCY along with LβCY is responsible for the formation of α-carotene from lycopene (Ronen et al., 1999). It should be mentioned that lower relative lutein levels in *C. arabica* versus *C. canephora* accompany a higher relative α-carotene content of *C. arabica* grain. This result is consistent with that previously observed in coffee leaves (below). Thus, though other possibilities exist, one possibility may be that the accumulation of α-carotene at the expense of lutein is due to lower transcript levels or enzyme activity of ϵ-carotene hydroxylase, which along with βCHY is responsible for the formation of lutein from α-carotene (Tian et al., 2004; Tian and DellaPenna, 2004).

It remains possible that the global difference of the carotenoid profile between the *C. arabica* versus *C. canephora* presented here could be the result of species-specific or variety-specific variations. It is also possible some of the differences observed are at least partially the result of the different growth conditions under which the trees were grown.

EXAMPLE 6

Promoter Isolation and Vector Construction

The 5' upstream region of NCED3 from *Coffea canephora* was recovered using the Genomewalker kit (BD Biosciences). Briefly, 2.5 μg of *Coffea canephora* BP409 DNA was cut independently with DraI, EcoRV, PvuI and StuI to form GenomeWalk banks DL1, DL2, DL3 and DL4, respectively. Following purification, 0.5 μg DNA was ligated to the GenomeWalker adaptators (25 μM) following the manufacturer's protocol. Subsequent PCR reactions contained 1× buffer and 5 mM $MgCl_2$, 200 μM each of dATP, dCTP, dGTP and dTTP, and 1 units of LA Taq polymerase (Takara, Combrex Bio, Belgium), and 200 nM primer GWNCED3F (5'-AAGCAGAAGCAGTCAGGGACTTCTACC-3') (SEQ ID NO.:40) and 200 nM of the GenomeWalker adaptator primer AP1(5'-GTAATACGACTCACTATAGGGC-3'; Genomewalker kit) (SEQ ID NO.:28). The reaction mixture was incubated for 10 min at 94° C., followed by 7 amplification cycles of 25 sec at 94° C./4 min at 72° C., and then 32 amplification cycles of 25 sec at 94° C./4 min at 67° C. The PCR reaction was diluted 1/200 and the used for a second PCR reaction using 200 nM of nested primer GWNCED3R (5'-TATCCAGTACACCGAATCTTGACACC-3') (SEQ ID NO.:41) and 200 nM of nested GenomeWalker adaptator primer AP2 (5'-ACTATAGGGCACGCGTGGT-3'; Genomewalker kit) (SEQ ID NO.:29). Nested PCR was incubated for 10 min at 94° C., followed by 5 amplification cycles of 25 sec at 94° C./4 min at 72° C. and then 22 amplification cycles of 25 sec at 94° C./4 min at 67° C. A 1075 bp genomic fragment was recovered from DL2 and cloned into the pCR4-TOPO vector (Invitrogen) to make pCR4-GWNCED#4. The insert of this clone was sequenced resulting in a 1104 bp sequence upstream of the ATG start codon of NCED3 (SEQ ID NO:25).

EXAMPLE 7

Carotenoid Content in Coffee Leaves

Figure 9C:
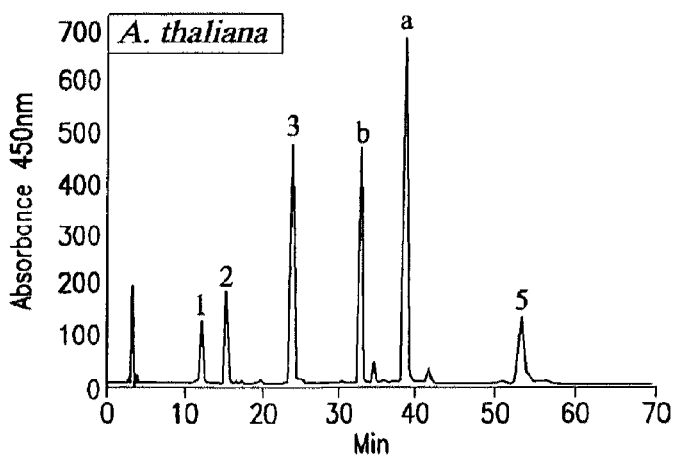

Analysis of coffee leaf extracts by HPLC showed that *C. canephora* contained a higher content of carotenoids than *C. arabica*. Quantification of each carotenoid (Table 15) revealed that the two species show similar relative distributions of the carotenoids neoxanthin, violaxanthin and β-carotene (approximately. 12-13% β-carotene, 14-16% violaxanthin and 13-14% neoxanthin). One of the most striking observations from Table 15 is the presence of a significant amount of α-carotene (peak 4: FIG. 9), an intermediate in lutein synthesis, which does not normally accumulate in leaves from most species including *Arabidopsis* (FIG. 9C). To confirm the identity of the peak as α-carotene, the spectrum and retention time were compared and found to be identical to those of an α-carotene standard extracted from carrot root. A comparison of α-carotene levels in *C. arabica* and *C. canephora* showed that *C. arabica* leaves contained a higher relative α-carotene levels (12% and 3.5% of total carotenoids respectively). In contrast, *C. canephora* had higher relative lutein levels (54%, as compared to 48% in *C. arabica*). The higher α-carotene levels may be related to higher LϵCY transcript levels, which were shown to be significantly higher in *C. arabica* than in *C. canephora*. Additionally, since *C. canephora* leaves had higher relative lutein levels than those from *C. arabica*, and since α-carotene is the direct lutein precursor, it may be that the higher lutein content in *C. canephora* leaves could be directly related to the lower levels of α-carotene and, conversely, the lower lutein content in *C. arabica* leaves is related to the higher α-carotene content.

TABLE 15

Carotenoids content (mg/g dw) in *Coffea arabica* (T2308) and *C. canephora* (FRT05) leaves.

| peak | carotenoid | T238 | FRT05 |
|---|---|---|---|
| 4 | α-Carotene | 232.4 (±24.6) | 104.5 (±6.1) |
| 5 | β-Carotene | 238.8 (±26.6) | 387.4 (±10.6) |
| 3 | Lutein | 987.3 (±135.6) | 1629.5 (±48.4) |
| 2 | Violaxanthin | 292.4 (±34.1) | 473.4 (±5.6) |
| 1 | Neoxanthin | 287.8 (±39.4) | 374.9 (±3.51) |
|   | Total mg/g dw | 2038.7 | 2969.7 |
| a | Chlorophyll A | 9640 (±1028) | 11572 (±140) |
| b | Chlorophyll B | 3096 (±408) | 4524 (±169) |

Values are means of 3 to 4 determinations. Standard deviations are shown in brackets. 60 mg samples were extracted as described in materials and methods. Numbers represent the peaks in FIG. 7.

Although the connection between carotenoid metabolism in the leaves and that in the grain is not precisely clear at this time, the data above again support the idea that there are small but significant differences in the carotenoid profiles of arabica and robusta coffees. It is believed that these profile differences contribute to some of the differences in the environmental stress tolerance and grain qualities that generally exist between these two coffee species.

EXAMPLE 8

Quantitative Expression Analysis of Coffee Genes Involved in Carotenoid Biosynthesis and Storage Under Drought Stress Conditions We evaluated the changes of carotenoid gene expression in leaves of 3-year old *C. arabica* (catimor) plants caused by prolonged drought stress. For this experiment, leaf samples were taken at the different times (T=0, 3, 4, 5, and 6 weeks) from two well-watered control plants and from two parallel un-watered plants. RNA was prepared from each of the samples. For water deficit samples, total RNA from leaf tissue was isolated using the RNeasy Plant Mini Kit (Qiagen, Valencia, Calif.). RNA samples were treated with RNase-free DNase (Qiagen) and purified using the Qiagen mini-column. Concentration and purity of total plant RNA was determined by spectrophotometric analysis. The quantification was verified for all RNA samples in each experiment by formaldehyde agarose gel electrophoresis and visual inspection of rRNA bands upon ethidium bromide staining. cDNA was prepared from approximately 2 μg total RNA using poly-dT primer according to the protocol in the Superscript II Reverse Transcriptase Kit (Invitrogen, Carlsbad, Calif.).

The RNA was then used for quantitative RT-PCR expression analysis of the carotenoid and FIB1 genes (FIG. 10). Expression analysis showed that the level of FIB1, PSY, ZDS, PTOX, βCHY, and VDE transcripts each increased during the drought period. In contrast, the amount of ZEP transcript increased under the initial stress before decreasing, whereas transcript for LeCY decreased rapidly to undetectable levels in some samples. No significant increase in the amount of PDS transcript was observed during the first 5 weeks of drought stress, and only one of the two plants showing the most severe stress symptoms showed an increase in PDS after 6 weeks post drought.

We also evaluated the changes of carotenoid cleavage dioxygenase gene expression in leaves caused by prolonged drought. The amount of CCD1 transcript increased under conditions of water deficit and increased slowly throughout the 6 week sampling period. In contrast, transcript for NCED3 increased significantly early on, before decreasing throughout the remaining sampling period.

Small differences in transcript levels were observed in the control samples collected on different days (although samples were all collected at the same time each day). This observation is probably a manifestation that minor changes in the environmental conditions between the two plants can slightly affect the expression of carotenoid genes. Similarly, the differences in transcript levels changes produced in each of the stressed plants were possibly due to sample-specific differences in the rate of dehydration following the removal of irrigation. The plant set on the left of the histograms showed the most severe physical symptoms of water deficit at the end of the test period (data not shown).

Water deficit can result in an increased production of reactive oxygen species. Carotenoids, being involved in the protection against oxidative stresses, may be submitted to higher turnover rates under drought stress. This suggests that higher synthesis rates may be needed to maintain suitable pigment levels in water-deprived plants (see Simkin et al., 2003b). Hence, we examined the expression of some carotenoid biosynthetic genes in coffee leaves under water deficit conditions. Because the FIB1/CDSP34 gene is known to respond to stressors, such as water deficit, which affects thylakoid function (Manac'h and Kuntz, 1999; Langenkämper et al., 2001), we examined the FIB1 expression levels in this experiment as a clear control for water stress. As expected, the expression of FIB1 was induced strongly in coffee by drought stress (FIG. 10). This result confirmed that the experimental conditions used here led to a strong stress response within the plastid. This stress response is also detected in other parts of the cell because additional experiments using the same samples clearly demonstrated that the water stress-inducible gene dehydrin CcDH1a (DQ323987) was very strongly induced in the water-stressed samples and not in the watered controls (G. Pagny and J. McCarthy; unpublished results).

We note that lycopene epsilon cyclase transcript level in coffee leaves decreased under conditions of water deficit to undetectable levels. This apparent down-regulation could re-direct the metabolic flux from the lutein branch of the pathway into the xanthophyll (zeaxanthin, antheraxanthin, and violaxanthin) branch of the pathway. The xanthophylls contribute to the dissipation of excess energy from photosynthesis through a mechanism known as the xanthophyll cycle. Two enzymes are involved in this cycle, ZEP and VDE. ZEP catalyses the conversion of zeaxanthin to antheraxanthin and then to violaxanthin. VDE catalyses the reverse reaction. Under normal conditions, ZEP activity results in a high violaxanthin and low zeaxanthin content, whilst VDE activity (and zeaxanthin accumulation) is induced under excess light conditions (Ruban et al., 1994; Woitsch and Römer, 2003). Our results show that, under normal growth conditions, the amount of ZEP transcript is approximately 10-fold greater than that of VDE transcript in *C. arabica*. Interestingly, the data obtained using the water stressed plants indicate that ZEP transcript level first increases during the early part of the stress response, then decreases as the stress signal(s) become stronger. The decrease in the amount of ZEP transcript is accompanied by a concomitant steady increase in the amount of VDE transcript in water-stressed plants. It may be that this gene expression regulation contributes to the optimal operation of the xanthophyll cycle under water stress. Overall, these results suggest that one or more of the following strategies could be used to improve the protection of green plant tissues, including those of coffee, from water stress: 1) increase synthesis of carotenoids in general, for example by increasing coffee PSY expression earlier in the stress response (more responsive to signal), 2) reduce the expression of LeCY earlier in the stress response to improve carotenoid entry into the xanthophyll synthesis pathway, or 3) improve the functional capacity of the xanthophyll cycle (for example by increasing VDE expression). These and other potential improvements in the stress response in coffee are now made possible by the isolation of the full length cDNA sequences for the coffee carotenoid and apocarotenoid biosynthetic pathway enzymes presented here.

The present invention is not limited to the embodiments described and exemplified herein, but is capable of variation and modification within the scope of the appended claims.

References:

Agrawal, G. K., Yamazaki, M., Kobayashi, M., Hirochika, R., Miyao, A. and Hirochika, H. (2001) Screening of the rice viviparous mutants generated by endogenous retrotransposon Tos17 insertion. Tagging of a zeaxanthin epoxidase gene and a novel ostatc gene. *Plant Physiol.* 125, 1248-1257.

Akiyama M, Murakami K, Ohtani N, Iwatsuki K, Sotoyama K, Wada A, Tokuno K, Iwabuchi H, Tanaka K. (2003). Analysis of volatile compounds released during the grinding of roasted coffee beans using solid-phase microextraction. *J Agric Food Chem.* 51(7): 1961-1969.

Albrecht M, Klein A, Hugueney P, Sandmann G, Kuntz M. (1995). Molecular cloning and functional expression in *E. coli* of a novel plant enzyme mediating ζ-carotene desaturation. *FEBS Lett.* 372: 199-202.

Al-Babili S, Hugueney P, Schledz, M, Frohnmeyer H, Laule O, Beyer P. (2000). Identification of a novel gene encoding for neoxanthin synthase from *Sola tuberosum*. *FEBS Lett* 485: 168-172

Al-Babili S, Ye X, Lucca P, Beyer P. (2001). Biosynthesis of beta-carotene (provitamin A) in rice endosperm achieved by genetic engineering. *Novartis Found Symp.* 236: 219-232.

Arrach N, Fernandez-Martin R, Cerda-Olmedo E, Avalos J. (2001). A single gene for lycopene cyclase, phytoene synthase, and regulation of carotene biosynthesis in *Phycomyces*. *PNAS* 98(4):1687-1692.

Aust O, Stahl W, Sies H, Tronnier H, Heinrich U (2005). Supplementation with tomato-based products increases lycopene, phytofluene, and Phytoene levels in human serum and protects against UV-light induced erythema. *Int. J. Vitam. Nutr. Res.* 75:54-60.

Baldwin E A, Nisperos-Carriedo M O, Baker R, Scott, J W. (1991). Quantitative analysis of flavor parameters of six Florida tomato cultivars (*Lycopersicon esculentum*). *J. Agri, Food. Chem.* 39: 1135-1140.

Baldwin E A, Scott J W, Shewmaker C K, Schuch W. (2000). Flavor trivia and tomato aroma: biochemistry and possible mechanisms for control of important aroma components. *Hort. Sci.* 35(6): 1013-1021.

Bartley G E, Viitanen P V, Bacot K O, Scolnik P A. (1992). A tomato gene expressed during fruit ripening encodes an enzyme of the carotenoid biosynthesis pathway. *J. Biol. Chem.* 267: 5036-5039.

Bartley, G E and Ishida, B K (1999). Zeta-carotene desaturase from tomato. *Plant Physiol.* 121:1383.

Bäumlein H, Nagy I, Villarroel R, Inzé D, Wobus U. 1992. Cis-analysis of a seed protein gene promoter: the conservative R Y repeat CATGCATG within the legumin box is essential for tissue-specific expression of a legumin gene. *Plant J* 2: 233-239.

Beyer P, Al-Babili S, Ye X, Lucca P, Schaub P, Welsch R, Potrykus I. (2002). Golden Rice: introducing the beta-carotene biosynthesis pathway into rice endosperm by genetic engineering to defeat vitamin A deficiency. *J Nutr.* 132(3):506S-510S.

Boelsma E, Hendriks H F J, Roza L. (2001) Nutritional skin care: health effects of micronutrients and fatty acids. *Am. J. Clin. Nutr.* 73:853-864.

Bouvier F, d'Harlingue A, Hugueney P, Marin E, Marion-Poll A, Camara B. (1996). Xanthophyll biosynthesis. Cloning, expression, functional reconstitution, and regulation of beta-cyclohexenyl carotenoid epoxidase from pepper (*Capsicum annuum*). *J Biol. Chem.* 271(46):28861-28867.

Bouvier F, Dogbo O, Camara B. (2003b). Biosynthesis of the food and cosmetic plant pigment bixin. *Science* 300: 289-291.

Bouvier F, Suire C, Mutterer J, Camara B. (2003a). Oxidative remodeling of chromoplast carotenoids: identification of a carotenoid cleavage dioxygenase CsCCD and CsZCD genes involved in Crocus secondary metabolic biogenesis. *Plant Cell* 15: 47-62.

Bouvier F, Isner J C, Dogbo O, Camara B. (2005). Oxidative tailoring of carotenoids: a prospect towards novel functions in plants. *Trends Plant Sci.* 10(4):187-194.

Bramley P M. (2000). Is lycopene beneficial to human health? *Phytochem.* 54(3):233-236.

Britton G. (1988). Biosynthesis of carotenoids. In: Goodwin T W (ed), Plant pigments. Academic Press, London, pp 133-182.

Britton, G. (1995). Structure and properties of carotenoids in relation to function. *FASEB J.*, 9:1551-1558.

Bugos R C, Hieber A D, Yamamoto H Y. (1998). Xanthophyll cycle enzymes are members of the lipocalin family, the first identified from plants *Biol. Chem.* 273(25):15321-15324.

Burbidge A, Grieve T, Terry C, Corlett J, Thompson A, Taylor I. (1997). Structure and expression of a cDNA encoding zeaxanthin epoxidase, isolated from a wilt-related tomato (*Lycopersicon esculentum* Mill.) *J. Exp. Bot.* 48, 1749-1750.

Burden R S, Dawson, G W, Taylor H F. (1972). Synthesis and plant growth inhibitory properties of (±)-O-methylxanthoxin. *Phytochem.* 11: 2295-2299.

Buttery R, Ling L. (1993). Volatiles of tomato fruit and plant parts: relationship and biogenesis. Pp 23-34. In: Teranishi R, Buttery R, Sugisawa H, (eds) Bioactive volatile compounds from plants. ACS Books. Washington D.C.

Buttery R G, Seifert R M, Guadagni D G, Ling L C. (1971). Characterisation of additional components of tomato. *J. Agri, Food. Chem.* 19: 524-529.

Buttery R G, Teranishi R, Ling L C, Flath R, Stern D. (1988). Quantitative studies on origins of fresh tomato aroma volatiles. *J. Agric. Food Chem.* 36: 1247-1250.

Buttery R G, Teranishi R, Ling L C, Turnbaugh J G (1990). Quantitative and sensory studies on tomato paste volatiles. *J. Agric. Food Chem,* 38: 336-340.

Buttery R G, Teranishi R, Ling L C. (1987). Fresh tomato aroma volatiles: a quantitative study. *J. Agri, Food. Chem.* 35: 540-544.

Carol P, Stevenson D, Bisanz C, Breitenbach J, Sandmann G, Mache R, Coupland G, Kuntz M. (1999). Mutations in the *Arabidopsis* gene IMMUTANS cause a variegated phenotype by inactivating a chloroplast terminal oxidase associated with phytoene desaturation. *Plant Cell,* 11: 57-68.

Clarke R, Vitzthum O. Coffee: Recent Developments. Blackwell Science 2001.

Comhaire F H, Mahmoud A. (2003). The role of food supplements in the treatment of the infertile man. *Reprod Biomed Online.* 7(4):385-391.

Cunningham F X, Gantt E. (1998). Genes and enzymes of carotenoid biosynthesis in plants. *Annu Rev Plant Physiol Plant Mol Biol* 49: 557-583.

Cunningham F X, Gantt E. (2001). One ring or two? Determination of ring number in carotenoids by lycopene epsilon-cyclases. *PNAS* 98(5):2905-2910.

Cunningham F X Jr, Gantt E. (2005). A study in scarlet: enzymes of ketocarotenoid biosynthesis in the flowers of *Adonis aestivalis. Plant J.* 41(3):478-492.

Cunningham F X, Pogson B, McDonald K A, DellaPenna D, Grant E. (1996). Functional analysis of the beta and epsilon lycopene-cyclase enzymes of *Arabidopsis* reveals a mechanism for control of cyclic carotenoid formation. *Plant Cell* 8(9): 1613-1626.

Cunningham F X, Sun Z, Chamovitz D, Hirschberg C. (1994). Molecular Structure and Enzymatic Function of Lycopene Cyclase from the Cyanobacterium *Synechococcus* sp Strain PCC7942. *Plant Cell,* 6:1107-1121.

Czerny M, Grosch W. (2000). Potent odorants of raw Arabica coffee. Their changes during roasting. *J Agric Food Chem.* 48(3):868-872.

Czerny M, Mayer F, Grosch W. (1999). Sensory study on the character impact odorants of roasted arabica coffee *J Agric Food Chem.* 47(2): 695-699

Demmig-Adams B, Gilmore A M, Adams, W W. (1996). In vivo functions of carotenoids in higher plants. *FASEB J.* 10:403-412.

Deruère J, Bouvier F, Steppuhn J, Klien A, Camara B, Kuntz M. (1994a). Structures and expression of two plant genes encoding chromoplast-specific proteins: occurrence of partially spliced transcripts. *Biochem. Biophys. Res. Com.* 199(3): 1144-1150.

Deruère J, Römer S, d'Harlingue A, Backhaus R A, Kuntz M, Camara B. (1994b). Fibril assembly and carotenoid overaccumulation in chromoplasts: a model for supramolecular lipoprotein structures. *Plant Cell* 6: 119-133.

Di Mascio, P., M. E. Murphy, and H. Sies. (1991) Antioxidant defense systems: the role of carotenoids, tocopherols, and thiols. *Am. J. Clin. Nutr.,* 53:194 S-200S.

da Silva E A, Toorop P E, van Aelst A C, Hilhorst H W. (2004). Abscisic acid controls embryo growth potential and endosperm cap weakening during coffee (*Coffea arabica* cv. Rubi) seed, germination. *Planta.* 220(2):251-261.

Eugster C H, Hürlimann H, Leuenberger H J. (1969). Crocetindialdehyd und Crocetinhalbaldehyd als Blütenfarbstoffe von *Jacquinia angustifolia. Helv. Chim. Acta* 52: 89-90.

Fay L B, Newton A, Simian H, Robert F, Douce D, Hancock P, Green M, Blank, I. (2003). Potential of gas chromatography-orthogonal acceleration time-of-flight mass spectrometry (GC-oaTOFMS in flavor research. *J. Agric. Food Chem.* 51: 2708-2713.

Fraser P D, Bramley P M. (2004). The biosynthesis and nutritional uses of carotenoids. *Prog Lipid Res.* 43(3): 228-265.

Fraser P D, Pinto M E, Holloway D E, Bramley P M. (2000). Technical advance: application of high-performance liquid chromatography with photodiode array detection to the metabolic profiling of plant isoprenoids. *Plant J* 24: 551-558.

Fray R G, Wallace A, Fraser P D, Valero D, Hedden P, Bramley P M, Grierson D. (1995). Constitutive expression of a fruit phytoene synthase gene in transgenic tomatoes causes dwarfism by redirecting metabolites from the gibberellin pathway. *Plant J* 8: 693-701.

Gaziano J M, Hennekens C H (1993). The role of beta-carotene in the prevention of cardiovascular disease. *Ann. NY Acad. Sci.* 691:148-155.

Hieber A D, Bugos R C, Yamamoto H Y. (2000). Plant lipocalins: violaxanthin de-epoxidase and zeaxanthin epoxidase. *Biochim Biophys Acta.* 1482(1-2): 84-91.

Hirschberg J. Molecular Biology of Carotenoid Biosynthesis (in) Britton, G., Liaaen-Jensen, S, and Pfander, H. (Eds.); CAROTENOIDS VOL 3: BIOSYNTHESIS AND METABOLISM: 149-194; Birkhaeuser Verlag, Basel, Boston, Berlin (1998).

Hsieh K, Huang A H C. (2004). Endoplastic reticulum, oleosins, and oils in seeds and tapetum cells. *Plant Physiol* 136: 3427-3434.

Huang A H C. (1996). Oleosins and oil bodies in seeds and other organs. *Plant Physiol* 110(4): 1055-1061.

Hugueney P, Römer S, Kuntz M, Camara B. (1992). Characterisation and molecular cloning of a flavoprotein catalysing the synthesis of phytofluene and zeta-carotene in *Capsicum* chromoplasts. *Eur. J. Biochem.* 209: 399-407.

Inoue K (2004). Carotenoid hydroxylation-P450 finally! *Trends Plant Sci.* 9(11):515-517.

Josse E M, Simkin A J, Gaffé J, Laboure A M, Kuntz M, Carol P. (2000). A plastid terminal oxidase associated with carotenoid desaturation during chromoplast differentiation. *Plant Physiol.* 123: 1427-1436.

Josse E M, Jalcaraz J P, Labouré A M, Kuntz M. (2003). In vitro characterisation of plastid terminal oxidase (PTOX). *Eur. J. Biochem.* 270: 3787-3794.

Jyonouchi H, Zhang L, Tomita Y. (1993). Studies of immunomodulating actions of carotenoids. II. Astaxanthin enhances in vitro antibody production to T-dependent antigens without facilitating polyclonal B-cell activation. *Nutr Cancer.* 19(3): 269-280.

Kato-Noguchi H. (1992). An endogenous growth inhibitor, 3-hydroxy-β-ionone. I. Its role in light-induced growth inhibition of hypocotyls of *Phaseolus vulgaris. Physiol. Plant.* 86: 583-586

Kato-Noguchi H, Kosemura S, Yamamura S, Hasegawa, K. (1993). A growth inhibitor, R-(−)-3-hydroxy-β-ionone, from light-grown shoots of a dwarf cultivar of *Phaseolus vulgaris.* Phytochem. 33: 553-555.

Kiefer C, Hessel S, Lampert J M, Vogt K, Lederer M O, Breithaupt D E, von Lintig J. (2001). Identification and characterization of a mammalian enzyme catalyzing the asymmetric oxidative cleavage of provitamin A. *J Biol. Chem.* 276(17): 14110-14116.

Kjeldsen F, Christensen L P, Edelenbos M. (2003). Changes in volatile compounds of carrots (*Daucus carota* L.) during refrigerated and frozen storage. *J. Agric. Food Chem.* 51: 5400-5407.

Kuntz M. (2004). Plastid terminal oxidase and its biological significance. *Planta* 218: 896-899.

Laizet Y, Pontier D, Mache R, Kuntz M. (2004). Subfamily organization and phylogenetic origin of genes encoding plastid lipid-associated proteins of the fibrillin type. *J. Genome Sci. Tech.* 3(1):19-28.

Li, L., Paolillo, D J., Parthasarathy, M V., DiMuzio, E M., Garvin, D F. (2001). A novel gene mutation that confers abnormal patterns of -carotene accumulation in cauliflower (*Brassica oleracea* var. *botrytis*). *Plant J.* 26(1): 59-67.

Lin C, Mueller L A, McCarthy J, Pétiard V, Crouzillat D, Tanksley S (2005) Generation and analysis of a coffee EST database: Deductions about gene repertoire, expression and evolution. (Submitted).

Lindgren L O, Stalberg K G, Hoglund A S. (2003). Seed-specific overexpression of an endogenous *Arabidopsis* phytoene synthase gene results in delayed germination and increased levels of carotenoids, chlorophyll, and abscisic acid. Plant Physiol. 132(2): 779-785.

Lutz A, Winterhalter P. (1992) Biooxidative cleavage of carotenoids—important route to physiological active-plant constituents. Tetrahedron Lett. 33: 5169-5172.

Marin E, Nussaume L, Quesada A, Gonneau M, Sotta B, Hugueney P, Frey A, Marion-Poll A. (1996). Molecular identification of zeaxanthin epoxidase of *Nicotiana plumbaginifolia*, a gene involved in abscisic acid biosynthesis and corresponding to the ABA locus of *Arabidopsis thaliana*. EMBO J. 15(10): 2331-2342.

Mahattanatawee K, Rouseff R, Valim M F, Naim M. (2005). Identification and aroma impact of norisoprenoids in orange juice. J Agric Food Chem. 53(2): 393-397.

Matthews-Roth M M. (1993). Carotenoids in erythropoietic protoporphyria and other photosensitivity diseases. Ann. NY Acad. Sci. 691: 127-138.

Mayne S T. (1996). Beta-carotene, carotenoids, and disease prevention in humans. FASEB J. 10: 690-701.

Mbeguie-A-Mbeguie D, Fils-Lycaon B (2000). Molecular cloning and nucleotide sequences of PA-ZE (Accession No. AF071888) and PA-ZE2 (Accession No. AF159948), two cDNAs from apricot fruit coding for a zeaxanthin epoxidase. Gene expression during fruit ripening. Plant Physiol. 122 (1): 291.

Moehs, C P, Tian, L., Osteryoung, K W and Dellapenna, D. (2001) Analysis of carotenoid biosynthetic gene expression during marigold petal development. Plant Mol. Biol. 45: 281-293.

Nagao A. (2004) Oxidative conversion of carotenoids to retinoids and other products J. Nutr. 134(1): 237S-240S Neill S J, Burnett E C, Desikan R, Hancock J T. (1998) Cloning of a wilt-responsive cDNA from *Arabidopsis thaliana* suspension culture cDNA library that encodes a putative 9-cic-epoxy-carotenoid dioxygenase. J. Exp. Bot. 49: 1893-1894.

Ortiz A, Ortiz A, Vega F E, Posada F. (2004). Volatile composition of coffee berries at different stages of ripeness and their possible attraction to the coffee berry borer *Hypothenemus hampei* (Coleoptera: Curculionidae). J Agric Food Chem. 52(19): 5914-5918.

Paine J A, Shipton C A, Chaggar S, Howells R M, Kennedy M J, Vernon G, Wright S Y, Hinchliffe E, Adams J L, Silverstone A L, Drake R. (2005). Improving the nutritional value of Golden Rice through increased pro-vitamin A content. Nature Biotechnol. 23(4): 482-487.

Parry A D, Horgan R. (1991) Carotenoids and abscisic acid (ABA) biosynthesis in higher plants. Physiol. Plant. 82: 320-326.

Pecker, I., Chamovitz, D., Linden, H., Sandmann, G. and Hirschberg, J. (1992) A single polypeptide catalyzing the conversion of phytoene to zeta-carotene is transcriptionally regulated during tomato fruit ripening. Proc. Natl. Acad. Sci. U.S.A. 89: 4962-4966.

Pogson B, McDonald K A, Truong M, Britton G, DellaPenna D. (1996). *Arabidopsis* carotenoid mutants demonstrate that lutein is not essential for photosynthesis in higher plants. Plant Cell 8(9): 1627-1639.

Ravanello M P, Ke D, Alvarez J, Huang B, Shewmaker C K. (2003). Coordinate expression of multiple bacterial carotenoid genes in canola leading to altered carotenoid production. Metab Eng. 5(4): 255-263.

Ray J, Moureau P, Bird C, Bird A, Grierson D, Maunders M, Truesdale M, Bramley P, Schuch W. (1992). Cloning and characterization of a gene involved in phytoene synthesis from tomato. Plant Mol. Biol. 19: 401-404.

Rey P, Gillet B, Romer S, Eymery F, Massimino J, Peltier G, Kuntz M. (2000). Over-expression of a pepper plastid lipid-associated protein in tobacco leads to changes in plastid ultrastructure and plant development upon stress. Plant J. 21(5): 483-494.

Richman A S, Gijzen M, Starratt A I N, Yang Z, Brandle J E. (1998). Diterpene synthesis in *Stevia rebaudiana*: recruitment and up-regulation of key enzymes from the gibberellin biosynthetic pathway. Plant J. 19 (4): 411-421.

Römer S, Hugueney P, Bouvier F, Camara B, Kuntz M. (1993). Expression of the genes encoding the early carotenoid biosynthetic enzymes in *Capsicum annuum*. Biochem. Biophys. Research Cominun. 196: 1414-1421.

Ronen G, Cohen M, Zamir D, Hirschberg J. (1999). Regulation of carotenoid biosynthesis during tomato fruit development: expression of the gene for lycopene epsilon-cyclase is down regulated during ripening and is elevated in the mutant Delta. Plant J. 17: 341-351.

Sandmann, G. (1994). Carotenoid biosynthesis in micro-organisms and plants. Eur. J. Biochem. 223: 7-24.

Sato, S., Nakamura, Y., Kaneko, T., Katoh, T., Asamizu, E. and Tabata, S. (2000). Structural analysis of *Arabidopsis thaliana* chromosome 3. I. Sequence features of the regions of 4,504,864 bp covered by sixty P1 and TAC clones. DNA Res. 7 (2): 131-135

Schwartz S H, Qin X, Zeevaart J A D (2001). Characterization of a novel carotenoid cleavage dioxygenase from plants. J. Biol. Chem. 276: 25208-25211.

Scolnik, P A and Bartley, G E (1995) Nucleotide sequence of zeta-carotene desaturase from *Arabidopsis*. Plant Physiol. 109: 1499.

Seddon J M, Ajani U A, Sperduto R D, Hiller R, Blair N, Burton T C, Farber M D, Garoudos E S, Haller J, Miller D T, Yannuzzi L A, Willet W. (1994). Dietary carotenoids, vitamins A, C, and E, and advanced age-related macular degeneration. J. Am. Med. Assoc. 272: 1413-1420.

Shewmaker C K, Sheehy J A, Daley M, Colburn S, Ke D Y. (1999). Seed-specific overexpression of phytoene synthase: increase in carotenoids and other metabolic effects. Plant J. 20(4): 401-412.

Sies H, Stahl W. (2004). Carotenoids and UV protection. Photochem. Photobiol. Sci. 8: 749-752.

Simkin A J, Underwood B A, Auldridge M, Loucas H M, Shibuya K, Clark D G, Klee H J. (2004a). Circadian regulation of the PhCCD1 carotenoid dioxygenase controls emission of β-ionone, a fragrance volatile of petunia flowers. Plant Physiol. 136(3): 3504-3514.

Simkin A J, Schwartz S H, Auldridge M, Taylor M G, Klee H J. (2004b). The tomato carotenoid cleavage dioxygenase 1 genes contribute to the formation of the flavour volatiles β-ionone, pseudoionone and geranylacetone. Plant J. 40(6): 882-894.

Simkin A J, Laizet Y, Kuntz M. (2004c). Plastid lipid associated proteins of the fibrillin family: structure, localisation, function and gene expression. Rec Res Dev Biochem 5: 307-316.

Soar, C. J., Speirs, J., Maffei, S. M. and Loveys, B. R. (2004). Gradients in stomatal conductance, xylem sap ABA and bulk leaf ABA along canes of *Vitis vinifera* cv Shiraz: biochemical and molecular biological evidence indicating their source. Funct. Plant Biol. 31, 659-669.

Spanier A M, Flores M, Toldra F, Aristoy M C, Bett K L, Bystricky P, Bland J M (2004). Meat flavor: contribution of proteins and peptides to the flavor of beef. Adv Exp Med. Biol. 542: 33-49.

Stalberg K, Lindgren O, Ek B, Hoglund A S. (2003). Synthesis of ketocarotenoids in the seed of *Arabidopsis thaliana*. *Plant J.* 36: 771-779.

Stevens A A. (1970). Relationship between polyene-carotene content and volatile compound composition of tomatoes. *J. Am. Soc. Hort. Sci.* 95: 461-464.

Suzuki M, Matsumoto S, Mizoguchi M, Hirata S, Takagi K, Hashimoto I, Yamano Y, Ito M, Fleischmann P, Winterhalter P, Morita T, Watanabe N. (2002). Identification of (3S, 9R)- and (3S,9S)-megastigma-6,7-dien-3,5,9-triol 9-O-beta-D-glucopyranosides as damascenone progenitors in the flowers of *Rosa damascena* Mill. *Biosci Biotechnol Biochem.* 66(12): 2692-2697.

Tan B C, Schwartz S H, Zeevaart J A D, McCarty D R. (1997) Genetic control of abscisic acid biosynthesis in maize. *Proc. Natl. Acad. Sci. USA*, 94: 12235-12240.

Tan B C, Joseph L M, Deng W T, Liu L, Li Q B, Cline K, McCarty D R. (2003) Molecular characterisation of the 9-cis epoxycarotenoid dioxygenase gene family. *Plant J* 35: 44-56.

Tanaka T, Morishita Y, Suzui M, Kojima T, Okumura A, Mori H. Chemoprevention of mouse urinary bladder carcinogenesis by the naturally occurring carotenoid astaxanthin Carcinogenesis, Vol 15, 15-19, Copyright © 1994 by Oxford University Press.

Tandon J S, Katti S B, Rüedi P, Eugster C H. (1979) Crocetindialdehyde from *Coleus forskolii Briq., Labiatae. Helv. Chim. Acta* 274: 27062707.

Taylor A (1993). Cataract: relationship between nutrition and oxidation. *J. Am. Coll. Nutr.* 12: 138-146.

Thompson, A. J., Thorne, E. T., Burbridge, A., Jackson, A. C., Sharp, R. E. and Taylor, I. B. (2004). complementation of notabilis, an abscisic acid-deficient mutant of tomato: importance of sequence context and utility of partial complementation. *Plant Cell Environ.* 27 (4): 459-471.

Tian L, DellaPenna D. (2001). Characterization of a second carotenoid beta-hydroxylase gene from *Arabidopsis* and its relationship to the LUT1 locus. *Plant Mol. Biol.* 47(3): 379-388.

Tian L, DellaPenna D. (2004). Progress in understanding the origin and functions of carotenoid hydroxylases in plants. *Arch Biochem Biophys.;* 430(1):22-29.

Tian L, Musetti V, Kim J, Magallanes-Lundback M, DellaPenna D. (2004). The *Arabidopsis* LUT1 locus encodes a member of the cytochrome p450 family that is required for carotenoid epsilon-ring hydroxylation activity. *PNAS* 6; 101(1): 402-407.

Variyar P S, Ahmad R, Bhat R, Niyas Z, Sharma A. (2003). Flavoring components of raw monsooned arabica coffee and their changes during radiation processing. *J Agric Food Chem.* 51(27): 7945-7950.

von Lintig J, Vogt K. (2000). Filling the gap in vitamin A research. Molecular identification of an enzyme cleaving beta-carotene to retinal. *J. Biol. Chem.* 275(16): 11915-11920.

Watzl B, Bub A, Brandstetter B R, Rechkemmer G. (1999). Modulation of human T-lymphocyte functions by the consumption of carotenoid-rich vegetables. *Br. J. Nutr.* 82: 383-389.

Winterhalter P, Schreier P. (1995) The generation of norisoprenoid volatiles in starfruit (*Averrhoa carambola* L.): A review. *Food Rev. International* 11: pp. 237-254.

Winterhalter P, Rouseff R. (2002). Carotenoid-derived aroma compounds. (Washington DC: American Chemical Society).

Vishnevetsky M, Ovadis M, Vainstein A. (1999). Carotenoid sequestration in plants: the role of carotenoid-associated proteins. *Trends Plant Sci.* 4(6): 232-235.

The present invention is not limited to the embodiments described and exemplified above, but is capable of variation and modification within the scope of the appended claims.

What is claimed:

1. A nucleic acid molecule isolated from coffee (*Coffea* spp.), having a coding sequence that encodes a phytoene synthase, wherein the phytoene synthase has an amino acid sequence at least about 85% identical to SEQ ID NO:13.

2. The nucleic acid molecule of claim 1, wherein the phytoene synthase has an amino acid sequence at least about 90% identical to SEQ ID NO:13.

3. The nucleic acid molecule of claim 1, wherein the coding sequence is an open reading frame of a gene, or a mRNA molecule, or a cDNA molecule.

4. A vector comprising the coding sequence of the nucleic acid molecule of claim 1.

5. The vector of claim 4, which is an expression vector selected from the group of vectors consisting of plasmid, phagemid, cosmid, baculovirus, bacmid, bacterial, yeast and viral vectors.

6. The vector of claim 4, wherein the coding sequence of the nucleic acid molecule is operably linked to a constitutive promoter, or an inducible promoter, or a tissue-specific promoter.

7. The vector of claim 4, wherein the tissue specific promoter is a coffee seed specific promoter.

8. The vector of claim 7, wherein the coffee seed specific promoter is a carotenoid or apocarotenoid gene promoter.

9. The vector of claim 8, wherein the carotenoid or apocarotenoid gene promoter comprises SEQ ID NO:25.

10. A host cell transformed with the vector of claim 4.

11. The host cell of claim 10, which is a plant cell selected from the group of plants consisting of coffee, tobacco, *Arabidopsis*, maize, wheat, rice, soybean barley, rye, oats, sorghum, alfalfa, clover, canola, safflower, sunflower, peanut, cacao, tomatillo, potato, pepper, eggplant, sugar beet, carrot, cucumber, lettuce, pea, aster, begonia, chrysanthemum, delphinium, zinnia, and turfgrasses.

12. A fertile plant produced from the plant cell of claim 11.

13. A method of modulating flavor or aroma of coffee beans, comprising modulating production or activity of one or more phytoene synthase enzymes within coffee seeds, wherein the phytoene synthase has an amino acid sequence at least about 85% identical to SEQ ID NO:13.

14. The method of claim 13, comprising increasing production or activity of the one or more phytoene synthase enzymes.

15. The method of claim 13, comprising decreasing production or activity of the one or more phytoene synthase enzymes.

16. The method of claim 14, comprising increasing expression of one or more endogenous genes encoding phytoene synthase enzymes within the coffee seeds.

17. The method of claim 14, comprising introducing a phytoene synthase-encoding transgene into the plant.

18. The method of claim 15, comprising introducing a nucleic acid molecule into the coffee that inhibits the expression of one or more genes encoding phytoene synthase.

19. The nucleic acid molecule of claim 1, wherein the phytoene synthase has an amino acid sequence at least about 95% identical to SEQ ID NO:13.

20. The nucleic acid molecule of claim 13, wherein the phytoene synthase has an amino acid sequence at least about 95% identical to SEQ ID NO:13.

* * * * *